(12) United States Patent
Bergsma et al.

(10) Patent No.: US 8,951,764 B2
(45) Date of Patent: Feb. 10, 2015

(54) PRODUCTION OF ISOPRENOIDS UNDER NEUTRAL PH CONDITIONS

(75) Inventors: Martien H. Bergsma, Zoetermeer (NL); Anthony R. Calabria, Wilmington, DE (US); Gopal K. Chotani, Cupertino, CA (US); William A. Cuevas, San Francisco, CA (US); Gang Duan, Shanghai (CN); Sung Ho Lee, North Liberty, IA (US); Ying Qian, Wuxi (CN); Vivek Sharma, North Liberty, IA (US); Jayarama K. Shetty, Pleasanton, CA (US); Bruce A. Strohm, Beloit, WI (US); Paula Johanna Maria Teunissen, Saratoga, CA (US); Hongxian Xu, Wuxi (CN)

(73) Assignee: Danisco US Inc., Palo Alto, CA (US)

( * ) Notice: Subject to any disclaimer, the term of this patent is extended or adjusted under 35 U.S.C. 154(b) by 78 days.

(21) Appl. No.: 13/566,923

(22) Filed: Aug. 3, 2012

(65) Prior Publication Data

US 2013/0203140 A1 Aug. 8, 2013

Related U.S. Application Data

(60) Provisional application No. 61/515,830, filed on Aug. 5, 2011.

(51) Int. Cl.
| | | |
|---|---|---|
| C12N 5/07 | (2010.01) | |
| C12P 19/14 | (2006.01) | |
| C12N 1/20 | (2006.01) | |
| C12P 5/00 | (2006.01) | |
| C12N 9/34 | (2006.01) | |
| C12N 9/10 | (2006.01) | |

(52) U.S. Cl.
CPC ......... C12P 5/007 (2013.01); C12Y 302/01003 (2013.01); C12N 9/2428 (2013.01); C12Y 205/0101 (2013.01); C12N 9/1085 (2013.01)
USPC ..... 435/166; 435/25; 435/252.3; 435/252.33; 435/254.2

(58) Field of Classification Search
USPC ................. 435/252.3, 252.33, 254.2, 254.11, 435/254.6, 166, 253.8, 256.7, 67; 524/573
See application file for complete search history.

(56) References Cited

U.S. PATENT DOCUMENTS

| | | | |
|---|---|---|---|
| 4,092,434 A | 5/1978 | Yoshizumi et al. | |
| 4,247,637 A | 1/1981 | Tamura et al. | |
| 4,514,496 A | 4/1985 | Yoshizumi et al. | |
| 4,618,579 A | 10/1986 | Dwiggins et al. | |
| 4,760,025 A | 7/1988 | Estell et al. | |
| 4,794,175 A | 12/1988 | Nunberg et al. | |
| 4,863,864 A | 9/1989 | Ashikari et al. | |
| 5,024,941 A | 6/1991 | Maine et al. | |
| 5,246,853 A | 9/1993 | Clarkson et al. | |
| 5,254,467 A | 10/1993 | Kretschmann et al. | |
| 5,464,760 A | 11/1995 | Tsai et al. | |
| 5,475,101 A | 12/1995 | Ward et al. | |
| 5,612,055 A | 3/1997 | Bedford et al. | |
| 5,847,276 A | 12/1998 | Mimken et al. | |
| 5,849,970 A | 12/1998 | Fall et al. | |
| 5,874,276 A | 2/1999 | Fowler et al. | |
| 6,022,725 A | 2/2000 | Fowler et al. | |
| 6,255,084 B1 | 7/2001 | Nielsen et al. | |
| 6,265,190 B1 | 7/2001 | Yedur et al. | |
| 6,268,328 B1 | 7/2001 | Mitchinson et al. | |
| RE37,393 E | 9/2001 | Donnelly et al. | |
| 6,303,352 B1 | 10/2001 | Cameron et al. | |
| 6,440,716 B1 | 8/2002 | Svendsen et al. | |
| 6,475,762 B1 | 11/2002 | Stafford et al. | |
| 6,596,521 B1 | 7/2003 | Chang et al. | |
| 6,620,924 B2 | 9/2003 | Nielsen et al. | |
| 7,262,041 B2 | 8/2007 | Baldwin et al. | |
| 7,320,882 B2 | 1/2008 | Rieping | |
| 7,332,309 B2 | 2/2008 | Rieping | |
| 7,354,752 B2 | 4/2008 | Dunn-Coleman et al. | |
| 7,413,879 B2 | 8/2008 | Dunn-Coleman et al. | |
| 7,666,634 B2 | 2/2010 | Rieping et al. | |
| 7,915,026 B2 | 3/2011 | Keasling et al. | |
| 8,415,136 B1 * | 4/2013 | Gardner et al. ............ 435/254.2 |
| 2006/0094080 A1 | 5/2006 | Dunn-Coleman et al. | |
| 2006/0193897 A1 | 8/2006 | Bedford et al. | |
| 2007/0141685 A1 | 6/2007 | Bai et al. | |
| 2007/0254354 A1 | 11/2007 | Millis et al. | |
| 2008/0038805 A1 | 2/2008 | Melis | |
| 2009/0203087 A1 | 8/2009 | Baldwin et al. | |
| 2009/0203102 A1 | 8/2009 | Cervin et al. | |
| 2009/0246845 A1 | 10/2009 | Breneman et al. | |
| 2009/0305360 A1 | 12/2009 | Breneman et al. | |
| 2009/0305935 A1 | 12/2009 | Cascao-Pereira et al. | |

(Continued)

FOREIGN PATENT DOCUMENTS

| | | |
|---|---|---|
| EP | 215594 | 3/1987 |
| EP | 244234 | 11/1987 |

(Continued)

OTHER PUBLICATIONS

Aleshin, A.E., et al. "Refined crystal structures of glucoamylase from *Aspergillus awamori* var. X100," J. Mol. Biol. 238: 575-591 (1994).

(Continued)

*Primary Examiner* — Kagnew H Gebreyesus

(74) *Attorney, Agent, or Firm* — Morrison & Foerster LLP

(57) ABSTRACT

Embodiments of the present disclosure relate to a process for producing isoprenoid precursor molecules and/or isoprenoids from a starch substrate by saccharification and/or fermentation. The saccharification is effectively catalyzed by a glucoamylase at a pH in the range of 5.0 to 8.0. At a pH of 6.0 or above, the glucoamylase possesses at least 50% activity relative to its maximum activity. The saccharification and fermentation may be performed as a simultaneous saccharification and fermentation (SSF) process.

28 Claims, 11 Drawing Sheets

(56) References Cited

U.S. PATENT DOCUMENTS

| | | | |
|---|---|---|---|
| 2010/0003716 | A1 | 1/2010 | Cervin et al. |
| 2010/0015686 | A1 | 1/2010 | Cascao-Pereira et al. |
| 2010/0048964 | A1 | 2/2010 | Calabria et al. |
| 2010/0086978 | A1 | 4/2010 | Beck et al. |
| 2010/0113846 | A1 | 5/2010 | McAuliffe et al. |
| 2010/0167370 | A1 | 7/2010 | Chotani et al. |
| 2010/0167371 | A1 | 7/2010 | Chotani et al. |
| 2010/0184178 | A1 | 7/2010 | Beck et al. |
| 2010/0196977 | A1 | 8/2010 | Chotani et al. |
| 2010/0279354 | A1* | 11/2010 | de Crecy ............... 435/71.1 |
| 2010/0311065 | A1 | 12/2010 | Ubersax et al. |
| 2011/0014672 | A1 | 1/2011 | Chotani et al. |
| 2011/0046422 | A1 | 2/2011 | McAuliffe et al. |
| 2011/0097769 | A1 | 4/2011 | Del Cardayre et al. |
| 2011/0159557 | A1 | 6/2011 | Beck et al. |
| 2012/0045812 | A1 | 2/2012 | Bergsma et al. |

FOREIGN PATENT DOCUMENTS

| | | |
|---|---|---|
| EP | 473 545 | 3/1992 |
| EP | 1 222 256 B1 | 7/2002 |
| WO | WO-2009/076676 A3 | 0/6200 |
| WO | WO-88/09795 A1 | 12/1988 |
| WO | WO-92/06209 A1 | 4/1992 |
| WO | WO-95/26397 A1 | 10/1995 |
| WO | WO-96/35796 A1 | 11/1996 |
| WO | WO-97/20920 A1 | 6/1997 |
| WO | WO-98/02550 A2 | 1/1998 |
| WO | WO-98/02550 A3 | 1/1998 |
| WO | WO-99/49740 A1 | 10/1999 |
| WO | WO-03/066816 A2 | 8/2003 |
| WO | WO-03/066816 A3 | 8/2003 |
| WO | WO-03/095659 A1 | 11/2003 |
| WO | WO-2004/033646 A2 | 4/2004 |
| WO | WO-2004/033646 A3 | 4/2004 |
| WO | WO-2005/001036 A2 | 1/2005 |
| WO | WO-2005/052148 A2 | 6/2005 |
| WO | WO-2005/052148 A3 | 6/2005 |
| WO | WO-2006/043178 A2 | 4/2006 |
| WO | WO-2006/043178 A3 | 4/2006 |
| WO | WO-2008/086811 A1 | 7/2008 |
| WO | WO-2008/137092 A2 | 11/2008 |
| WO | WO-2008/137092 A3 | 11/2008 |
| WO | WO-2009/048487 A1 | 4/2009 |
| WO | WO-2009/048488 A1 | 4/2009 |
| WO | WO-2009/067218 A2 | 5/2009 |
| WO | WO-2009/067218 A3 | 5/2009 |
| WO | WO-2009/076676 A2 | 6/2009 |
| WO | WO-2009/099783 A2 | 8/2009 |
| WO | WO-2009/099783 A3 | 8/2009 |
| WO | WO-2009/114403 A1 | 9/2009 |
| WO | WO-2009/132220 A2 | 10/2009 |
| WO | WO-2009/132220 A3 | 10/2009 |
| WO | WO-2010/003007 A2 | 1/2010 |
| WO | WO-2010/003007 A3 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/148150 A1 | 12/2010 |
| WO | WO-2011/075534 A2 | 6/2011 |
| WO | WO-2011/075534 A3 | 6/2011 |

OTHER PUBLICATIONS

Ashikari, et al. "Direct fermentation of raw corn to ethanol by yeast transformants containing a modified *Rhizopus* glucoamylase gene," *App. Microbio. Biotech.* 32:129-133 (1989).

Ashikari, et al. "Rhizopus Raw-Starch-Degrading glucoamylase: its cloning and expression in yeast," *Agric. Biol. Chem.* 50:957-964 (1986).

Ausubel, F. M., et al. "Introduction of DNA into Mammalian Cells," Current Protocols in Molecular Biology, Chapter 9, 1987.

Durand, H. et al. (1988). "Classical and Molecular Genetics Applied to *Trichoderma reesei* for the Selection of Improved Cellulolytic Industrial Strains," in *Biochemistry and Genetics of Cellulose Degradation*, Aubert, J.P. eds. et al. Academic Press, pp. 136-151.

Timberlake, W.E. "Cloning and Analysis of Fungal Genes," Chapter 3 in *More Gene Manipulations in Fungi*, Bennett, J.W. et al. eds., Academic Press, Inc., San Diego, CA, 1991, pp. 51-85.

Bernstein, M. et al. (Mar. 24, 2010). "On the Road to 'Sweet' Tires Made with a More Sustainable Process," ACS, located at <http://portal.acs.org/portal/acs/corg/content?_nfpb=true&_pageLabel=PP_ARTICLEMAIN&node_id=222&content_id=CNBP_024362&use_sec=true&sec_url_var=region1&_uuid=4f9f4a3e-f30e-45cf-a417-741446427124>, last visited on Dec. 16, 2011. 1 page.

Bhayana, et al. "Amino Acid Sequence of *Escherichia coli* Citrate Synthase," Biochemistry, 1984, 23: 2900-2905 (Figure 5).

Bhikhabhai, et al. "Isolation of Celluloytic Enzymes from *Trichoderma reesei* QM 9414," J. Appl. Biochem. 6:336-345 (1984).

Boel, E. et al. "Glucoamylases G1 and G2 from *Aspergillus niger* are synthesized from two different but closely related mRNAaS," The EMBO J. 3:1097-1102 (1984).

Boel, E. et al. "Two Different Types of Intervening Sequences in the Glucoamylase Gene from *Aspergillus niger*," The EMBO Journal, 3(7):1581-1585 (1984).

Bologna, et al. "*Escherichia coli* Malic Enzymes: Two Isoforms with Substantial Differences in Kinetic Properties, Metabolic Regulation, and Structure," Journal of Bacteriology, Aug. 2007, 189(16):5937-5946.

Brumbrubauer, et al., "Fractionation of cellulase and β-glucosidase in a *Trichoderma reesei* culture liquid by use of two-phase partitioning," Bioseparation 7:287-295 (1999).

Bunch, et al. "The IdhA Gene Encoding the Fermentative Lactate Dehydrogenase of *Escherichia coli*," Microbiology, 1997, 143:187-195.

Campbell, et al. "Improved Transformation Efficiency of *Aspergillus niger* Using the Homologus niaD Gene for Nitrate Reductase," Current Genetics, 1989, 16:53-56.

Cunningham, F.X. et al. (1998). "Genes and Enzymes of Carotenoid Biosynthesis in Plants," *Ann. Rev. Plant Physiol. Plant Mol. Biol.* 49:557-583.

Cunningham, F.X. et al. (Oct. 2000). "Evidence of a Role for LytB in the Nonmevalonate Pathway of Isoprenoid Biosynthesis," *Journal of Bacteriology* 182(20):5841-5848.

Danner, et al. (2011, e-pub. Apr. 12, 2011). "Four terpene synthases produce major compounds of the gypsy moth feeding-induced volatile blend of *Populus trichocarpa*," Phytochemistry 72:897-908.

Database Accession No. AED46507, "Glucoamylase SEQ ID No. 49," retrieved from EBI accession No. GSP:AED46507, Dec. 15. 2005.

Database Accession No. AEM52117, "*Humicola grisea* var. *thermoidea* mature glucoamylase,"retrieved from EBI accession No. GSP:AEM52117, Mar. 8, 2007.

Database accession No. AXQ57959, "*Trichoderma reesei* recombinant glucoamylase," retrieved from EBI accession No. GSP:AXQ57959 Oct. 29, 2009.

Doran, et al. "Fermentation of Crystalline Cellulose to Ethanol by *Klebsiella oxytoca* Containing Chromosomally Integrated *Zymomonas mobilis* Genes,"Biotechnol. Progress 9:533-538 (1993).

Duckworth, et al. "Structural Basis for Regulation in Gram-Negative Bacterial Citrate Synthases," Biochem Soc Symp. 54:83-92 (1987).

Ellouz, et al. "Analytical separation of *Trichoderma reesei* cellulases by ion-exchange fast protein liquid chromatography," Journal of Chromatography, 396:307-317 (1987).

Finkelstein, D.B. (1992). "Transformation," Chapter 6 in *Biotechnology of Filamentous Fungi*, Butterworth-Heinemann, Boston, MA, pp. 113-156.

Fliess, et al. "Characterization of cellulases by HPLC separation," Eur. J. Appl. Microbiol. Biotechnol. 17:314-318 (1983).

Goedegebuur, F. et al. "Cloning and Relational Analysis of 15 Novel Fungal Endoglucanases form Family 12 Glycosyl Hydrolase," Curr. Genet. 41:89-98 (2002, e-pub. May 7, 2002).

(56) References Cited

OTHER PUBLICATIONS

Goyal, A. et al. (1991). "Characteristics of fungal cellulases," *Bioresource Technology* 36:37-50.

Greenberg, J.P. et al. "Sub-Parts Per Billion Detection of Isoprene Using a Reduction Gas Detector with a Portable Gas Chormatograph," Atmos. Environ. 27A(16):2689-2692 (1993).

Harkki, et al. "A novel fungal expression system: secretion of active calf chymosin from the filamentous fungus *Trichoderma reese*," Bio/Technol. 7:596-603 (Jun. 1989).

Harkki, et al. "Genetic engineering of *Trichoderma* to produce stains with novel cellulase profiles," Enzyme Microb. Technol. 13:227-233 (Mar. 1991).

Harris, Chris, ed. (Jun. 2010). "Biolsoprene—a Renewable Product with Biofuel Potential," TheBioenergySite, two pages, Retrieved from the Internet: URL:http://www.thebioenergysite.com/articles/657/bioisoprene-a-renewable-product-with-biofuel-potential [retrieved on Dec. 4, 2012].

Hayashida, et al. "Molecular cloning of the glucoamylase I gene of *Aspergillus awamori* var. kawachi for localization of the raw-starch-affinity site," Agric. Biol. Chem. 53:923-929 (1989).

Hedl, et al. "*Enterococcus faecalis* Acetoacetyl-Coenzyme a Thiolase/3-Hydroxy-3-Methylglutaryl-Coenzyme a Reductase, a Dual-Function Protein of Isopentenyl Diphosphate Biosynthesis," Journal of Bacteriology 184(8):2116-2122, (Apr. 2002).

Houghton-Larsen, et al. "Cloning and characterization of a glucoamylase gene (GlaM) from the dimorphic zygomycete *Mucor circinelloides*," Appl. Microbiol. Biotechnol. 62:210-217 (2003).

Hsieh, et al. "Structure and Mechanism of an *Arabidopsis* Medium/Long-Chain-Length Prenyl Pyrophosphate Synthase," Plant Physiology, Mar. 2011, 155(3):1079-1090.

Ilmen, M. et al. "Regulation of Cellulase Gene Expression in the Filamentous Fungus *Trichoderma reesei*," Appl. Environ. Microbiol. Apr. 1997, 63(4):1298-1306.

Innis, M.A. et al. (Apr. 5, 1985). "Expression, Glycosylation, and Secretion of an *Aspergillus glucoamylase* by *Saccharomyces cerevisiae*," Science 228:21-26.

International Search Report mailed on Jan. 7, 2013 for PCT Patent Application No. PCT/US2012/049646, filed on Aug. 3, 2012, 4 pages.

Iwakura, M. et al. "Studies on Regulatory Functions of Malic Enzymes," J. Biochem. 1979, 85:1355-1365.

Jones, et al. "Sandalwood Fragrance Biosynthesis Involves Sesquiterpene Synthase of both the Terpene Synthase (TPS)-a and TPS-b Subfamilies, including Santalene Synthases," J Biol Chem. 286(20):17445-17454, May 20, 2011.

Kakuda, et al. "Identification and Characterization of the ackA (Acetate Kinase A)-pta (Phosphotransacetylase) Operon and Complementation Analysis of Acetate Utilization by an ackA-pta Deletion Mutant of *Escherichia coli*," J. Biochem. 1994, 116:916-922.

Keeling, et al. "Transcriptome Mining, Functional Characterization, and Phylogeny of a Large Terpene Synthase Gene Family in Spruce (*Picea* spp.)," BMC Plant Biol., Mar. 7, 2011, 11:43, 14 pages.

Kelly, J.M. et al. (1985). "Transformation of *Aspergillus niger* by the amdS Gene of *Asperfillus nidulans*," The EMBO Journal 4(2):475-479.

Garms, S. et al. (2010, e-pub. Jul. 20, 2010). "A multiproduct terpene synthase from *Medicago truncatula* Generates Cadalane Sesquiterpenes via Two Different Mechanisms," J Org Chem. 75(16):5590-5600.

Kumeta et al. "Characterization of δ-Guaiene Synthases from Cultured Cells of *Aquilaria*, Responsible for the Formation of the Sesquiterpenes in Agarwood," *Plant Physiol.* Dec. 2010, 154(4):1998-2007.

Kuzma, J. et al. (1995). "Bacteria Produce the Volatile Hydrocarbon Isoprene," *Curr Microbiology* 30:97-103.

Linko, et al. "Simultaneous liquefaction, saccharification, and lactic acid fermentation on barley starch," *Enzyme Microb. Technol.* 19:118-123 (1996).

Martin, et al. "Functional Annotation, Genome Organization and Phylogeny of the Grapevine (*Vitis vinifera*) Terpene Synthase Gene Family Based on Genome Assembly, FLcDNA Cloning, and Enzyme Assays," BMC Plant Biol.,Oct. 21, 2010;10:226, 22 pages.

Maurus, et al., "Insights into the Evolution of Allosteric Properties. The NADH Binding Site of Hexameric Type II Citrate Synthases," Biochemistry, 2003, 42:5555-5565.

McAuliffe, J. et al. "Bioprocess for the conversion of carbohydrates into bioisoprene," presented at the 239th National Meeting of the American Chemical Society, Division of Carbohydrate Chemistry, Mar. 21-25, 2010, San Francisco, CA, CARB 104, p. 65-66, three pages. Internet Citation, [Online] Mar. 21, 2010, Retrieved from the Internet: URL:http://carb.sites.acs.org/pdfs/ACS%20CARB%20Program/CARB%20program%20and%20abstract Spring2010.pdf032010>[retrieved on Dec. 15, 2011].

Medve, et al. "Ion-exchange chromatographic purifiation and quantitative analysis of *Trichoderma reesei* cellulases cellobiohydrolase I, II and endoglucanase II by fast protein liquid chromatography," J. Chromatography A 808:153-165 (1998).

Mercier, et al., "Kinetics of Lactic Acid Fermentation on Glucose and Corn by *Lactobacillus amylophilus*," *J. Chem. Tech. Biotechnol.* 55:111-121 (1992).

Miller, B. et al. (2001). "First Isolation of an Isoprene Synthase Gene from Poplar and Successful Expression of the Gene in *Escherichia coli*," Planta 213:483-487.

Ner, et al. "Complete Sequence of the glt A Gene Encoding Citrate Synthase in *Escherichia coli*," Biochemistry, 22(23):5243-5249 (Nov. 8, 1983).

Nevalainen, et al. "The Molecular Biology of Trichoderma and its Application to the Expression of Both Homologous and Heterologous Genes," Chapter 6 in Molecular Industrial Mycology, Eds. Leong and Berka, Marcel Dekker Inc., NY (1992) pp. 129-148.

Nunberg, J.H. et al. (Nov. 1984). "Molecular Cloning and Characterization of the Glucoamylase Gene of *Aspergillus awamori*," Mol. Cell. Biol. 4(11):2306-2315.

Ogasawara, H. et al. "PdhR (Pyruvate Dehydrogenase Complex Regulator) Controls the Respiratory Electron Transport System in *Escherichia coli*," *Journal of Bacteriology*, Aug. 2007, 189(15):5534-5541.

Oh, M-K. et al. (Apr. 12, 2002). "Global Expression Profiling of Acetate-Grown *Escherichia coli*," The Journal of Biological Chemistry 277(15):13175-13183.

Olofsson, K. et al. "A short review on SSF a an interesting process option for ethanol production from lignocellulosic feedstocks," Biotechnology for Biofuels. Biomed Central Ltd. GB, 1(1):7, May 1, 2008, 14 pages.

Penttila, M. et al. (1987). "A Versatile Transformation System for the Cellulolytic Filamentous Fungus *Trichoderma reesei*," Gene 61:155-164.

Pourquie, J. et al., "Scale up of cellulase production and utilization," Biochemistry and Genetics of Cellulose Degradation, Academic Press, pp. 71-86 (1988).

Riis, V. et al. (1996). "Investigations into the Toxicity of Persistent Fractions of Mineral Oils," *Chemosphere* 32(7):1435-1443.

Sanchez, et al. "Novel Pathway Engineering Design of the Anaerobic Central Metabolic Pathway in *Escherichia coli* to Increase Succinate Yield and Productivity," Metab. Eng., 2005, 7:229-239.

Sheir-Neiss, G. et al. (Jul. 1984). "Characterization of the Secreted Ceullulases of *Trichoderma ressei* Wild Type and Mutants During Controlled Fermentations," Appl. Microbiol. Biotechnol. 20(1):46-53.

Sharkey et al. "Evolution of the Isoprene Biosynthetic Pathway in Kudzu," Plant Physiology 137:700-712, (Feb. 2005).

Shimizu, et al., "Phosphotransacetylase of *Escherichia Coli* B, Purification and Properties," Biochim. Biophys. Acta, 1969, 191:550-558.

Silver, G.M. et al. (1991). "Enzymatic Synthesis of Isoprene from Dimethylallyl Diphosphate in Aspen Leaf Extracts," *Plant Physiology* 97:1588-1591.

(56) References Cited

OTHER PUBLICATIONS

Stokell, D.J. et al. (Sep. 12, 2003). "Probing the Roles of Key Residues in the Unique Regulatory NADH Binding Site of Type II Citrate Synthase of *Escherichia coli*," the Journal of Biological Chemistry 278(37):35435-35443.

Svensson, et al. The complete amino acid sequence of the glycoprotein, glucoamylase G1, from *Aspergillus niger*, Carlsberg Res. Commun. 48:529-544 (1983).

Tilbeurgh, et al. "Separation of endo- and exo-type cellulases using a new affinity chromatography method," *FEBS Letters* 169(2):215-218, Apr. 1984.

Tomaz, C.T. et al. (1999). "Studies on the chromatographic fractionation of *Trichoderma reesei* cellulases by hydrophobic interaction," *Journal of Chromatography A* 865:123-128.

Tsai, et al. "An integrated bioconversion process for production of L-Lactic acid from starchy potato feedstocks," *Appl. Biochem. Biotechnol.* 70-72: 417-428 (1998).

Underwood, S.A. et al. (Mar. 2002). "Flux through Citrate Synthase Limits the Growth of Ethanologenic *Scherichia coli* KO11 during Xylose Fermentation," *Appl. Environ. Microbiol.* 68(3):1071-1081.

Van Den Hondel, C.A.M.J.J. et al. (1991). "Heterologous Gene Expression in Filamentous Fungi," Chapter 18 in *More Gene Manipulations in Fungi*, Bennet, J.W. et al. eds., Academic.Press, Inc.: San Diego, CA, pp. 396-428.

Van Tilbeurgh, H. et al. (Apr. 1984). "Separation of endo- and exo-type cellulases using a new affinity chromatography method," FEBS Letters 169(2):215-218.

Wagner, W.P. et al. (Aug. 1999). "Three Distinct Phases of Isoprene Formation During Growth and Sporulation of *Bacillus subtilis*," *Journal of Bacteriology* 181(15):4700-4703.

Ward, M. et al. (Aug. 1993). "Use of *Aspergillus* Overproducing Mutants, Cured for Intergrated Plasmid, to Overproduce Heterologous Proteins," Appl. Microbiol. Biotechnol. 39(6):738-743.

Wiegand, et al. "Citrate Synthase: Structure, Control, and Mechanism," Ann. Rev. Biophys. Biophys. Chem. 1986, 15:97-117.

Wolfe, A.J. "The Acetate Switch," Microb. Mol. Biol. Rev., Mar. 2005, 69:12-50.

Xue, J. et al. (Apr. 2011). "Enhancing Isoprene Production by Genetic Modification of the 1-Deoxy-D-Xylulose-5-Phosphate Pathway in *Bacillus subtilis*," *Applied and Environmental Microbiology* 77(7):2399-2405.

Zhang, D.X. et al. (1991). "Direct Fermentation of Starch to Lactic Acid by *Lactobacillus amylovorus*," *Biotechnology Letters* 13(10):733-738.

Zhang, X. et al. (2007). "Production of L-alanine by metabolically engineered *Escherichia coli*," *Appl. Microbiol. Biotechnol.* 77:355-366.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22)13010-13016.

Non-Final Office Action mailed on Jun. 18, 2013 for U.S. Appl. No. 13/204,612, filed Aug. 5, 2011, 10 pages.

Response to Non-Final Office Action submitted to the U.S. Patent and Trademark Office on Oct. 18, 2013 for U.S. Appl. No. 13/204,612, filed Aug. 5, 2011, 15 pages.

Final Office Action mailed on Nov. 19, 2013 for U.S. Appl. No. 13/204,612, filed Aug. 5, 2011, 19 pages.

International Search Report mailed on Jan. 12, 2012 for PCT Patent Application No. PCT/US2011/046862, filed on Aug. 5, 2011, 4 pages.

Written Opinion mailed on Jan. 12, 2012 for PCT Patent Application No. PCT/US2011/046862, filed on Aug. 5, 2011, 7 pages.

European Communication mailed on Mar. 19, 2013 for EP Patent Application No. 11749630.7, filed on Aug. 5, 2011, 2 pages.

Response to the European Communication submitted to the European Patent Office on Sep. 23, 2013 for EP Patent Application No. 11749630.7, filed on Aug. 5, 2011, 15 pages.

Written Opinion mailed on Jan. 7, 2013 for PCT Patent Application No. PCT/US2012/049646, filed on Aug. 3, 2012, 5 pages.

European Communication mailed on Mar. 12, 2014 for EP Patent Application No. 12750654.1, filed on Aug. 3, 2012, 2 pages.

U.S. Appl. No. 14/218,720, filed Mar. 18, 2014 by Bergsma et al. (Copy not attached).

\* cited by examiner

PRODUCTION OF ISOPRENOIDS UNDER NEUTRAL PH CONDITIONS

CROSS-REFERENCE TO RELATED APPLICATIONS

This application claims the benefit of U.S. Provisional Application No. 61/515,830, filed Aug. 5, 2011, the disclosures of which are incorporated herein by reference in their entirety.

INCORPORATION BY REFERENCE

The Sequence Listing submitted in an ASCII text file, in accordance with 37 C.F.R. §1.821(c) and (e), is incorporated by herein by reference. The text file name is "246252007300_Sequence_Listing.txt", the date of creation of the text file is Aug. 2, 2012, and the size of the ASCII text file in bytes is 39,981.

FIELD OF THE INVENTION

Glucoamylases capable of effectively hydrolyzing a starch substrate at a pH in the range of 5.0 to 8.0 are useful in simultaneous saccharification and fermentation (SSF) to produce a product, such as isoprenoid precursors and isoprenoids.

BACKGROUND

Industrial fermentations predominately use glucose as a feedstock for the production of a multitude of proteins, enzymes, alcohols, and other chemical end products. Typically, glucose is the product of starch processing, which is conventionally a two-step, enzymatic process that catalyzes the breakdown of starch, involving liquefaction and saccharification. During liquefaction, insoluble granular starch is slurried in water, gelatinized with heat, and hydrolyzed by a thermostable alpha-amylase. During saccharification, the soluble dextrins produced in liquefaction are further hydrolyzed by glucoamylases.

Glucoamylases are exo-acting carbohydrases, capable of hydrolyzing both the linear and branched glucosidic linkages of starch (e.g., amylose and amylopectin). Commercially, glucoamylases are typically used in the acidic pH ranges (pH less than 5.0) to produce fermentable sugars from the enzyme liquefied starch substrate. The fermentable sugars, e.g., low molecular weight sugars, such as glucose, may then be converted to fructose by other enzymes (e.g., glucose isomerases); crystallized; or used in fermentations to produce numerous end products (e.g., alcohols, monosodium glutamate, succinic acid, vitamins, amino acids, 1,3-propanediol, and lactic acid).

A system that combines (1) saccharification and (2) fermentation is known as simultaneous saccharification and fermentation (SSF). SSF replaces the classical double-step fermentation, i.e., production of fermentable sugars first and then conducting the fermentation process for producing the end product. In SSF, an inoculum can be added along with the starch hydrolyzing enzymes to concurrently saccharify a starch substrate and convert the saccharification products (i.e., fermentable sugars) to the desired end product. The inoculum is typically a microorganism capable of producing the end product. In addition to its various advantages, SSF is particularly promising where a high concentration substrate is present in a low reactor volume.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

What is needed is a simple, efficient method of producing isoprenoids in commercial quantities.

Throughout this specification, references are made to publications (e.g., scientific articles), patent applications, patents, etc., all of which are herein incorporated by reference in their entirety.

BRIEF SUMMARY OF THE INVENTION

The invention provides, inter alia, for methods, compositions and systems for production of isoprenoid precursors and/or isoprenoids by a simultaneous saccharification and fermentation (SSF) process. The method takes advantage of the unique properties of certain glucoamylases. Glucoamylases such as *Humicola grisea* glucoamylase (HgGA), *Trichoderma reesei* glucoamylase (TrGA), and *Rhizopus* sp. glucoamylase (RhGA) display different pH profiles from other known glucoamylases, such as glucoamylases (GAs) from *Aspergillus niger* (AnGA) and *Talaromyces emersonii* (TeGA). At a pH of 6.0 or above, both HgGA and TrGA retain at least 50% of the activity relative to the maximum activity at pH 4.25 or pH 3.75, respectively. These glucoamylases are capable of saccharifying a starch substrate effectively at a pH in the range of 5.0 to 8.0, where cells (e.g., bacterial cells) can efficiently ferment the saccharified starch to isoprenoids. This property enables HgGA and TrGA to be used in SSF to produce isoprenoids compositions from a starch substrate in commercial quantities.

Accordingly, in one aspect of the invention, the invention provides for method for producing an isoprenoid precursor or isoprenoid comprising culturing a host cell, which comprises a heterologous nucleic acid encoding an polyprenyl pyrophosphate synthase polypeptide, and saccharifying and fermenting a starch substrate under simultaneous saccharification and fermentation (SSF) conditions in the presence of a glucoamylase, wherein the saccharification and fermentation are performed at pH 5.0 to 8.0, wherein the glucoamylase possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent *Rhizopus* sp. glucoamylase (RhGA) comprising SEQ ID NO: 9, and a variant thereof, and wherein the variant has at least 99% sequence identity to the parent glucoamylase.

In any of the aspects herein, the isoprenoid is selected from group consisting of monoterpenes, diterpenes, triterpenes, tetraterpenes, sequiterpene, and polyterpene. In one aspect, the isoprenoid is a sesquiterpene. In another aspect, the isoprenoid is selected from the group consisting of abietadiene, amorphadiene, carene, farnesene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In one embodiment, the variant has one amino acid modification compared to the parent glucoamylase. In another embodiment, the HgGA is SEQ ID NO: 3. In another embodiment, the HgGA is produced from a *Trichoderma reesei* host cell. In another embodiment, the TrGA is SEQ ID No: 6. In another embodiment, the RhGA is SEQ ID NO: 9.

In another embodiment, the SSF is carried out at pH 6.0 to 7.5. In another embodiment, the SSF process is carried out at pH 7.0 to 7.5. In another embodiment, the SSF is performed at a temperature in a range of about 30° C. to about 60° C. In another embodiment, the SSF is performed at a temperature in a range of about 40° C. to about 60° C. In another embodiment, the starch substrate is about 15% to 50% dry solid (DS). In another embodiment, the starch substrate is about 15% to 30% dry solid (DS). In another embodiment, the starch substrate is about 15% to 25% dry solid (DS). In another embodiment, the starch substrate is granular starch or liquefied starch. In another embodiment, the glucoamylase is dosed at a range of about 0.1 to about 2.0 GAU per gram of dry substance starch. In another embodiment, the glucoamylase is dosed at a range of about 0.2 to about 1.0 GAU per gram of dry substance starch. In another embodiment, the glucoamylase is dosed at a range of about 0.5 to 1.0 GAU per gram of dry substance starch. In another embodiment, alpha-amylase is further added to any of the embodiments herein. In another embodiment, the alpha-amylase is from a *Bacillus* species, or a variant thereof. In another embodiment, the alpha-amylase is a *Bacillus subtilis* alpha-amylase (AmyE), a *Bacillus amyloliquefaciens* alpha-amylase, a *Bacillus licheniformis* alpha-amylase, a *Bacillus stearothermophilus* alpha-amylase, or a variant thereof. In another embodiment, the starch substrate is from corn, wheat, rye, barley, sorghum, cassava, tapioca, and any combination thereof.

In another embodiment, the heterologous nucleic acid is operably linked to a promoter and wherein the production of isoprenoids by the cells is greater than about 5 g/L. In another embodiment, the host cells further comprise (i) one or more non-modified nucleic acids encoding feedback-resistant mevalonate kinase polypeptides or (ii) one or more additional copies of an endogenous nucleic acid encoding a feedback-resistant mevalonate kinase polypeptide. In another embodiment, the feedback-resistant mevalonate kinase is archaeal mevalonate kinase. In another embodiment, the mevalonate kinase polypeptide is selected from the group consisting of *M. mazei*, *Lactobacillus* mevalonate kinase polypeptide, *Lactobacillus sakei* mevalonate kinase polypeptide, yeast mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *M. Burtonii* mevalonate kinase polypeptide. In another embodiment, the host cells further comprise one or more heterologous nucleic acid encoding a mevalonate (MVA) pathway polypeptide and/or a DXP pathway polypeptide. In another embodiment, the host cell is selected from the group of bacterial cells, fungal cells, algal cells, plant cells, or cyanobacterial cells. In another embodiment, the bacterial cells are selected from the group consisting of gram-positive bacterial cells, gram-negative bacterial cells, *E. coli*, *P. citrea*, *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp., *P. alcaligenes*, and *C. glutanicum* cells. In another embodiment, the fungal cells are selected from the group consisting of *Aspergillus*, yeast, *Trichoderma*, or *Yarrowia* cells. In another embodiment, the yeast is *Saccharomyces* sp., *Schizosaccharomyces* sp., *Pichia* sp., *Candida* sp. or *Y. lipolytica* cells. In another embodiment, the fungal cells are selected from the group consisting of *A. oryzae*, *A. niger*, *S. cerevisiae*, *S. pombe*, *T. reesei*, *H. insolens*, *H. lanuginose*, *H. grisea*, *C. lucknowense*, *A. oryzae*, *A. niger*, *A sojae*, *A. japonicus*, *A. nidulans*, *A. aculeatus*, *A. awamori*, *F. roseum*, *F. graminum F. cerealis*, *F. oxysporuim*, *F. venenatum*, *N. crassa*, *M. miehei*, *T. viride*, *F. oxysporum*, and *F. solan* cells.

In another embodiment, the plant cells are selected from the group consisting of: the family Fabaceae, the Faboideae subfamily, kudzu, poplar, *Populus alba×tremula*, *Populus alba*, aspen, *Populus tremuloides*, and *Quercus robur* cells. In another embodiment, the algal cells are selected from the group consisting of: green algae, red algae, glaucophytes, chlorarachniophytes, euglenids, chromista, and dinoflagellates.

In another embodiment, the invention provides for methods of processing starch comprising saccharifying a starch substrate to fermentable sugars at pH 5.0 to 8.0 in the presence of glucoamylase and at least one other enzyme, wherein the glucoamylase possesses at least 50% activity at pH 6.0 or above relative to its maximum activity, wherein the glucoamylase is selected from the group consisting of *Humicola grisea* glucoamylase (HgGA) comprising SEQ ID NO: 3, *Trichoderma reesei* glucoamylase (TrGA) comprising SEQ ID NO: 6, *Rhizopus* sp. glucoamylase (RhGA) comprising SEQ ID NO: 9, and a variant thereof, and wherein the variant has at least 99% sequence identity to a parent glucoamylase, and wherein the other enzyme is selected from the group consisting of proteases, pullulanases, isoamylases, cellulases, hemicellulases, xylanases, cyclodextrin glycotransferases, lipases, phytases, laccases, oxidases, esterases, cutinases, xylanases, and alpha-glucosidases.

In another embodiment, the invention provides for methods of processing starch comprising saccharifying a starch substrate to fermentable sugars at pH 5.0 to 8.0 in the presence of glucoamylase and at least one other non-starch polysaccharide hydrolyzing enzymes, wherein the glucoamylase possesses at least 50% activity at pH 6.0 or above relative to its maximum activity, wherein the glucoamylase is selected from the group consisting of *Humicola grisea* glucoamylase (HgGA) comprising SEQ ID NO: 3, *Trichoderma reesei* glucoamylase (TrGA) comprising SEQ ID NO: 6, *Rhizopus* sp. glucoamylase (RhGA) comprising SEQ ID NO: 9, and a variant thereof, and wherein the variant has at least 99% sequence identity to a parent glucoamylase, and wherein the non-starch polysaccharide hydrolyzing enzymes is selected from the group consisting of cellulases, hemicellulases and pectinases.

In another aspect, the invention provide for systems for producing an isoprenoid comprising (i) a bioreactor within which saccharification and fermentation are performed at pH 5.0 to 8.0; (ii) a host cell comprising a heterologous nucleic acid encoding an polyprenyl pyrophosphate synthase polypeptide; (iii) a glucoamylase that possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent

*Rhizopus* p. glucoamylase (RhGA) comprising SEQ ID NO: 9, and a variant thereof, and wherein the variant has at least 99% sequence identity to the parent glucoamylase.

In another aspect, the invention provides for methods for producing an isoprenoid comprising culturing a host cell, which comprises a heterologous nucleic acid encoding an polyprenyl pyrophosphate synthase polypeptide, and saccharifying and fermenting a starch substrate under simultaneous saccharification and fermentation (SSF) conditions in the presence of a glucoamylase and at least one other enzyme, wherein the glucoamylase possesses at least 50% activity at pH 6.0 or above relative to its maximum activity, wherein the glucoamylase is selected from the group consisting of *Humicola grisea* glucoamylase (HgGA) comprising SEQ ID NO: 3, *Trichoderma reesei* glucoamylase (TrGA) comprising SEQ ID NO: 6, *Rhizopus* sp. glucoamylase (RhGA) comprising SEQ ID NO: 9, and a variant thereof, and wherein the variant has at least 99% sequence identity to a parent glucoamylase, and wherein the other enzyme is selected from the group consisting of proteases, pullulanases, isoamylases, cellulases, hemicellulases, xylanases, cyclodextrin glycotransferases, lipases, phytases, laccases, oxidases, esterases, cutinases, xylanases, and alpha-glucosidases.

In another aspect, the invention provides for methods for producing an isoprenoid comprising culturing a host cell, which comprises a heterologous nucleic acid encoding an polyprenyl pyrophosphate synthase polypeptide, and saccharifying and fermenting a starch substrate under simultaneous saccharification and fermentation (SSF) conditions in the presence of a glucoamylase and at least one other non-starch polysaccharide hydrolyzing enzymes, wherein the glucoamylase possesses at least 50% activity at pH 6.0 or above relative to its maximum activity, wherein the glucoamylase is selected from the group consisting of *Humicola* grisea glucoamylase (HgGA) comprising SEQ ID NO: 3, *Trichoderma reesei* glucoamylase (TrGA) comprising SEQ ID NO: 6, *Rhizopus* sp. glucoamylase (RhGA) comprising SEQ ID NO: 9, and a variant thereof, and wherein the variant has at least 99% sequence identity to a parent glucoamylase, and wherein the non-starch polysaccharide hydrolyzing enzymes is selected from the group consisting of cellulases, hemicellulases and pectinases.

In another aspect, the invention provides for compositions of isoprenoids produced by the methods and/or systems described herein.

BRIEF DESCRIPTION OF THE DRAWINGS

The accompanying drawings are incorporated into the specification and provide non-limiting illustrations of various embodiments. In the drawings.

$$\text{isoprene titer} = \int (\text{Instantaneous isoprene production rate, g/L/hr}) dt$$

from $t$ $= 0$ to 20 hours $[=]$ g/L broth (total isoprene produced over the time course per liter broth, g/L broth)

Figure 6:
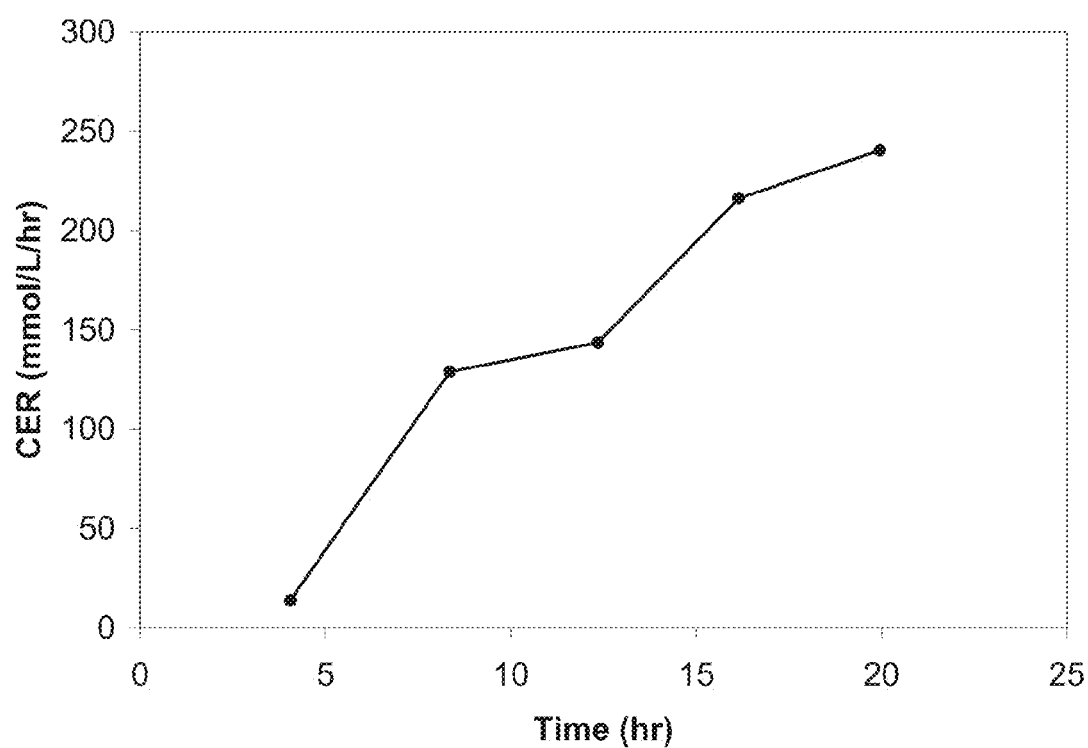

FIG. 6 depicts the time course of the carbon dioxide evolution rate (CER) or metabolic activity profile. Isoprene production was achieved by the simultaneous saccharification and fermentation process with TrGA and an alpha-amylase as described in Example 8.2.

Figure 7:
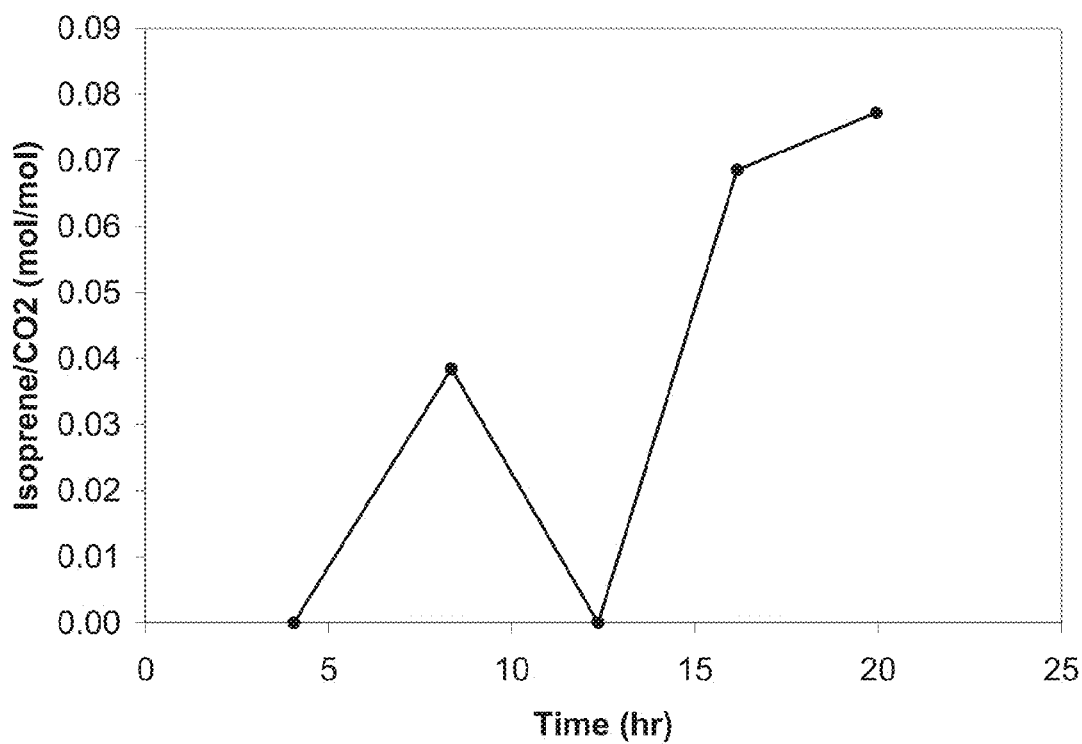

FIG. 7 depicts the time course of the isoprene to carbon dioxide ratio in the gas stream exiting the bioreactor. The isoprene to carbon dioxide ratio is an indicator of product yield. Isoprene production was achieved by the simultaneous saccharification and fermentation process with TrGA and an alpha-amylase as described in Example 8.2.

Figure 8:
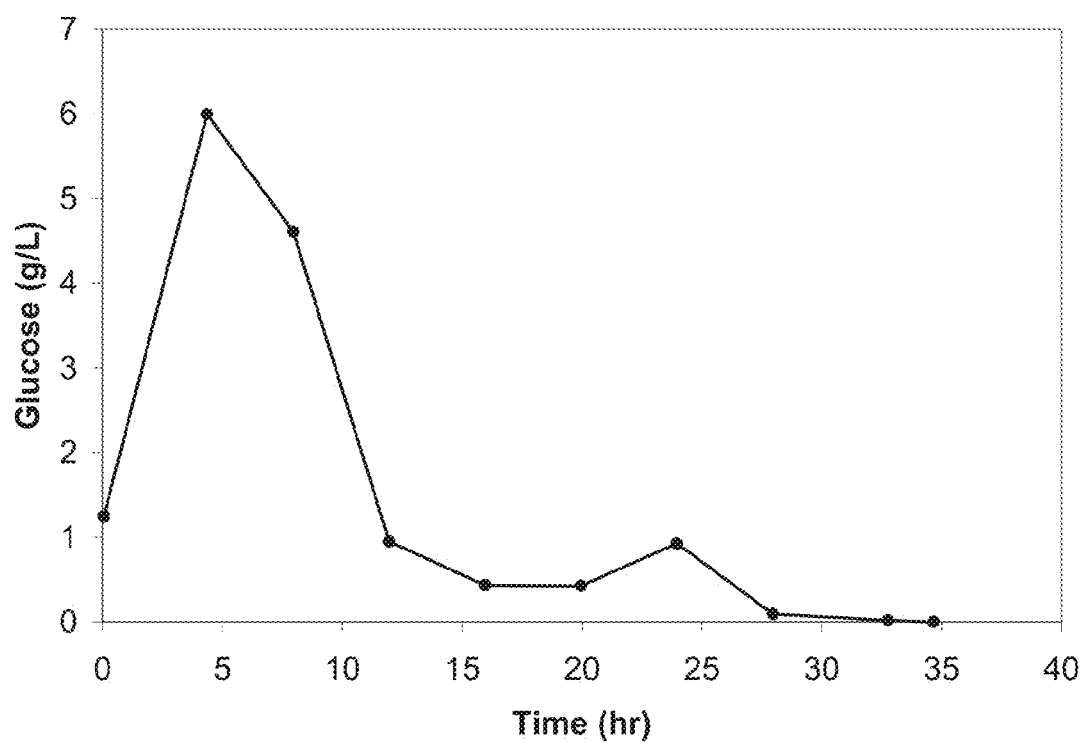

FIG. 8 depicts the time course of accumulated glucose levels during isoprene production. The simultaneous saccharification and fermentation process was carried with HgGA as described in Example 8.3.

Figure 9:
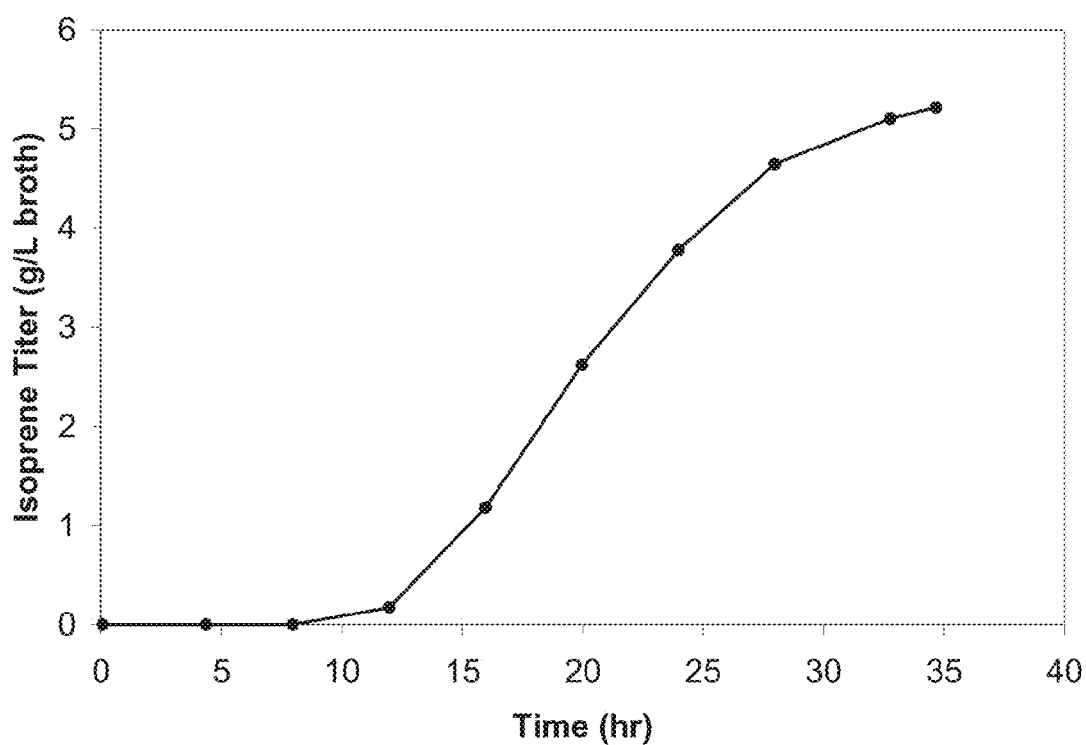

FIG. 9 depicts the time course of isoprene titer. Isoprene production was achieved by the simultaneous saccharification and fermentation process with HgGA as described in Example 8.3. The titer is defined as the amount of isoprene produced per liter of fermentation broth. The equation for calculating isoprene titer:

$$\text{isoprene titer} = \int (\text{Instantaneous isoprene production rate, g/L/hr}) dt$$

from $t$ $= 0$ to 20 hours $[=]$ g/L broth.

Figure 10:
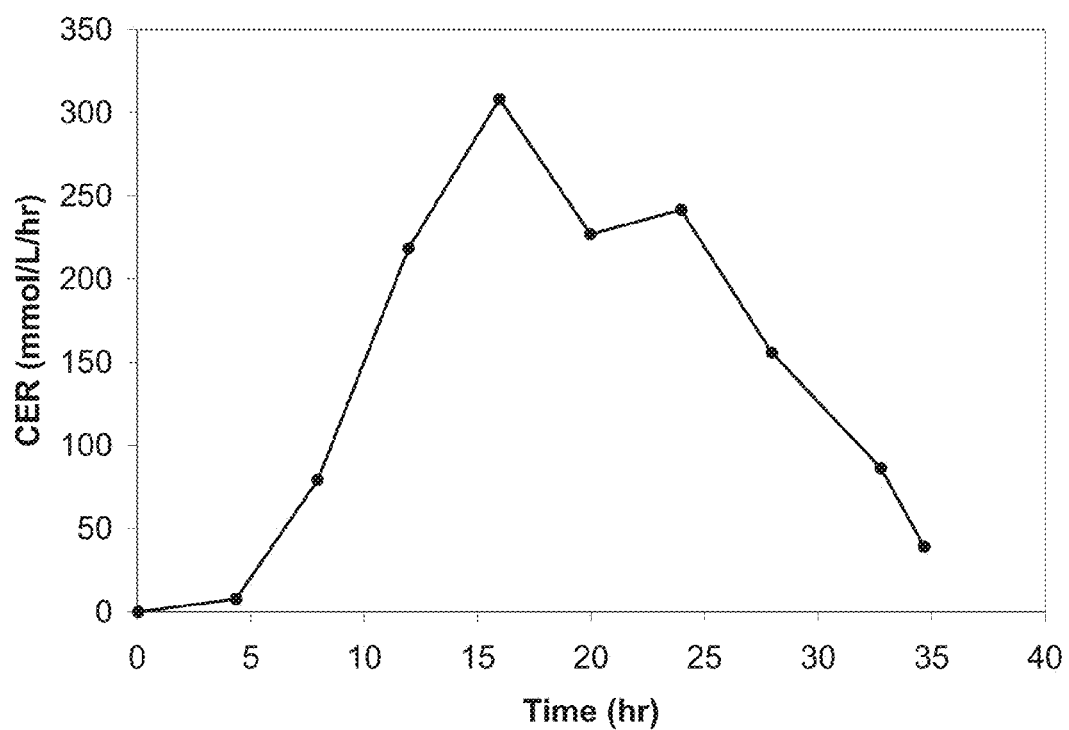

FIG. 10 depicts the time course of the carbon dioxide evolution rate (CER) or metabolic activity profile. Isoprene production was achieved by the simultaneous saccharification and fermentation process with HgGA as described in Example 8.3.

Figure 11:
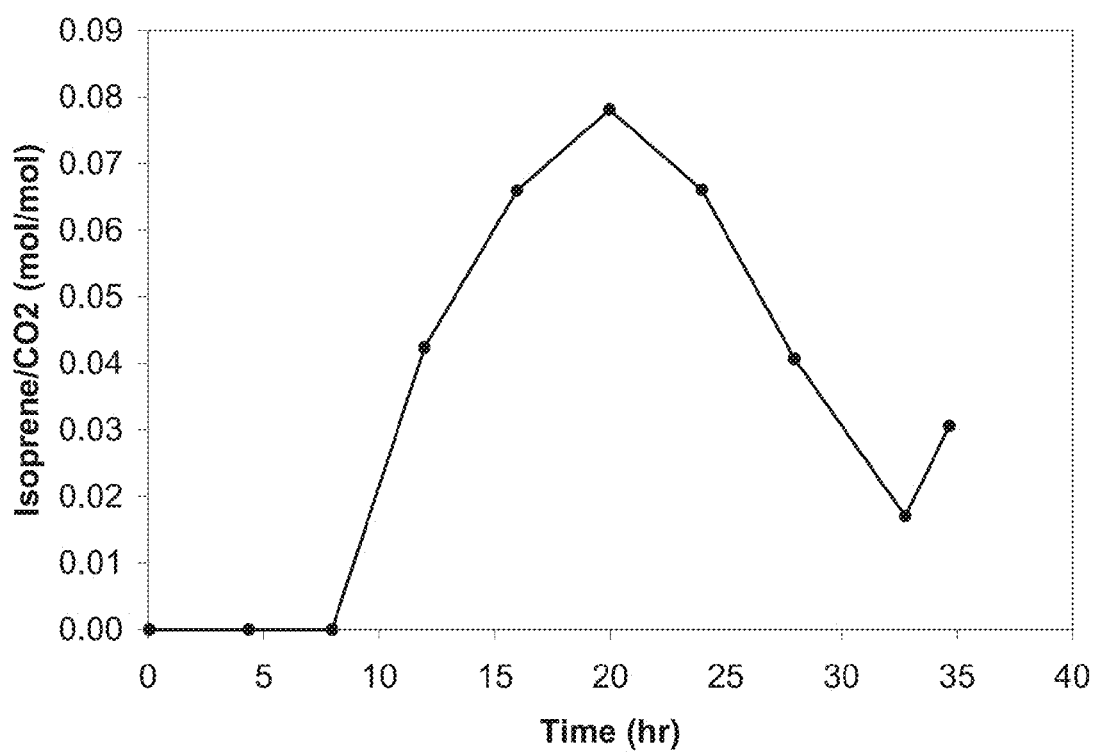

FIG. 11 depicts the time course of the isoprene to carbon dioxide ratio in the gas stream exiting the bioreactor. The isoprene to carbon dioxide ratio is an indicator of product yield. Isoprene production was achieved by the simultaneous saccharification and fermentation process with HgGA as described in Example 8.3.

DETAILED DESCRIPTION

The invention provides for methods and systems of producing isoprenoid precursor molecules and/or isoprenoids using simultaneous saccharification and fermentation process and glucoamylases at neutral pH.

In one aspect, the present disclosure relates to the use of glucoamylases capable of effectively saccharifying a starch substrate at a neutral pH, for example, between pH 5.0 and 8.0, to provide an energy source for the biological production of isoprenoid precursor molecules and/or isoprenoids. At a pH of 6.0 or above, the glucoamylases of the disclosed method retains at least about 50% activity relative to the maximum activity. The glucoamylases having these properties include, for example, HgGA, TrGA, and RhGA.

In some aspects, the embodiments of the present disclosure rely on routine techniques and methods used in the field of genetic engineering and molecular biology. The following resources include descriptions of general methodology useful in accordance with the invention: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the representative methods and materials are described. Numeric ranges are inclusive of the numbers defining the range. The headings provided herein are not limitations of the various aspects or embodiments, which can be had by reference to the specification as a whole.

Definitions and Abbreviations

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., mevalonate (mevolonic acid (MVA), isopentenyl pyrophosphate (IPP) and dimethylallyl diphosphate (DMAPP).

By "heterologous nucleic acid" is meant a nucleic acid whose nucleic acid sequence is not identical to that of another nucleic acid naturally found in the same host cell.

As used herein, "nucleotide sequence" or "nucleic acid sequence" refers to a sequence of genomic, synthetic, or recombinant origin and may be double-stranded or single-stranded, whether representing the sense or anti-sense strand. As used herein, the term "nucleic acid" may refer to genomic DNA, cDNA, synthetic DNA, or RNA. The residues of a nucleic acid may contain any of the chemically modifications commonly known and used in the art.

As used herein, "polypeptides" includes polypeptides, proteins, peptides, fragments of polypeptides, and fusion polypeptides. In some embodiments, the fusion polypeptide includes part or all of a first polypeptide (e.g., an polyprenyl pyrophosphate synthase, DXS, IDI, or MVA pathway polypeptide or catalytically active fragment thereof) and may optionally include part or all of a second polypeptide (e.g., a peptide that facilitates purification or detection of the fusion polypeptide, such as a His-tag).

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

"Isolated" means that the material is at least substantially free from at least one other component that the material is naturally associated and found in nature.

"Purified" means that the material is in a relatively pure state, e.g., at least about 90% pure, at least about 95% pure, at least about 98% pure, or at least about 99% pure.

"Oligosaccharide" means a carbohydrate molecule composed of 3-20 monosaccharides.

As used herein, "transformed cell" includes cells that have been transformed by use of recombinant DNA techniques. Transformation typically occurs by insertion of one or more nucleotide sequences into a cell. The inserted nucleotide sequence may be a heterologous nucleotide sequence, i.e., is a sequence that may not be natural to the cell that is to be transformed, such as a fusion protein.

As used herein, "starch" refers to any material comprised of the complex polysaccharide carbohydrates of plants, comprised of amylose and amylopectin with the formula $(C_6H_{10}O_5)_x$, wherein "X" can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

As used herein, "granular starch" refers to uncooked (raw) starch, which has not been subject to gelatinization.

As used herein, "starch gelatinization" means solubilization of a starch molecule to form a viscous suspension.

As used herein, "gelatinization temperature" refers to the lowest temperature at which gelatinization of a starch substrate occurs. The exact temperature depends upon the specific starch substrate and further may depend on the particular variety and the growth conditions of plant species from which the starch is obtained.

"DE" or "dextrose equivalent" is an industry standard for measuring the concentration of total reducing sugars, calculated as the percentage of the total solids that have been converted to reducing sugars. The granular starch that has not been hydrolyzed has a DE that is about zero (0), and D-glucose has a DE of about 100.

As used herein, "starch substrate" refers to granular starch or liquefied starch using refined starch, whole ground grains, or fractionated grains.

As used herein, "liquefied starch" refers to starch that has gone through solubilization process, for example, the conventional starch liquefaction process.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4+ (>DP4) denotes polymers with a degree of polymerization of greater than four.

As used herein, "fermentable sugars" refer to saccharides that are capable of being metabolized under fermentation conditions. These sugars typically refer to glucose, maltose, and maltotriose (DP1, DP2 and DP3).

As used herein, "total sugar content" refers to the total sugar content present in a starch composition.

As used herein, "ds" refers to dissolved solids in a solution. The term "dry solids content (DS)" refers to the total solids of a slurry in % on a dry weight basis. The term "slurry" refers to an aqueous mixture containing insoluble solids.

As used herein, "starch-liquefying enzyme" refers to an enzyme that catalyzes the hydrolysis or breakdown of granular starch. Exemplary starch liquefying enzymes include alpha-amylases (EC 3.2.1.1).

"Amylase" means an enzyme that is, among other things, capable of catalyzing the degradation of starch. For example, β-Amylases, α-glucosidases (EC 3.2.1.20; α-D-glucoside glucohydrolase), glucoamylase (EC 3.2.1.3; α-D-(14)-glucan glucohydrolase), and product-specific amylases can produce malto-oligosaccharides of a specific length from starch.

"Alpha-amylases (EC 3.2.1.1)" refer to endo-acting enzymes that cleave α-D-(1→4) O-glycosidic linkages within the starch molecule in a random fashion. In contrast, the exo-acting amylolytic enzymes, such as beta-amylases (EC 3.2.1.2; α-D-(1→4)-glucan maltohydrolase) and some product-specific amylases like maltogenic alpha-amylase (EC 3.2.1.133) cleave the starch molecule from the non-reducing end of the substrate. These enzymes have also been described as those effecting the exo- or endohydrolysis of 1,4-α-D-glucosidic linkages in polysaccharides containing 1,4-α-linked D-glucose units. Another term used to describe these enzymes is glycogenase. Exemplary enzymes include alpha-1,4-glucan 4-glucanohydrolase.

As used herein, "glucoamylases" refer to the amyloglucosidase class of enzymes (EC 3.2.1.3, glucoamylase, α-1,4-D-glucan glucohydrolase). These are exo-acting enzymes that release glucosyl residues from the non-reducing ends of amylose and/or amylopectin molecules. The enzymes are also capably of hydrolyzing α-1,6 and α-1,3 linkages, however, at much slower rates than the hydrolysis of α-1,4 linkages.

As used herein, the term "non-starch polysaccharide hydrolyzing enzymes" are enzymes capable of hydrolyzing complex carbohydrate polymers such as cellulose, hemicellulose, and pectin. For example, cellulases (endo and exo-glucanases, beta glucosidase) hemicellulases (xylanases) and pectinases are non-starch polysaccharide hydrolyzing enzymes.

Figure 1:
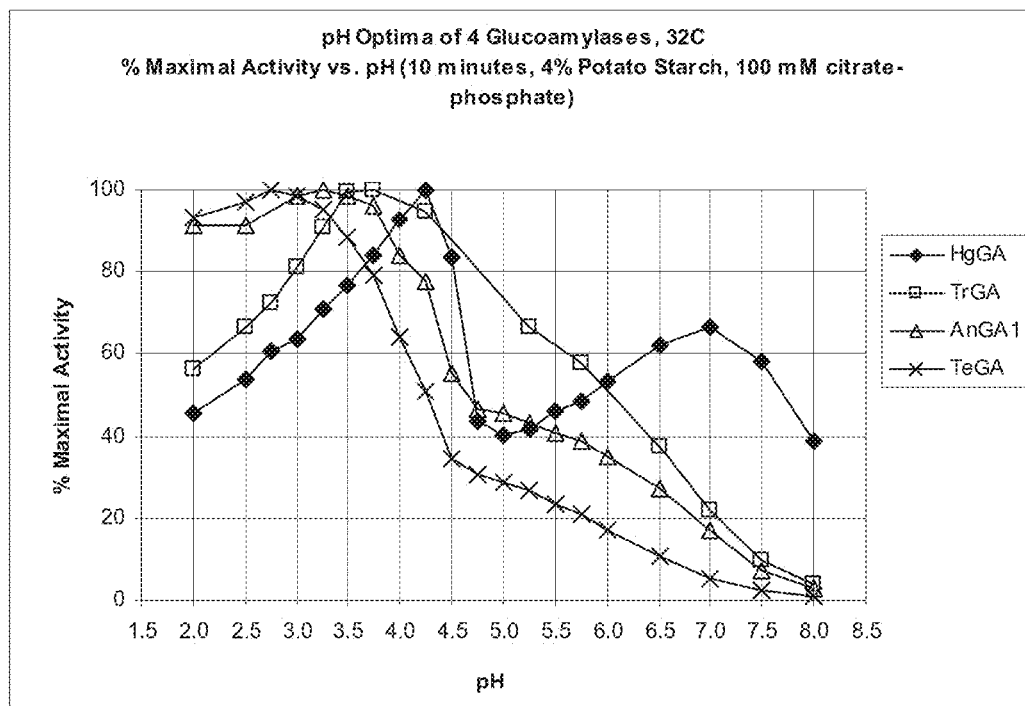
FIG. 1 depicts the pH profiles of HgGA, TrGA, AnGA, and TeGA, at 32° C. The pH profiles are presented as the percentage of the maximum activity under the saccharification conditions described in Example 1.

As used herein, "maximum activity" refers to the enzyme activity measured under the most favorable conditions, for example, at an optimum pH. As used herein, "optimum pH" refers to a pH value, under which the enzyme displays the highest activity with other conditions being equal. The "optimum pH" of HgGA and TrGA is shown in FIG. 1.

The phrase "mature form" of a protein or polypeptide refers to the final functional form of the protein or polypeptide. A mature form of a glucoamylase may lack a signal peptide and/or initiator methionine, for example. A mature form of a glucoamylase may be produced from its native host, for example, by endogenous expression. Alternatively, a mature form of a glucoamylase may be produced from a non-native host, for example, by exogenous expression. An exogenously expressed glucoamylase may have a varied glycosylation pattern compared to the endogenous expressed counterpart.

The term "parent" or "parent sequence" refers to a sequence that is native or naturally occurring.

As used herein, the terms "variant" is used in reference to glucoamylases that have some degree of amino acid sequence identity to a parent glucoamylase sequence. A variant is similar to a parent sequence, but has at least one substitution, deletion or insertion in their amino acid sequence that makes them different in sequence from a parent glucoamylase. In some cases, variants have been manipulated and/or engineered to include at least one substitution, deletion, or insertion in their amino acid sequence that makes them different in sequence from a parent. Additionally, a glucoamylase variant may retain the functional characteristics of the parent glucoamylase, e.g., maintaining a glucoamylase activity that is at least 50%, 60%, 70%, 80%, 90%, 95%, 98%, or 99% of that of the parent glucoamylase.

As used herein, "hydrolysis of starch" refers to the cleavage of glucosidic bonds with the addition of water molecules.

As used herein, "end product" or "desired end product" refers to a molecule or compound to which a starch substrate is converted into, by an enzyme and/or a microorganism.

As used herein, "contacting" or "admixing" refers to the placing of the respective enzyme(s) in sufficiently close proximity to the respective substrate to enable the enzyme(s) to convert the substrate to the end product. Those skilled in the art will recognize that mixing solutions of the enzyme with the respective substrates can affect contacting or admixing.

Abbreviations

The following abbreviations apply unless indicated otherwise:

AkAA *Aspergillus kawachii* alpha-amylase
AmyE *Bacillus subtilis* alpha-amylase
AmyL *Bacillus licheniformis* alpha-amylase
AmyR SPEZYME® XTRA amylase
AmyS *Geobacillus stearothermophilus* alpha-amylase
AnGA *Aspergillus niger* glucoamylase
BAA bacterial alpha-amylase
cDNA complementary DNA
CER carbon dioxide evolution rate
DE Dextrose Equivalent
DI distilled, deionized
DMAPP 3,3-dimethylallyl pyrophosphate
DNA deoxyribonucleic acid
DP3 degree of polymerization with three subunits
DPn degree of polymerization with n subunits
DS or ds dry solid
dss dry solid starch
DXS 1-deoxy-D-xylulose-5-phosphate synthase
EC enzyme commission for enzyme classification
g gram
gpm gallon per minute
GAU glucoamylase units
HGA *Humicola grisea* glucoamylase
HgGA *Humicola grisea* glucoamylase
HPLC high pressure liquid chromatography
IPTG isopropyl-beta-D-1-thiogalactopyranoside
kg kilogram
MEP methylerythritol phosphate
MOPS 3-(N-morpholino)propanesulfonic acid
MT metric ton MVA mevalonate
MW molecular weight
NCBI National Center for Biotechnology Information
nm nanometer
OD optical density
PCR polymerase chain reaction
PEG polyethylene glycol
pI isoelectric point
ppm parts per million
q.s. as much as suffices (quantum satis or quantum sufficit)
RhGA *Rhizopus* sp. glucoamylase
RNA ribonucleic acid
RO reverse osmosis
rpm revolutions per minute
slpm standard liters per minute
SSF simultaneous saccharification and fermentation
TeGA *Talaromyces emersonii* glucoamylase
TrGA *Trichoderma reesei* glucoamylase
w/v weight/volume
w/w weight/weight
wt wild-type
μL microliter Enzymes in Starch Processing Glucoamylase Having the Desired pH Profile Glucoamylases are produced by numerous strains of bacteria, fungi, yeast and plants. Many fungal glucoamylases are fungal enzymes that are extracellularly produced, for example from strains of *Aspergillus* (Svensson et al., *Carlsberg Res. Commun.* 48: 529-544 (1983); Boel et al., *EMBO J.* 3: 1097-1102 (1984); Hayashida et al., *Agric. Biol. Chem.* 53: 923-929 (1989); U.S. Pat. No. 5,024,941; U.S. Pat. No. 4,794,175 and WO 88/09795); *Talaromyces* (U.S. Pat. Nos. 4,247,637; 6,255,084; and 6,620,924); *Rhizopus* (Ashikari et al., *Agric. Biol. Chem.* 50: 957-964 (1986); Ashikari et al., *App. Microbio. Biotech.* 32: 129-133 (1989) and U.S. Pat. No. 4,863,864); *Humicola* (WO 05/052148 and U.S. Pat. No. 4,618,579); and *Mucor* (Houghton-Larsen et al., *Appl. Microbiol. Biotechnol.* 62: 210-217 (2003)). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States. In general, glucoamylases may be, and commonly are, used with alpha-amylases in starch hydrolyzing processes to hydrolyze starch to dextrins and then glucose. The glucose may then be converted to fructose by other enzymes (e.g., glucose isomerases); crystallized; or used in fermentations to produce numerous end products (e.g., ethanol, citric acid, succinic acid, ascorbic acid intermediates, glutamic acid, glycerol, 1,3-propanediol and lactic acid).

The embodiments of the present disclosure utilize a glucoamylase capable of effectively saccharifying a starch substrate at a neutral pH, for example, between pH 5.0 and 8.0, 5.5 and 7.5, 6.0 and 7.5, 6.5 and 7.5, or 7.0 and 7.5. At a pH of 6.0 or above, the glucoamylase retains at least about 50%, about 51%, about 52%, about 53%, about 54%, or about 55% of the activity relative to the maximum activity. The glucoamylases having the desired pH profile include, but are not limited to, *Humicola grisea* glucoamylase (HgGA), *Trichoderma reesei* glucoamylase (TrGA), and *Rhizopus* sp. glucoamylase (RhGA).

HgGA may be the glucoamylase comprising the amino acid sequence of SEQ ID NO: 3, which is described in detail in U.S. Pat. Nos. 4,618,579 and 7,262,041. This HgGA is also described as a granular starch hydrolyzing enzyme (GSHE), because it is capable of hydrolyzing starch in granular form. The genomic sequence coding the HgGA from *Humicola grisea* var. *thermoidea* is presented as SEQ ID NO: 1, which contains three putative introns (positions 233-307, 752-817, and 950-1006). The native HgGA from *Humicola grisea* var. *thermoidea* has the amino acid sequence of SEQ ID NO: 2, which includes a signal peptide containing 30 amino acid residues (positions 1 to 30 of SEQ ID NO: 2). Cleavage of the signal peptide results in the mature HgGA having the amino acid sequence of SEQ ID NO: 3. The embodiments of the present disclosure also include a HgGA produced from a *Trichoderma* host cell, e.g., a *Trichoderma reesei* cell. See U.S. Pat. No. 7,262,041.

A typical TrGA is the glucoamylase from *Trichoderma reesei* QM6a (ATCC, Accession No. 13631). This TrGA comprising the amino acid sequence of SEQ ID NO: 6, which is described in U.S. Pat. No. 7,413,879, for example. The cDNA sequence coding the TrGA from *Trichoderma reesei* QM6a is presented as SEQ ID NO: 4. The native TrGA has the amino acid sequence of SEQ ID NO: 5, which includes a signal peptide containing 33 amino acid residues (positions 1 to 33 of SEQ ID NO: 4). See id. Cleavage of the signal peptide results in the mature TrGA having the amino acid sequence of SEQ ID NO: 6. See id. The catalytic domain of TrGA is presented as SEQ ID NO: 7. See id. The embodiments of the present disclosure also include an endogenously expressed TrGA. See id.

RhGA may be the glucoamylase from *Rhizopus niveus* or *Rhizopus oryzae*. See U.S. Pat. Nos. 4,514,496 and 4,092,434. The native RhGA from *R. oryzae* has the amino acid sequence of SEQ ID NO: 8, which includes a signal peptide containing 25 amino acid residues (positions 1 to 25 of SEQ ID NO:8). Cleavage of the signal peptide results in the mature RhGA having the amino acid sequence of SEQ ID NO: 9. A typical RhGA may be the glucoamylase having trade names CU.CONC (Shin Nihon Chemicals, Japan) or M1 (Biocon India, Bangalore, India).

Structure and Function

The glucoamylase of the embodiment of the present disclosure may also be a variant of HgGA, TrGA, or RhGA. The variant has at least 99% sequence identity to the parent glucoamylase. In some embodiments, the variant has at least 98%, at least 97%, at least 96%, at least 95%, at least 94%, at least 93%, at least 92%, at least 91%, or at least 90% sequence identity to the parent glucoamylase. Optionally, the variant has one, two, three, four, five, or six amino acids modification compared to the mature form of the parent glucoamylase. In other embodiments, the variant has at least 98%, 97%, 96%, 95%, 94%, 93%, 92%, 91%, or 90% sequence identity to the parent glucoamylase. Optionally, the variant has more than six amino acids (e.g., 7, 8, 9, 10, 11, 12, 13, 14, 15, 20, 25, 30, 35, 40, 45, 50, 55, or 60) modification compared to the mature form of the parent glucoamylase. The variant possesses the desired pH profile and capability of saccharifying a starch substrate at a pH in the range of 5.0 to 8.0. In some embodiments, the variants may possess other improved properties, such as improved thermostability and improved specificity.

Glucoamylases consist of as many as three distinct structural domains, a catalytic domain of approximately 450 residues that is structurally conserved in all glucoamylases, generally followed by a linker region consisting of between 30 and 80 residues that are connected to a starch binding domain of approximately 100 residues. For example, TrGA has a catalytic domain having the amino acid sequence of SEQ ID NO: 7. The structure of the *Trichoderma reesei* glucoamylase (TrGA) with all three regions intact was determined to 1.8 Angstrom resolution. See WO 2009/048488 and WO 2009/048487. Using the determined coordinates, the structure was aligned with the coordinates of the catalytic domain of the glucoamylase from *Aspergillus awamori* strain X100 that was determined previously (Aleshin, A. E., Hoffman, C., Firsov, L. M., and Honzatko, R. B. Refined crystal structures of glucoamylase from *Aspergillus awamori* var. X100. *J. Mol. Biol.* 238: 575-591 (1994)). See id. The structure of the catalytic domains of TrGA and *Aspergillus awamori* glucoamylase overlap very closely, and it is possible to identify equivalent residues based on this structural superposition. See id. It is further believed that all glucoamylases share the basic structure. See id.

Given the well-known structure and function relationship of glucoamylases, glucoamylase variants having altered properties have been successfully created and characterized. The variants may display improved properties as compared to the parent glucoamylases. The improved properties may include, and are not limited to, increased thermostability and increased specific activity. For example, methods for making and characterizing TrGA variants with altered properties have been described in WO 2009/067218. Functional TrGA variants have been identified having one or more specific sequence modifications. Some TrGA variants, for example, have multiple sequence modifications. WO 2009/067218 discloses TrGA variants with six or more amino acid modifications, for example. These TrGA variants show at least as much activity as the parent TrGA, and in many cases show improved properties. It is expected that corresponding residue changes in HgGA and RhGA, for example, will yield variants with glucoamylase activity. The glucoamylase variants useful in the present methods have, at a pH of 6.0 or above, at least about 50% activity relative to the maximum activity.

Production of Glucoamylase

Glucoamylases suitable for the embodiments of the present disclosure may be produced with recombinant DNA technology in various host cells.

In some embodiments, the host cells are selected from bacterial, fungal, plant and yeast cells. The term host cell includes both the cells, progeny of the cells and protoplasts created from the cells that are used to produce a variant glucoamylase according to the disclosure. In some embodiments, the host cells are fungal cells and typically filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts. Vegetative growth by filamentous fungi is by hyphal elongation and carbon catabolism is obligatory aerobic. In the embodiments of the present disclosure, the filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., (1984) Appl. Microbiol. Biotechnol 20:46-53; ATCC No. 56765 and ATCC No. 26921); *Penicillium* sp., *Humicola* sp. (e.g., *H. insolens, H. lanuginosa* and *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, and *A. awamori*) (Ward et al., (1993) Appl. Microbiol. Biotechnol. 39:738-743 and Goedegebuur et al., (2002) Genet 41:89-98), *Fusarium* sp., (e.g., *F. roseum, F. graminum F. cerealis, F. oxysporuim* and *F. venenatum*), *Neurospora* sp., (*N. crassa*), *Hypocrea* sp., *Mucor* sp., (*M. miehei*), *Rhizopus* sp. and *Emericella* sp. (see also, Innis et al., (1985) *Sci.* 228:21-26). The term "*Trichoderma*" or "*Trichoderma* sp." or "*Trichoderma* spp." refers to any fungal genus previously or currently classified as *Trichoderma*. In other embodiments, the host cell will be a genetically engineered host cell wherein native genes have been inactivated, for example by deletion in fungal cells. Where it is desired to obtain a fungal host cell having one or more inactivated genes known methods may be used (e.g. methods disclosed in U.S. Pat. Nos. 5,246,853 and 5,475,101, and WO 92/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes will be inactivated and/or typically deleted. Typically, *Trichoderma reesei* host cells having quad-deleted proteins are set forth and described in U.S. Pat. No. 5,847,276 and WO 05/001036. In other embodiments, the host cell is a protease deficient or protease minus strain.

To produce the glucoamylase of the embodiments of the present disclosure with the recombinant DNA technology, a DNA construct comprising nucleic acid encoding the amino acid sequence of the designated glucoamylase can be constructed and transferred into, for example, a *Trichoderma reesei* host cell. The vector may be any vector which when introduced into a *Trichoderma reesei* host cell can be integrated into the host cell genome and can be replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. The nucleic acid encoding the glucoamylase can be operably linked to a suitable promoter, which shows transcriptional activity in *Trichoderma reesei* host cell. The promoter may be derived from genes encoding proteins either homologous or heterologous to the host cell. Suitable non-limiting examples of promoters include cbh1, cbh2, egl1, egl2. In one embodiment, the promoter may be a native *T. reesei* promoter. Typically, the promoter can be *T. reesei* cbh1, which is an inducible promoter and has been deposited in GenBank under Accession No. D86235. An "inducible promoter" may refer to a promoter that is active under environmental or developmental regulation. In another embodiment, the promoter can be one that is heterologous to *T. reesei* host cell. Other examples of useful promoters include promoters from *A. awamori* and *A. niger* glucoamylase genes (see, e.g., Nunberg et al., (1984) *Mol. Cell Biol.* 4:2306-2315 and Boel et al., (1984) *EMBO J.* 3:1581-1585). Also, the promoters of the *T. reesei* xln1 gene and the cellobiohydrolase 1 gene may be useful (EPA 13f280A1).

In some embodiments, the glucoamylase coding sequence can be operably linked to a signal sequence. The signal sequence may be the native signal peptide of the glucoamylase (residues 1-20 of SEQ ID NO: 2 for HgGA, or residues 1-33 of SEQ ID NO: 5 for TrGA, for example). Alternatively, the signal sequence may have at least 90% or at least 95% sequence identity to the native signal sequence. In additional embodiments, a signal sequence and a promoter sequence comprising a DNA construct or vector to be introduced into the *T. reesei* host cell are derived from the same source. For example, in some embodiments, the signal sequence can be the cdh1 signal sequence that is operably linked to a cdh1 promoter.

In some embodiments, the expression vector may also include a termination sequence. In one embodiment, the termination sequence and the promoter sequence can be derived from the same source. In another embodiment, the termination sequence can be homologous to the host cell. A particularly suitable terminator sequence can be cbh1 derived from *T. reesei*. Other exemplary fungal terminators include the terminator from *A. niger* or *A. awamori* glucoamylase gene.

In some embodiments, an expression vector may include a selectable marker. Examples of representative selectable markers include ones that confer antimicrobial resistance (e.g., hygromycin and phleomycin). Nutritional selective markers also find use in the present invention including those markers known in the art as amdS, argB, and pyr4. Markers useful in vector systems for transformation of *Trichoderma* are known in the art (see, e.g., Finkelstein, chapter 6 in BIO-TECHNOLOGY OF FILAMENTOUS FUNGI, Finkelstein et al. Eds. Butterworth-Heinemann, Boston, Mass. (1992), Chap. 6.; and Kinghorn et al. (1992) APPLIED MOLECULAR GENETICS OF FILAMENTOUS FUNGI, Blackie Academic and Professional, Chapman and Hall, London). In a representative embodiment, the selective marker may be the amdS gene, which encodes the enzyme acetamidase, allowing transformed cells to grow on acetamide as a nitrogen source. The use of *A. nidulans* amdS gene as a selective marker is described for example in Kelley et al., (1985) *EMBO J.* 4:475-479 and Penttila et al., (1987) *Gene* 61:155-164.

An expression vector comprising a DNA construct with a polynucleotide encoding the glucoamylase may be any vector which is capable of replicating autonomously in a given fungal host organism or of integrating into the DNA of the host. In some embodiments, the expression vector can be a plasmid. In typical embodiments, two types of expression vectors for obtaining expression of genes are contemplated.

The first expression vector may comprise DNA sequences in which the promoter, glucoamylase-coding region, and terminator all originate from the gene to be expressed. In some embodiments, gene truncation can be obtained by deleting undesired DNA sequences (e.g., DNA encoding unwanted domains) to leave the domain to be expressed under control of its own transcriptional and translational regulatory sequences.

The second type of expression vector may be preassembled and contains sequences needed for high-level transcription and a selectable marker. In some embodiments, the coding region for the glucoamylase gene or part thereof can be inserted into this general-purpose expression vector such that it is under the transcriptional control of the expression construct promoter and terminator sequences. In some embodiments, genes or part thereof may be inserted downstream of a strong promoter, such as the strong cbh1 promoter.

Methods used to ligate the DNA construct comprising a polynucleotide encoding the glucoamylase, a promoter, a terminator and other sequences and to insert them into a suitable vector are well known in the art. Linking can be generally accomplished by ligation at convenient restriction sites. If such sites do not exist, the synthetic oligonucleotide linkers are used in accordance with conventional practice. (see, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. Nos. 6,022,725; 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "The Molecular Biology of *Trichoderma* and its Application to the Expression of Both Homologous and Heterologous Genes," in MOLECULAR INDUSTRIAL MYCOLOGY, Eds. Leong and Berka, Marcel Dekker Inc., NY (1992) pp. 129-148).

In some embodiments, genetically stable transformants can be constructed with vector systems whereby the nucleic acid encoding glucoamylase is stably integrated into a host strain chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability can be conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

Uptake of DNA into the host *Trichoderma* sp. strain is dependent upon the calcium ion concentration. Generally, between about 10 mM $CaCl_2$ and 50 mM $CaCl_2$ may be used in an uptake solution. Besides the need for the calcium ion in the uptake solution, other compounds generally included are a buffering system such as TE buffer (10 mM Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL, typically, $2\times10^6$/mL are used in transformation. A volume of 100 µL of these protoplasts or cells in an appropriate solution (e.g., 1.2 M sorbitol; 50 mM $CaCl_2$) are mixed with the desired DNA. Generally, a high concentration of PEG may be added to the uptake solution. From 0.1 to 1 volume of 25% PEG 4000 can be added to the protoplast suspension. It is also typical to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. See, e.g., U.S. Pat. Nos. 6,022,725 and 6,268,328.

Generally, the mixture can be then incubated at approximately 0° C. for a period of between 10 to 30 minutes. Additional PEG may then be added to the mixture to further enhance the uptake of the desired gene or DNA sequence. The 25% PEG 4000 can be generally added in volumes of 5 to 15 times the volume of the transformation mixture; however, greater and lesser volumes may be suitable. The 25% PEG 4000 may be typically about 10 times the volume of the transformation mixture. After the PEG is added, the transformation mixture can then be incubated either at room temperature or on ice before the addition of a sorbitol and $CaCl_2$ solution. The protoplast suspension can then be further added to molten aliquots of a growth medium. This growth medium permits the growth of transformants only.

Generally, cells are cultured in a standard medium containing physiological salts and nutrients (see, e.g., Pourquie, J. et al., BIOCHEMISTRY AND GENETICS OF CELLULOSE DEGRADATION, eds. Aubert, J. P. et al., Academic Press, pp. 7186, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present embodiments.

Culture-conditions are also standard, e.g., cultures are incubated at approximately 28° C. in appropriate medium in shake cultures or fermentors until desired levels of glucoamylase expression are achieved. After fungal growth has been established, the cells are exposed to conditions effective to cause or permit the expression of the glucoamylase. In cases where the glucoamylase coding sequence is under the control of an inducible promoter, the inducing agent (e.g., a sugar, metal salt or antimicrobial), can be added to the medium at a concentration effective to induce glucoamylase expression.

In general, the glucoamylase produced in cell culture may be secreted into the medium and may be purified or isolated, e.g., by removing unwanted components from the cell culture medium. In some cases, the glucoamylase can be produced in a cellular form, necessitating recovery from a cell lysate. In such cases, the enzyme may be purified from the cells in which it was produced using techniques routinely employed by those of skill in the art. Examples of these techniques include, but are not limited to, affinity chromatography (Tilbeurgh et al., (1984) *FEBS Lett.* 16: 215), ion-exchange chromatographic methods (Goyal et al., (1991) *Biores. Technol.* 36: 37; Fliess et al., (1983) *Eur. J. Appl. Microbiol. Biotechnol.* 17: 314; Bhikhabhai et al, (1984) *J. Appl. Biochem.* 6: 336; and Ellouz et al., (1987) *Chromatography* 396: 307), including ion-exchange using materials with high resolution power (Medve et al., (1998) *J. Chromatography A* 808: 153), hydrophobic interaction chromatography (see, Tomaz and Queiroz, (1999) *J. Chromatography A* 865: 123; two-phase partitioning (see, Brumbauer, et al., (1999) *Bioseparation* 7: 287); ethanol precipitation; reverse phase HPLC, chromatography on silica or on a cation-exchange resin such as DEAE, chromatofocusing, SDS-PAGE, ammonium sulfate precipitation, and gel filtration (e.g., Sephadex G-75).

Alpha-amylases

Alpha-amylases constitute a group of enzymes present in microorganisms and tissues from animals and plants. They are capable of hydrolyzing alpha-1,4-glucosidic bonds of glycogen, starch, related polysaccharides, and some oligosaccharides. Although all alpha-amylases possess the same catalytic function, their amino acid sequences vary greatly. The sequence identity between different amylases can be virtually non-existent, e.g., falling below 25%. Despite considerable amino acid sequence variation, alpha-amylases share a common overall topological scheme that has been identified after the three-dimensional structures of alpha-amylases from different species have been determined. The common three-dimensional structure reveals three domains: (1) a "TIM" barrel known as domain A, (2) a long loop region known as domain B that is inserted within domain A, and (3) a region close to the C-terminus known as domain C that contains a characteristic beta-structure with a Greek-key motif.

"Termamyl-like" alpha-amylases refer to a group of alpha-amylases widely used in the starch-processing industry. The *Bacillus licheniformis* alpha-amylase having an amino acid sequence of SEQ ID NO: 2 of U.S. Pat. No. 6,440,716 is commercially available as Termamyl®. Termamyl-like alpha-amylases commonly refer to a group of highly homologous alpha-amylases produced by *Bacillus* spp. Other members of the group include the alpha-amylases from *Geobacillus stearothermophilus* (previously known as *Bacillus stearothermophilus*; both names are used interchangeably in the present disclosure) and *Bacillus amyloliquefaciens*, and those derived from *Bacillus* sp. NCIB 12289, NCIB 12512, NCIB 12513, and DSM 9375, all of which are described in detail in U.S. Pat. No. 6,440,716 and WO 95/26397.

Although alpha-amylases universally contain the three domains discussed above, the three-dimensional structures of some alpha-amylases, such as AmyE from *Bacillus subtilis*, differ from Termamyl-like alpha-amylases. These enzymes are collectively referred as non-Termamyl-like alpha-amylases. "AmyE" for the purpose of this disclosure means a naturally occurring alpha-amylase (EC 3.2.1.1; 1,4-α-D-glucan glucanohydrolase) from *Bacillus subtilis*. Representative AmyE enzymes and the variants thereof are disclosed in U.S. patent application Ser. Nos. 12/478,266 and 12/478,368, both filed Jun. 4, 2009, and Ser. No. 12/479,427, filed Jun. 5, 2009.

Other commercially available amylases can be used, e.g., TERMAMYL® 120-L, LC and SC SAN SUPER®, SUPRA®, and LIQUEZYME® SC available from Novo Nordisk A/S, FUELZYME® FL from Diversa, and CLARASE® L, SPEZYME® FRED, SPEZYME® ETHYL, GC626, and GZYME® G997 available from Danisco, US, Inc., Genencor Division.

Other Enzymes and Enzyme Combinations

In embodiments of the present disclosure, other enzyme(s) may also be supplemented in starch processing, during saccharification and/or fermentation. These supplementary enzymes may include proteases, pullulanases, isoamylases, cellulases, hemicellulases, xylanases, cyclodextrin glycotransferases, lipases, phytases, laccases, oxidases, esterases, cutinases, xylanases, pullulanases, and/or alpha-glucosidases. See e.g., WO 2009/099783. Skilled artisans in the art are well aware of the methods using the above-listed enzymes.

The glucoamylases disclosed herein can be used in combination with any other enzyme. For example, glucoamylase maybe used in combination with amylases (e.g., alpha-amylases). In one embodiment, saccharification and/or fermentation or the simultaneous saccharification and fermentation (SSF) process use glucoamylase and one or more non-starch polysaccharide hydrolyzing enzymes. These enzymes are capable of hydrolyzing complex carbohydrate polymers such as cellulose, hemicellulose, and pectin. Non-limiting examples include cellulases (e.g., endo and exo-glucanases, beta glucosidase) hemicellulases (e.g., xylanases) and pectinases. In another embodiment, saccharification and/or fermentation or the SSF process use glucoamylase, alpha-amylase and one or more non-starch polysaccharide hydrolyzing enzymes. In another embodiment, saccharification and/or fermentation or the SSF process use glucoamylase with phytases, proteases, isoamylases and pullulanases.

In some embodiments, the saccharification and/or fermentation or the SSF process can use at least two non-starch polysaccharide hydrolyzing enzymes. In some embodiments, the saccharification and/or fermentation or the SSF process can use at least three non-starch polysaccharide hydrolyzing enzymes.

Cellulases are enzyme compositions that hydrolyze cellulose (β-1,4-D-glucan linkages) and/or derivatives thereof, such as phosphoric acid swollen cellulose. Cellulases include the classification of exo-cellobiohydrolases (CBH), endoglucanases (EG) and β-glucosidases (BG) (EC3.2.191, EC3.2.1.4 and EC3.2.1.21). Examples of cellulases include cellulases from *Penicillium, Trichoderma, Humicola, Fusarium, Thermomonospora, Cellulomonas, Hypocrea, Clostridium, Thermomonospore, Bacillus, Cellulomonas* and *Aspergillus*. Non-limiting examples of commercially available cellulases sold for feed applications are beta-glucanases such as ROVABIO® (Adisseo), NATUGRAIN® (BASF), MULTIFECT® BGL (Danisco Genencor) and ECONASE® (AB Enzymes). Some commercial cellulases includes ACCELERASE®. The cellulases and endoglucanases described in US20060193897A1 also may be used.

Beta-glucosidases (cellobiase) hydrolyzes cellobiose into individual monosaccharides. Various beta glucanases find use in the invention in combination with phytases. Beta glucanases (endo-cellulase-enzyme classification EC 3.2.1.4) also called endoglucanase I, II, and III, are enzymes that will attack the cellulose fiber to liberate smaller fragments of cellulose which is further attacked by exo-cellulase to liberate glucose. Commercial beta-glucanases useful in the methods of the invention include OPTIMASH® BG and OPTIMASH® TBG (Danisco, US, Inc. Genencor Division).

Hemicellulases are enzymes that break down hemicellulose. Hemicellulose categorizes a wide variety of polysaccharides that are more complex than sugars and less complex than cellulose, that are found in plant walls. In some embodiments, a xylanase find use as a secondary enzyme in the methods of the invention. Any suitable xylanase can be used in the invention. Xylanases (e.g. endo-β-xylanases (E.C. 3.2.1.8), which hydrolyze the xylan backbone chain, can be from bacterial sources (e.g., *Bacillus, Streptomyces, Clostridium, Acidothermus, Microtetrapsora* or *Thermonospora*) or from fungal sources (*Aspergillus, Trichoderma, Neurospora, Humicola, Penicillium* or *Fusarium* (See, e.g., EP473 545; U.S. Pat. No. 5,612,055; WO 92/06209; and WO 97/20920)). Xylanases useful in the invention include commercial preparations (e.g., MULTIFECT® and FEEDTREAT® Y5 (Danisco Genencor), RONOZYME® WX (Novozymes A/S) and NATUGRAIN WHEAT® (BASF). In some embodiments the xylanase is from *Trichoderma reesei* or a variant xylanase from *Trichoderma reesei*, or the inherently thermostable xylanase described in EP1222256B1, as well as other xylanases from *Aspergillus niger, Aspergillus kawachii, Aspergillus tubigensis, Bacillus circulans, Bacillus pumilus, Bacillus subtilis, Neocallimastix patriciarum, Penicillium* species, *Streptomyces lividans, Streptomyces thermoviolaceus, Thermomonospora fusca, Trichoderma harzianum, Trichoderma reesei*, and *Trichoderma viridae*.

Phytases that can be used include those enzymes capable of liberating at least one inorganic phosphate from inositol hexaphosphate. Phytases are grouped according to their preference for a specific position of the phosphate ester group on the phytate molecule at which hydrolysis is initiated, (e.g., as 3-phytases (EC 3.1.3.8) or as 6-phytases (EC 3.1.3.26)). A typical example of phytase is myo-inositol-hexakiphosphate-3-phosphohydrolase. Phytases can be obtained from microorganisms such as fungal and bacterial organisms (e.g. *Aspergillus* (e.g., *A. niger, A. terreus*, and *A. fumigatus*), *Myceliophthora* (*M. thermophila*), *Talaromyces* (*T. thermophilus*) *Trichoderma* spp (*T. reesei*). And *Thermomyces* (See e.g., WO 99/49740)). Also phytases are available from *Penicillium* species, (e.g., *P. hordei* (See e.g., ATCC No. 22053), *P. piceum* (See e.g., ATCC No. 10519), or *P. brevi-compactum* (See e.g., ATCC No. 48944) (See, e.g. U.S. Pat. No. 6,475, 762). Additional phytases that find use in the invention are available from *Peniophora, E. coli, Citrobacter, Enterbacter* and *Buttiauxella* (see e.g., WO2006/043178, filed Oct. 17, 2005). Additional phytases useful in the invention can be obtained commercially (e.g. NATUPHOS® (BASF), RONOZYME® P (Novozymes A/S), PHZYME® (Danisco A/S, Diversa) and FINASE® (AB Enzymes).

Various acid fungal proteases (AFP) can be used as part of the combination as well. Acid fungal proteases include for example, those obtained from *Aspergillus, Trichoderma, Mucor* and *Rhizopus*, such as *A. niger, A. awamori, A. oryzae* and *M. miehei*. AFP can be derived from heterologous or endogenous protein expression of bacteria, plants and fungi sources. IAFP secreted from strains of *Trichoderma* can be used. Suitable AFP includes naturally occurring wild-type AFP as well as variant and genetically engineered mutant AFP. Some commercial AFP enzymes useful in the invention include FERMGEN® (Danisco US, Inc, Genencor Division), and FORMASE® 200.

Proteases can also be used with glucoamylase and any other enzyme combination. Any suitable protease can be used. Proteases can be derived from bacterial or fungal sources. Sources of bacterial proteases include proteases from *Bacillus* (e.g., *B. amyloliquefaciens, B. lentus, B. licheniformis*, and *B. subtilis*). Exemplary proteases include, but are not limited to, subtilisin such as a subtilisin obtainable from *B. amyloliquefaciens* and mutants thereof (U.S. Pat. No. 4,760,025). Suitable commercial protease includes MULTIFECT® P 3000 (Danisco Genencor) and SUMIZYME® FP (Shin Nihon). Sources of suitable fungal proteases include, but are not limited to, *Trichoderma, Aspergillus, Humicola* and *Penicillium*, for example.

Debranching enzymes, such as an isoamylase (EC 3.2.1.68) or pullulanase (EC 3.2.1.41), can also be used in combination with the glucoamylases in the saccharification and/or fermentation or SSF processes of the invention. A non-limiting example of a pullulanase that can be used is Promozyme®.

Starch Processing

Starch Substrates and Raw Materials

Those of skill in the art are well aware of available methods that may be used to prepare starch substrates for use in the processes disclosed herein. For example, a useful starch substrate may be obtained from tubers, roots, stems, legumes, cereals, or whole grain. More specifically, the granular starch comes from plants that produce high amounts of starch. For example, granular starch may be obtained from corn, wheat, barley, rye, milo, sago, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains about 70-72% starch. Specifically contemplated starch substrates are cornstarch, wheat starch, and barley starch. The starch from a grain may be ground or whole and includes corn solids, such as kernels, bran and/or cobs. The starch may be highly refined raw starch or feedstock from starch refinery processes. Various starches also are commercially available. For example, cornstarch may be available from Cerestar, Sigma, and Katayama Chemical Industry Co. (Japan); wheat starch may be available from Sigma; sweet potato starch may be available from Wako Pure Chemical Industry Co. (Japan); and potato starch may be available from Nakaari Chemical Pharmaceutical Co. (Japan).

Milling

The starch substrate can be a crude starch from milled whole grain, which contains non-starch fractions, e.g., germ residues and fibers. Milling may comprise either wet milling or dry milling. In wet milling, whole grain can be soaked in water or dilute acid to separate the grain into its component parts, e.g., starch, protein, germ, oil, kernel fibers. Wet milling efficiently separates the germ and meal (i.e., starch granules and protein) and can be especially suitable for production of syrups. In dry milling, whole kernels are ground into a fine powder and processed without fractionating the grain into its component parts. Dry milled grain thus will comprise significant amounts of non-starch carbohydrate compounds, in addition to starch. Most ethanol comes from dry milling. Alternatively, the starch to be processed may be a highly refined starch quality, for example, at least about 90%, at least about 95%, at least about 97%, or at least about 99.5% pure.

Gelatinization and Liquefaction

In some embodiments of the invention, gelatinazation and/or liquefaction may be used. As used herein, the term "liquefaction" or "liquefy" means a process by which starch is converted to less viscous and soluble shorter chain dextrins. In some embodiments, this process involves gelatinization of starch simultaneously with or followed by the addition of alpha-amylases. Additional liquefaction-inducing enzymes, e.g., a phytase, optionally may be added. In some embodiments, gelatinization is not used. In other embodiments, a separate liquefaction step is not used. Starches can be converted to shorter chains at the same time that saccharification and/or fermentation is performed. In some embodiments, the starch is being converted directly to glucose. In other embodiments, a separate liquefaction step is used prior to saccharification.

In some embodiments, the starch substrate prepared as described above may be slurried with water. The starch slurry may contain starch as a weight percent of dry solids of about 10-55%, about 20-45%, about 30-45%, about 30-40%, or about 30-35%. In some embodiments, the starch slurry is at least about 5%, at least about 10%, at least about 15%, at least about 20%, at least about 25%, at least about 30%, at least about 35%, at least about 40%, at least about 45%, at least about 50%, or at least about 55%.

To optimize alpha-amylase stability and activity, the pH of the slurry may be adjusted to the optimal pH for the alpha-amylases. Alpha-amylases remaining in the slurry following liquefaction may be deactivated by lowering pH in a subsequent reaction step or by removing calcium from the slurry. The pH of the slurry should be adjusted to a neutral pH (e.g., pH 5.0 to 8.0 and any pH in between this range) when the glucoamylases of the invention are used.

The slurry of starch plus the alpha-amylases may be pumped continuously through a jet cooker, which may be steam heated from about 85° C. to up to about 105° C. Gelatinization occurs very rapidly under these conditions, and the enzymatic activity, combined with the significant shear forces, begins the hydrolysis of the starch substrate. The residence time in the jet cooker can be very brief. The partly gelatinized starch may be passed into a series of holding tubes maintained at about 85-105° C. and held for about 5 min. to complete the gelatinization process. These tanks may contain baffles to discourage back mixing. As used herein, the term "secondary liquefaction" refers the liquefaction step subsequent to primary liquefaction, when the slurry is allowed to cool to room temperature. This cooling step can be about 30 minutes to about 180 minutes, e.g., about 90 minutes to 120 minutes. Milled and liquefied grain is also known as mash.

Saccharification

Following liquefaction, the mash can be further hydrolyzed through saccharification to produce fermentable sugars that can be readily used in the downstream applications. The saccharification of the present embodiments can be carried out at a pH in the range of 5.0 to 8.0, 5.5 to 7.5, 6.0 to 7.5, 6.5 to 7.5, or 7.0 to 7.5, by using a glucoamylase as described above. In other embodiments, the pH used can be 5.0, 5.25, 5.50, 5.75, 6.0, 6.50, 7.0, 7.50 or 8.0.

In one embodiment, at pH 6.0 or higher, the glucoamylase possesses at least about 50%, about 51%, about 52%, about 53%, about 54%, or about 55% activity relative to its maximum activity at the optimum pH. In another embodiment, for a pH range of 6.0 to 7.5, HgGA can have at least 53% activity relative to its maximum activity. In another embodiment, at pH 6.0, TrGA can have at least 50% activity relative to its maximum activity. In one embodiment, a glucoamylase (e.g. HgGA) has 67% maximal activity at pH 7.0. In another embodiment, a glucoamylase (e.g., TrGA) has 66% maximal activity at pH 5.25.

In one embodiment, the glucoamylase may be dosed at the range of about 0.2 to 2.0 GAU/g dss, about 0.5 to 1.5 GAU/g dss, or 1.0 to 1.5 GAU/g dss. In another embodiment, glucoamylase (e.g., TrGA) can be used at a dose of about 1 GAU/gds starch, 2 GAU/gds starch, 3 GAU/gds starch, 4 GAU/gds starch, or 5 GAU/gds starch. In one embodiment, glucoamylase (e.g., HgGA) can be used at a dose of about 0.25 to 1 GAU/gds starch. In another embodiment, glucoamylase (e.g., HgGA) can be used at a dose of about 0.25 GAU/gds starch, 0.5 GAU/gds starch, 0.75 GAU/gds starch, or 1 GAU/gds starch. The saccharification may be performed at about 30 to about 60° C., or about 40 to about 60° C. In some embodiments, the saccharification occurs at ph 7.0 at 32° C. In other embodiments, the saccharification occurs at ph 6.5 at 58° C.

A full saccharification step may typically range 24 to 96 hours, 24 to 72 hours, or 24 to 48 hours. In some embodiments, saccharification occurs after about 2, 4, 6, 7.7, 8, 110, 14, 16, 18, 20, 22, 23.5, 24, 26, 28, 30, 31.5, 34, 36, 38, 40, 42, 44, 46, or 48 hours. In some embodiments, the saccharification step and fermentation step are combined and the process is referred to as simultaneous saccharification and fermentation (SSF).

It is understood that generally, as time elapses, the enzymes (glucoamylase with or without other enzymes, such as alpha-amylases or non-starch polysaccharide hydrolyzing enzyme) reduces the higher sugars to lower DP sugars (such as DP1). The sugar profile can be varied by using different parameters, such as, but not limited to, starting starch substrate, temperature, amount of glucoamylase, type of glucoamylase, and pH. For example, in one embodiment, at 32 degrees Celsius and pH 7.0, the sugar or oligosaccharide distribution during the saccharification process can be between about 0.36% to about 96.50% DP1, about 3.59% to about 11.80% DP2, about 0.12% to about 7.75%, and/or about 2.26% to about 88.30% for higher sugars for HgGA. In another embodiment, at 32 degrees Celsius and pH 7.0, the sugar distribution during the saccharification process can be between about 0.36% to about 79.19% DP1, between about 3.59% to about 9.92% DP2, about 0.17% to about 9.10% DP3 and/or about 17.15% to about 88.30% for higher sugars for TrGA. Thus, in one embodiment, using HgGA, the DP1 content can reach more than 90% after 24 hours. After 45 hours, the DP1 content can reach more than 96%, while the content of higher sugars can decrease to less than 3%. Using TrGA, more than 70% DP1 can be obtained after 24 hours. After 45 hours, the DP1 content can reach about 80%, while the content of higher sugars can drop to less than 20%.

In another embodiment, at 58 degrees Celsius and pH 6.5, the sugar distribution during the saccharification process can be between about 60.66% to about 93.67% DP1, between about 1.49% to about 8.87% DP2, about 0.33% to about 1.93% DP3 and/or about 4.51% to about 28.17% for higher sugars for HgGA. In other embodiments, at 58 degrees Celsius and pH 6.5, the sugar or oligosaccharide distribution during the saccharification process can be between about 37.08% to about 75.25% DP1, about 5.48% to about 10.19% DP2, about 0.46% to about 5.06%, and/or about 18.37% to about 47.47% for higher sugars for TrGA. Thus, in one embodiment, using HgGA, the DP1 content can reach more than 90% after 24 hours. After 48 hours, the DP1 content can reach more than 93%, while the content of higher sugars can decrease to less than 5%. Using TrGA, more than 70% DP1 can be obtained after 24 hours. After 45 hours, the DP1 content can reach about 75%, while the content of higher sugars can drop to about 18%.

In yet another embodiment, at 58 degrees Celsius and pH 6.5, glucoamylases disclosed herein can be used to saccharify a starch substrate where high sugars (e.g., DP4+) is reduced. In some embodiments, the sugar or oligosaccharide distribution during the saccharification process can be between about 81.10% to about 90.36% DP1, about 1.99% to about 3.96% DP2, about 0.49% to about 0.61% DP3, about 4.48% to about 16.13% DP4+ for TrGA. In other embodiments, the sugar or oligosaccharide distribution during the saccharification process can be between about 93.15% to about 95.33% DP1, about 2.10% to about 3.94% DP2, about 0.53% to about 1.00% DP3, about 0.94% to about 3.76% DP4+ for HgGA.

In yet another embodiment, at 58 degrees Celsius and pH 6.4, the sugar or oligosaccharide distribution during the saccharification process can be between about 93.79% to about 96.9% DP1, about 1.55% to about 3.02% DP2, about 0.2% to about 0.49% DP3 and about 0% to about 3.98% DP4+ for HgGA. In some cases, about 93% solubility and about 96.9% glucose yield can be achieved within 24 hours. Continuous saccharification can result in 99% solubility and about 96.8% glucose after about 48 hours.

In another embodiment, at 58 degrees Celsius and pH 6.4, the sugar or oligosaccharide distribution during the saccharification process can be between about 75.08% to about 96.5% DP1, 1.57% to about 9.16% DP2, 0.67% to about 15.76% DP3+. In some cases, HgGA can maintain a significant amount of glucoamylase activity for about 52 hours at pH6.4 to yield continued production of DP1 products, DP2 products, and increase of percentage of soluble solids. Increased amounts of HgGA can result in increased rates of percentage solubilization and DP1 production.

In some embodiments, the invention can be used to produce DP2 sugars for fermentation by yeast. For example, DP2 sugars can be produced from about 3.59% to about 11.80% DP2, from about 3.59% to about 9.92% DP2, from about 1.49% to about 8.87% DP2, from about 5.48% to about 10.19% DP2, from about 1.99% to about 3.96% DP2, from about 2.10% to about 3.94% DP2, from about 1.55% to about 3.02% DP2, or from about 1.57% to about 9.16% DP2.

Fermentation

In some embodiments of the present disclosure, the fermentable sugars may be subject to batch or continuous fermentation conditions. A classical batch fermentation is a closed system, wherein the composition of the medium is set at the beginning of the fermentation and is not subject to artificial alterations during the fermentation. Thus, at the beginning of the fermentation the medium may be inoculated with the desired organism(s), e.g., a microorganism engineered to produce isoprenoids. In this method, fermentation can be permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase, and finally to a stationary phase where growth rate is diminished or halted. If untreated, cells in the stationary phase eventually die. In general, cells in log phase are responsible for the bulk of production of the end product.

A variation on the standard batch system is the "fed-batch fermentation" system, which may be used in some embodiments of the present disclosure. In this variation of a typical batch system, the substrate can be added in increments as the fermentation progresses. Fed-batch systems are particularly useful when catabolite repression is apt to inhibit the metabolism of the cells and where it is desirable to have limited amounts of substrate in the medium. Measurement of the actual substrate concentration in fed-batch systems may be difficult and is therefore estimated on the basis of the changes of measurable factors such as pH, dissolved oxygen and the partial pressure of waste gases such as $CO_2$. Both batch and fed-batch fermentations are common and well known in the art.

On the other hand, continuous fermentation is an open system where a defined fermentation medium can be added continuously to a bioreactor and an equal amount of conditioned medium can be removed simultaneously for processing. Continuous fermentation generally maintains the cultures at a constant high density where cells are primarily in log phase growth. Continuous fermentation allows for the modulation of one factor or any number of factors that affect cell growth and/or end product concentration. For example, in one embodiment, a limiting nutrient such as the carbon source or nitrogen source can be maintained at a fixed rate while all other parameters are allowed to moderate. In other systems, a number of factors affecting growth can be altered continuously while the cell concentration, measured by media turbidity, may be kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

In further embodiments, by use of appropriate fermenting microorganisms as known in the art, the fermentation end product may include without limitation alcohol, 1,3-propanediol, succinic acid, lactic acid, amino acids, proteins, functional oligosaccharides, and derivatives thereof. See e.g., WO 2008/086811 (methanol, ethanol, propanol, and butanol fermentation); WO 2003/066816, U.S. Pat. Nos. 5,254,467 and 6,303,352 (1,3-propanediol fermentation); U.S. Pat. Nos. RE 37,393, 6,265,190, and 6,596,521 (succinic acid fermentation); U.S. Pat. No. 5,464,760, WO 2003/095659, Mercier et al., *J. Chem. Tech. Biotechnol.* 55: 111-121, Zhang and Cheryan, *Biotechnol. Lett.* 13: 733-738 (1991), Linko and Javanainen, *Enzyme Microb. Technol.* 19: 118-123 (1996), and Tsai and Moon, *Appl. Biochem. Biotechnol.* 70-72: 417-428 (1998) (lactic acid fermentation); U.S. Pat. Nos. 7,320, 882, 7,332,309, 7,666,634, and Zhang et al., *Appl. Microbiol. Biotechnol.* 77: 355-366 (2007) (fermentation of various amino acids).

Recombinant Cells Capable of Increased Production of Isoprenoid Precursors and/or Isoprenoids Isoprenoids can be produced in many organisms from the synthesis of the isoprenoid precursor molecules which are the end products of the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., *Plant Physiol.* 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate ($C_{10}$-GPP), farnesyl pyrophosphate ($C_{15}$-FPP), geranylgeranyl pyrophosphate ($C_{20}$-GGPP)) with corresponding number of isopentenyl pyrophosphates ($C_5$-IPP) (Hsieh et al., *Plant Physiol.* 2011 March; 155(3): 1079-90).

Production of isoprenoid precursors and/or isoprenoid can be made by using any of the recombinant host cells disclosed herein, in particular by using the SSF methodology with the glucoamylases and/or other enzyme combinations disclosed herein. In some aspects, these cells comprise one or more heterologous nucleic acids encoding polypeptides of the MVA pathway, IDI, and/or the DXP pathway, as described above, and a heterologous nucleic acid encoding a polyprenyl pyrophosphate synthase polypeptide. Without being bound to theory, it is thought that increasing the cellular production of mevalonate in bacterial cells by any of the compositions and methods described above will similarly result in the production of higher amounts of isoprenoid precursor molecules and/or isoprenoids. Increasing the molar yield of mevalonate production from glucose translates into higher molar yields of isoprenoid precursor molecules and/or isoprenoids, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprenoid production.

Types of Isoprenoids

The cells of the present invention are capable of increased production of isoprenoids and the isoprenoid precursor molecules DMAPP and IPP. Examples of isoprenoids include, without limitation, hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, farnesene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

Heterologous Nucleic Acids Encoding Polyprenyl Pyrophosphate Synthases Polypeptides In some aspects of the invention, the recombinant cells described in any of the compositions or methods herein comprising acetoacetyl-CoA synthase further comprise one or more nucleic acids encoding a non-thiolase MVA pathway polypeptide(s), as described above, as well as one or more nucleic acids encoding a polyprenyl pyrophosphate synthase polypeptides(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to overexpress the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of a polyprenyl pyrophosphate synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in E. coli. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3):1079-90; Danner et al., *Phytochemistry.* 2011 Apr. 12 [Epub ahead of print]; Jones et al., *J Biol Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köllner & Boland, *J Org Chem.* 2010 Aug. 20; 75(16):5590-600.

MVA Pathway

In some aspects of the invention, the cells described in any of the compositions or methods described herein comprise a nucleic acid encoding an MVA pathway polypeptide. In some embodiments, the MVA pathway polypeptide is an endogenous polypeptide. In some embodiments, the cells comprise one or more additional copies of an endogenous nucleic acid encoding an MVA pathway polypeptide. In some embodiments, the endogenous nucleic acid encoding an MVA pathway polypeptide operably linked to a constitutive promoter. In some embodiments, the endogenous nucleic acid encoding an MVA pathway polypeptide operably linked to a constitutive promoter. In some embodiments, the endogenous nucleic acid encoding an MVA pathway polypeptide is operably linked to a strong promoter. In a particular embodiment, the cells are engineered to over-express the endogenous MVA pathway polypeptide relative to wild-type cells.

In some embodiments, the MVA pathway polypeptide is a heterologous polypeptide. In some embodiments, the cells comprise more than one copy of a heterologous nucleic acid encoding an MVA pathway polypeptide. In some embodiments, the heterologous nucleic acid encoding an MVA pathway polypeptide is operably linked to a constitutive promoter. In some embodiments, the heterologous nucleic acid encoding an MVA pathway polypeptide is operably linked to a strong promoter.

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprenoid production can also be used as well.

In some embodiments, feedback resistant mevalonate kinase polypeptides can be used to increase the production of isoprenoids. As such, the invention provides methods for producing isoprenoids wherein the host cells further comprise (i) one or more non-modified nucleic acids encoding feedback-resistant mevalonate kinase polypeptides or (ii) one or more additional copies of an endogenous nucleic acid encoding a feedback-resistant mevalonate kinase polypeptide. Non-limiting examples of mevalonate kinase which can be used include: archaeal mevalonate kinase (e.g., from *M. mazei, Lactobacillus* mevalonate kinase polypeptide, *Lactobacillus sakei* mevalonate kinase polypeptide, yeast mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *M. Burtonii* mevalonate kinase polypeptide).

In another embodiment, aerobes are engineered with polyprenyl pyrophosphate synthase using standard techniques known to one of skill in the art. In another embodiment, anaerobes are engineered with polyprenyl pyrophosphate synthase and one or more MVA pathway polypeptides using standard techniques known to one of skill in the art. In yet another embodiment, either aerobes or anaerobes are engineered with polyprenyl pyrophosphate synthase, one or more MVA pathway polypeptides and/or one or more DXP pathway polypeptides using standard techniques known to one of skill in the art.

Types of MVA pathway polypeptides and/or DXP pathway polypeptides which can be used and methods of making microorganisms (e.g., facultative anaerobes such as *E. coli*) encoding MVA pathway polypeptides and/or DXP pathway polypeptides are also described in International Patent Application Publication No. WO2009/076676; U.S. Publ. 20100048964, US Publ. 2010/0086978, US Publ. 2010/0167370, US Publ. 2010/0113846, US Publ. 2010/0184178, and US Publ. 2010/0167371; U.S. Publ. 2011/0014672, U.S. Publ. 2010/0196977, and US Publ. 2011/0046422; WO 2004/033646 and WO 96/35796.

One of skill in the art can readily select and/or use suitable promoters to optimize the expression of polyprenyl pyrophosphate synthase or and one or more MVA pathway polypeptides and/or one or more DXP pathway polypeptides in anaerobes. Similarly, one of skill in the art can readily select and/or use suitable vectors (or transfer vehicle) to optimize the expression of polyprenyl pyrophosphate synthase or and one or more MVA pathway polypeptides and/or one or more DXP pathway polypeptides in anaerobes. In some embodiments, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some embodiments, an polyprenyl pyrophosphate synthase or MVA pathway nucleic acid integrates into a chromosome of the cells without a selective marker.

In some embodiments, the vector is a shuttle vector, which is capable of propagating in two or more different host species. Exemplary shuttle vectors are able to replicate in *E. coli* and/or *Bacillus subtilis* and in an obligate anaerobe, such as *Clostridium*. Upon insertion of an polyprenyl pyrophosphate synthase or MVA pathway nucleic acid into the shuttle vector using techniques well known in the art, the shuttle vector can be introduced into an *E. coli* host cell for amplification and selection of the vector. The vector can then be isolated and introduced into an obligate anaerobic cell for expression of the polyprenyl pyrophosphate synthase or MVA pathway polypeptide.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethyl allyl diphosphate (DMAPP) (e.g., converting IPP into DMAPP and/or converting DMAPP into IPP). While not intending to be bound by any particular theory, it is believed that increasing the amount of IDI polypeptide in cells increases the amount (and conversion rate) of IPP that is converted into DMAPP, which in turn is converted into an isoprenoid product. Exemplary IDI polypeptides include polypeptides, fragments of polypeptides, peptides, and fusions polypeptides that have at least one activity of an IDI polypeptide. Standard methods can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary DXP Pathway Polypeptides and Nucleic Acids

DXS and IDI polypeptides are part of the DXP pathway for the biosynthesis of isoprenoids. 1-deoxy-D-xylulose-5-phosphate synthase (DXS) polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater production of isoprenoids.

Exemplary DXS polypeptides include polypeptides, fragments of polypeptides, peptides, and fusions polypeptides that have at least one activity of a DXS polypeptide. Standard methods known to one of skill in the art and as taught the references cited herein can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

In some embodiments, the DXS or DXP pathway polypeptide is an endogenous polypeptide. In some embodiments, the cells comprise one or more additional copies of an endogenous nucleic acid encoding a DXS or DXP pathway polypeptide. In other embodiments, the DXS or DXP pathway polypeptide is a heterologous polypeptide. In some embodiments, the cells comprise more than one copy of a heterologous nucleic acid encoding an DXS or DXP pathway polypeptide. In any of the embodiments herein, the nucleic acid is operably linked to a promoter (e.g., inducible or constitutive promoter).

Source Organisms

Polyprenyl pyrophosphate synthase and/or MVA pathway nucleic acids (and their encoded polypeptides) and/or DXP pathway nucleic acids (and their encoded polypeptides) can be obtained from any organism that naturally contains polyprenyl pyrophosphate synthase and/or MVA pathway nucleic acids and/or DXP pathway nucleic acids. Some organisms contain the MVA pathway for producing isoprenoids. Polyprenyl pyrophosphate synthase nucleic acids can be obtained, e.g., from any organism that contains an polyprenyl pyrophosphate synthase. MVA pathway nucleic acids can be obtained, e.g., from any organism that contains the MVA pathway. DXP pathway nucleic acids can be obtained, e.g., from any organism that contains the DXP pathway.

Host Cells

Various types of host cells can be used to produce isoprenoids as part of a biologically produced composition. In some embodiments, the host cell is a yeast, such as *Saccharomyces* sp., *Schizosaccharomyces* sp., *Pichia* sp., *Candida* sp. or *Y. lipolytica*.

In some embodiments, the host cell is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of Archaea such as *Methanosarcina mazei*, and strains of *Corynebacterium* such as *C. glutamicum*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

In some embodiments, the host cell is a gram-positive bacterium. Non-limiting examples include strains of *Streptomyces* (e.g., *S. lividans, S. coelicolor,* or *S. griseus*) and *Bacillus*. In some embodiments, the source organism is a gram-negative bacterium, such as *E. coli* or *Pseudomonas* sp.

In some embodiments, the host cell is a plant, such as a plant from the family Fabaceae, such as the Faboideae subfamily. In some embodiments, the source organism is kudzu, poplar (such as *Populus alba×tremula* CAC35696), aspen (such as *Populus tremuloides*), or *Quercus robur*.

In some embodiments, the host cell is an algae, such as a green algae, red algae, glaucophytes, chlorarachniophytes, euglenids, chromista, or dinoflagellates.

In some embodiments, the host cell is a cyanobacteria, such as cyanobacteria classified into any of the following groups based on morphology: Chroococcales, Pleurocapsales, Oscillatoriales, Nostocales, or Stigonematales.

In some embodiments, the host cell is an anaerobic organisms. An "anaerobe" is an organism that does not require oxygen for growth. An anaerobe can be an obligate anaerobe, a facultative anaerobe, or an aerotolerant organism. Such organisms can be any of the organisms listed above, bacteria, yeast, etc. An "obligate anaerobe" is an anaerobe for which atmospheric levels of oxygen can be lethal. Examples of obligate anaerobes include, but are not limited to, *Clostridium, Eurobacterium, Bacteroides, Peptostreptococcus, Butyribacterium, Veillonella,* and *Actinomyces*. In one embodiment, the obligate anaerobes can be any one or combination selected from the group consisting of *Clostridium ljungdahlii, Clostridium autoethanogenum, Eurobacterium limosum, Clostridium carboxydivorans, Peptostreptococcus productus,* and *Butyribacterium methylotrophicum*. A "facultative anaerobe" is an anaerobe that is capable of performing aerobic respiration in the presence of oxygen and is capable of performing anaerobic fermentation under oxygen-limited or oxygen-free conditions. Examples of facultative anaerobes include, but are not limited to, *Escherichia, Pantoea*, yeast, and *Yarrowia*.

In some embodiments, the host cell is a photosynthetic cell. In other embodiments, the host cell is a non-photosynthetic cell.

Transformation Methods

Nucleic acids encoding polyprenyl pyrophosphate synthase and/or MVA pathway polypeptides and/or DXP pathway polypeptides can be inserted into any host cell using standard techniques for expression of the encoded polyprenyl pyrophosphate synthase and/or MVA pathway polypeptide. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., Curr. Genet. 16:53-56, 1989 or "Handbook on Clostridia" (P. Dune, ed., 2004). For obligate anaerobic host cells, such as *Clostridium*, electroporation, as described by Davis et al., 2005 and in Examples III and IV, can be used as an effective technique. The introduced nucleic acids may be integrated into chromosomal DNA or maintained as extrachromosomal replicating sequences.

Additionally, isoprenoid production by cells that contain a heterologous polyprenyl pyrophosphate synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells.

Iron-sulfur cluster-interacting redox polypeptide can also be used to increase the activity demonstrated by the DXP pathway polypeptides (such as HDS (GcpE or IspG) or HDR polypeptide (IspH or LytB). While not intending to be bound to a particular theory, the increased expression of one or more endogenous or heterologous iron-sulfur interacting redox nucleic acids or polypeptides improve the rate of formation and the amount of DXP pathway polypeptides containing an iron sulfur cluster (such as HDS or HDR), and/or stabilize DXP pathway polypeptides containing an iron sulfur cluster (such as HDS or HDR). This in turn increases the carbon flux to isoprenoid synthesis in cells by increasing the synthesis of HMBPP and/or DMAPP and decreasing the cMEPP and HMBPP pools in the DXP pathway.

Additional Host Cell Mutations

The invention also contemplates additional host cell mutations that increase carbon flux through the MVA pathway. By increasing the carbon flow, more isoprenoids can be produced. The recombinant cells as described herein can also be engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase is modulated.

Citrate Synthase Pathway

Citrate synthase catalyzes the condensation of oxaloacetate and acetyl-CoA to form citrate, a metabolite of the Tricarboxylic acid (TCA) cycle (Ner, S. et al. 1983. Biochemistry 22: 5243-5249; Bhayana, V. and Duckworth, H. 1984. Biochemistry 23: 2900-2905). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem. 15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2122). Therefore, one of skill in the art can modulate citrate synthase expression (e.g., decrease enzyme activity) to allow more carbon to flux into the mevalonate pathway, thereby increasing the eventual production of mevalonate or isoprenoids. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (pta) (Shimizu et al. 1969. Biochim. Biophys. Acta 191: 550-558) catalyzes the reversible conversion between acetyl-CoA and acetylphosphate (acetyl-P), while acetate kinase (ackA) (Kakuda, H. et al. 1994. J. Biochem. 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. Microb. Mol. Biol. Rev. 69:12-50). Without being bound by theory, since ackA-pta use acetyl-CoA, deleting those genes might allow carbon not to be diverted into acetate and to increase the yield of mevalonate or isoprenoids.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

Pathways Involving Lactate Dehydrogenase

In *E. coli*, D-Lactate is produced from pyruvate through the enzyme lactate dehydrogenase (ldhA) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production and isoprenoids production, one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

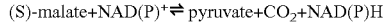

$$(S)\text{-malate} + NAD(P)^+ \rightleftharpoons \text{pyruvate} + CO_2 + NAD(P)H$$

Thus, the two substrates of this enzyme are (S)-malate and $NAD(P)^+$, whereas its 3 products are pyruvate, $CO_2$, and NADPH.

Expression of the NADP-dependent malic enzyme (maeB) (Iwikura, M. et al. 1979. J. Biochem. 85: 1355-1365) can help increase mevalonate and isoprenoid yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) J. Bact. 189:5937-5946).

As such, more starting substrate (pyruvate or acetyl-CoA) for the downstream production of mevalonate and isoprenoids can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataac-catctgcggtgataaattatctctggcg-gtgttgacataaataccactggcggt-gatactgagcacatcagcaggacgcactgaccaccatgaaggtg—lambda promoter, GenBank NC_001416), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, and pyruvate decarboxylase (aceE, aceF, and/or lpdA) is designated as F. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-F, non-limiting combinations that can be used are: AB, AC, AD, AE, AF, BC, BD, BE, BF, CD, CE, CF, DE, DF and EF. For combinations of any three of the enzymes A-F, non-limiting combinations that can be used are: ABC, ABD, ABE, ABF, BCD, BCE, BCF, CDE, CDF, DEF, ACD, ACE, ACF, ADE, ADF, AEF, BDE, BDF, BEF, and CEF. For combinations of any four of the enzymes A-F, non-limiting combinations that can be used are: ABCD, ABCE, ABCF, ABDE, ABDF, ABEF, BCDE, BCDF, CDEF, ACDE, ACDF, ACEF, BCEF, BDEF, and ADEF. For combinations of any five of the enzymes A-F, non-limiting combinations that can be used are: ABCDE, ABCDF, ABDEF, BCDEF, ACDEF, and ABCEF. In another aspect, all six enzyme combinations are used: ABCDEF.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

Other Regulators and Factors for Increased Production

Other molecular manipulations can be used to increase the flow of carbon towards mevalonate production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production of mevalonate and isoprenoids.

In other aspects, the introduction of 6-phosphogluconolactonase (PGL) into microorganisms (such as various *E. coli* strains) which lack PGL can be used to improve production of mevalonate and isoprenoids. PGL may be introduced using chromosomal integration or extra-chromosomal vehicles, such as plasmids. In other embodiments, PGL may be deleted from the genome of microorganisms (such as various *E. coli* strains) which express an endogenous PGL to improve production of isoprenoid precursors and/or isoprenoids.

Production of Isoprenoids Using SSF

Simultaneous saccharification and fermentation can be used to produce isoprenoids by using cells, which have been engineered to produce isoprenoids, as an inoculum. Generally, the cells are engineered such they produce a level and/or rate of isoprenoids at an amount that is commercially desirable, which is detailed below.

Simultaneous saccharification system allows for the production of isoprenoids more efficiently, measured by total amount of isoprenoids produced per added amount of starch, by utilizing starch under limited glucose conditions, further detailed below. Isoprenoids produced by simultaneous saccharification and fermentation at limited glucose conditions also can reduce the volatiles produced under excess glucose conditions and thus has higher purity.

Growth Conditions

The cells (e.g., aerobic or anaerobic) of any of the compositions or methods should be grown under conditions that are conducive to optimal production of isoprenoids. Considerations for optimization include cell culture media, oxygen levels, and conditions favorable for decoupling such that isoprenoids production is favored over cell growth. For aerobic cells, the cell culture conditions should be used that provide optimal oxygenation for cells to be able to produce isoprenoids.

For anaerobic cells, these cells are capable of replicating and/or producing isoprenoids in a fermentation system that is substantially free of oxygen. Thus, in one embodiment, anaerobic cells engineered to produce isoprenoids can use SSF for initial growth. In some embodiments, the fermentation system contains syngas as the carbon and/or energy source. In some embodiments, the anaerobic cells are initially grown in a medium comprising a carbon source other than syngas and then switched to syngas as the carbon source. For the cells that use syngas as a source or energy and/or carbon, the syngas includes at least carbon monoxide and hydrogen. In some embodiments, the syngas further additionally includes one or more of carbon dioxide, water, or nitrogen.

In one aspect, the amount and rate of glucose used for isoprenoids production can be controlled to maximize the production of isoprenoids. One of skill in the art should take care to monitor the amount of glucose input since too much glucose can result acetate being produced instead of isoprenoids. Accordingly, in some embodiments, limited glucose conditions are used. One of skill in the art can control the amount of glucose and glucoamylases' role in regulation of the amount of glucose. The amount of glucoamylase can be optimized to produce glucose at a rate that would keep fermentation glucose limited. Glucoamylase to starch ratio determines that rate of glucose release is more than or equal to rate of glucose utilization by isoprenoids producing cells, resulting in low or non-detectable glucose conditions. Limited glucose conditions depend on the glucose utilizing microorganism for which glucose concentration range can be 0.2 to 10 g/L. In some embodiments, the glucose concentration range can be at least about 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 g/L. In other embodiments, the glucose concentration range can be at most about 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 g/L.

Renewable resources are used for production of isoprenoids. Renewable resources refer to resources that are not fossil fuels. Generally, renewable resources are derived from living organisms or recently living organisms that can be replenished as they are consumed. Renewable resources can be replaced by natural ecological cycles or sound management practices. Non-limiting examples include biomass (e.g., switchgrass, hemp, corn, poplar, willow, sorghum, sugarcane), trees, and other plants. Non-limiting examples of renewable resources (or renewable carbon sources) include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose. As discussed above, the use of simultaneous saccharification and fermentation of any renewable resources can be used for the production of isoprenoids.

Examples of other fermentation systems and culture conditions which can be used are described in International Patent Application Publication No. WO2009/076676; U.S. Publ. 20100048964, US Publ. 2010/0086978, US Publ. 2010/0167370, US Publ. 2010/0113846, US Publ. 2010/0184178, and US Publ. 2010/0167371; U.S. Publ. 2011/0014672, U.S. Publ. 2010/0196977, and US Publ. 2011/0046422; WO 2004/033646 and WO 96/35796.

Bioreactors

A variety of different types of reactors can be used for production of isoprenoids from any renewable resource. There are a large number of different types of fermentation processes that are used commercially. The bioreactor can be designed to optimize the retention time of the cells, the residence time of liquid, and the sparging rate of any gas (e.g., syngas).

In various embodiments, the cells are grown using any known mode of fermentation, such as batch, fed-batch, continuous, or continuous with recycle processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprenoids production. In some embodiments, cells in stationary phase produce isoprenoids.

In some embodiments, a variation on the standard batch system is used, such as the Fed-Batch system. Fed-Batch fermentation processes comprise a typical batch system with the exception that the carbon source (e.g. syngas, glucose) is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., syngas, glucose, fructose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprenoids production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

Exemplary Production of Isoprenoids Composition

In some embodiments, the cells are cultured in a culture medium under conditions permitting the production of isoprenoidsby the cells in the SSF system with glucoamylase under neutral pH conditions. In some embodiments, the isoprenoid can be monoterpenes, diterpenes, triterpenes, tetraterpenes, sequiterpenes, or polyterpenes. In other embodiments, the isoprenoid can be abietadiene, amorphadiene, carene, farnesene, α-farnesene, β-farnesene, farnesol, geraniol, geranylgeraniol, linalool, limonene, myrcene, nerolidol, ocimene, patchoulol, β-pinene, sabinene, 7-terpinene, terpindene and valencene.

By "peak absolute productivity" is meant the maximum absolute amount of isoprenoids produced during the culturing of cells for a particular period of time (e.g., the culturing of cells during a particular fermentation run). By "peak absolute productivity time point" is meant the time point during a fermentation run when the absolute amount of isoprenoids produced is at a maximum during the culturing of cells for a particular period of time (e.g., the culturing of cells during a particular fermentation run). In some embodiments, the isoprenoids amount is measured at the peak absolute productivity time point. In some embodiments, the peak absolute productivity for the cells is about any of the isoprenoids amounts disclosed herein.

By "peak specific productivity" is meant the maximum amount of isoprenoids produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprenoids produced per cell is at a maximum. The peak specific productivity is determined by dividing the total productivity by the amount of cells, as determined by optical density at 600 nm ($OD_{600}$). In some embodiments, the isoprenoids amount is measured at the peak specific productivity time point. In some embodiments, the peak specific productivity for the cells is about any of the isoprenoids amounts per cell disclosed herein.

By "peak volumetric productivity" is meant the maximum amount of isoprenoids produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprenoids produced per volume of broth is at a maximum. The peak specific volumetric productivity is determined by dividing the total productivity by the volume of broth and amount of time. In some embodiments, the isoprenoids amount is measured at the peak specific volumetric productivity time point. In some embodiments, the peak specific volumetric productivity for the cells is about any of the isoprenoids amounts per volume per time disclosed herein.

By "peak concentration" is meant the maximum amount of isoprenoids produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprenoids produced per cell is at a maximum. In some embodiments, the isoprenoids amount is measured at the peak concentration time point. In some embodiments, the peak concentration for the cells is about any of the isoprenoids amounts disclosed herein.

By "average volumetric productivity" is meant the average amount of isoprenoids produced per volume of broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprenoids amounts per volume per time disclosed herein.

By "cumulative total productivity" is meant the cumulative, total amount of isoprenoids produced during the culturing of cells for a particular period of time (e.g., the culturing of cells during a particular fermentation run). In some embodiments, the cumulative, total amount of isoprenoids is measured. In some embodiments, the cumulative total productivity for the cells is about any of the isoprenoids amounts disclosed herein.

As used herein, "relative detector response" refers to the ratio between the detector response (such as the GC/MS area) for one compound (such as isoprenoids) to the detector response (such as the GC/MS area) of one or more compounds (such as all C10 or >C10 hydrocarbons) The detector response may be measured as described herein, such as the GC/MS analysis performed with an Agilent 6890 GC/MS system fitted with an Agilent HP-5MS GC/MS column (30 m×250 μm; 0.25 μm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprenoids at greater than or about 3, 4, 5, 6, 7, 8, 9, 10, 11, 12, 13, 14, 15, 16, 17, 18, 19, or 20 g/L (g isoprenoids/L broth).

In some embodiments, the cells in culture produce isoprenoids at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole of isoprenoids/gram of cells for the wet weight of the cells/hour (nmole/$g_{wcm}$/hr). In some embodiments, the amount of isoprenoids is between about 2 to about 200,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr, about 5,000 to about 10,000 nmole/$g_{wcm}$/hr, about 10,000 to about 50,000 nmole/$g_{wcm}$/hr, about 50,000 to about 100,000 nmole/$g_{wcm}$/hr, about 100,000 to about 150,000 nmole/$g_{wcm}$/hr, or about 150,000 to about 200,000 nmole/$g_{wcm}$/hr. In some embodiments, the amount of isoprenoids is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr, about 1,000 to about 5,000 nmole/$g_{wcm}$/hr, about 2,000 to about 20,000 nmole/$g_{wcm}$/hr, about 5,000 to about 50,000 nmole/$g_{wcm}$/hr, about 10,000 to about 100,000 nmole/$g_{wcm}$/hr, about 20,000 to about 150,000 nmole/$g_{wcm}$/hr, or about 20,000 to about 200,000 nmole/$g_{wcm}$/hr.

The amount of isoprenoids in units of nmole/$g_{wcm}$/hr can be measured as disclosed in U.S. Pat. No. 5,849,970, which is hereby incorporated by reference in its entirety, particularly with respect to the measurement of isoprenoids production. For example, two mL of headspace (e.g., headspace from a culture such as 2 mL of culture cultured in sealed vials at 32° C. with shaking at 200 rpm for approximately 3 hours) are analyzed for isoprenoids using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprenoids production). The gas chromatography area units are converted to nmol isoprenoids via a standard isoprenoids concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

Systems for Producing Isoprenoids

The invention also provides systems for producing isoprenoids. In one aspect, the system includes (i) a bioreactor within which saccharification and fermentation are performed at about pH 5.0 to 8.0; (ii) a host cell comprising a heterologous nucleic acid encoding an polyprenyl pyrophosphate synthase polypeptide; (iii) a glucoamylase that possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent *Rhizopus* p. glucoamylase (RhGA) comprising SEQ ID NO: 9, and a variant thereof, and wherein the variant has at least 99% sequence identity to the parent glucoamylase.

Components of the system are described herein. Various combinations of these system components are expressly contemplated within the scope of the invention.

Recovery

The isoprenoids produced by the genetically modified cells described herein can be recovered from the fermentation system using any suitable separation and purification methods known in the art, see for example US 2010/0311065, US 2007/0254354, the contents of which are expressly incorporated herein by reference.

In certain embodiments, an organic phase comprising the isoprenoid is recovered from the fermentation broth by centrifugation. In other embodiments, an organic phase comprising the isoprenoid separates from the fermentation broth spontaneously. In yet other embodiments, an organic phase comprising the isoprenoid is actively recovered from the fermentation broth by adding a deemulsifier and/or a nucleating agent into the fermentation reaction. Illustrative examples of deemulsifiers include flocculants and coagulants. Illustrative examples of nucleating agents include droplets of the isoprenoid compound itself and organic solvents such as dodecane, isopropyl myristrate, and methyl oleate.

In other embodiments, the isoprenoid can be recovered from other products that may be present in the organic phase. In certain embodiments, separation is achieved using adsorption, distillation, gas phase extraction (stripping), gas phase-liquid phase extraction (stripping), liquid phase-liquid phase extraction (solvent extraction), ultrafiltration, and standard chromatographic techniques.

The above enumerated list are only examples and one skilled in the art will be aware of a number of recovery techniques that may be appropriately used to obtain a desired end product.

Methods of Using the Recombinant Cells to Produce Isoprenoids and/or Isoprenoid Precursor Molecules Also provided herein are methods of producing isoprenoid precursor molecules and/or isoprenoids comprising culturing recombinant microorganisms (e.g., recombinant bacterial cells) that comprise a polyprenyl pyrophosphate synthase polypeptide, and one or more nucleic acids encoding a MVA pathway polypeptide including, but not limited to, AACT, HMG-CoA reductase, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IPP isomerase polypeptides, IDI polypeptides, and polypeptides (e.g., fusion polypeptides) having an activity of two or more MVA pathway polypeptides.

The isoprenoid precursor molecules and/or isoprenoids can be produced from any of the cells described herein and according to any of the methods described herein. Any of the cells can be used for the purpose of producing isoprenoid precursor molecules and/or isoprenoids from carbohydrates, including six carbon sugars such as glucose.

Thus, provided herein are methods of making isoprenoid precursor molecules and/or isoprenoids comprising culturing recombinant cells (e.g., bacterial cell) comprising a polyprenyl pyrophosphate synthase polypeptide, and one or more heterologous nucleic acids encoding a AACT, HMG-CoA reductase and HMG-CoA synthase, in a suitable condition for producing isoprenoids and producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the bacterial cells can be any of the cells described herein. Any of the polyprenyl pyrophosphate synthase or variants thereof described herein, any of the bacterial strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

The instant methods for the production of isoprenoid precursor molecules and/or isoprenoids can produce at least 5% greater amounts of isoprenoid precursors and/or isoprenoids when compared to isoprenoids and/or isoprenoid precursor-producing recombinant cells (e.g., bacterial cells) that have not been engineered for increased carbon flux to mevalonate production. Alternatively, the bacterial cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive. In some aspects, the method of producing isoprenoid precursor molecules and/or isoprenoids further comprises a step of recovering the isoprenoid precursor molecules and/or isoprenoids.

Provided herein are methods of using any of the cells described above for enhanced isoprenoid and/or isoprenoid precursor molecule production. The production of isoprenoid precursor molecules and/or isoprenoids by the cells can be enhanced by the any of the methods disclosed herein for increasing carbon flow through the MVA and/or DXP pathway, and one or more heterologous nucleic acids encoding a polyprenyl pyrophosphate synthase polypeptide. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have not been engineered. The production of isoprenoid precursor molecules and/or isoprenoids can be enhanced by about 5% to about 1,000,000 folds. The production of isoprenoid precursor molecules and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursor molecules and/or isoprenoids by cells which have not been engineered for increased carbon flux to mevalonate production.

The production of isoprenoid precursor molecules and/or isoprenoids can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursor molecules and/or isoprenoids by cells which have not been engineered for increased carbon flux to mevalonate production.

In addition, more specific cell culture conditions (e.g., SSF) can be used to culture the cells in the methods described herein. In some aspects, the method of producing mevalonate further comprises a step of recovering the isoprenoid precursor molecules and/or isoprenoids.

Simultaneous Saccharification and Fermentation (SSF)

During SSF, the hydrolyzing enzymes are added along with the end product producer, commonly a microorganism. Enzymes release lower molecule sugars, i.e., fermentable sugars DP1-3, from the starch substrate, while the microorganism simultaneously uses the fermentable sugars for growth and production of the end product. Typically, fermentation conditions are selected that provide an optimal pH and temperature for promoting the best growth kinetics of the producer host cell strain and catalytic conditions for the enzymes produced by the culture. See e.g., Doran et al., *Biotechnol. Progress* 9: 533-538 (1993). Table 1 presents exemplary fermentation microorganism and their optimal pH for fermentation. Because the glucoamylases disclosed herein possess significant activity at a neutral pH and an elevated temperature, they would be useful in the SSF for those microorganisms having an optimal fermenting pH in the range of 5.5 to 7.5.

TABLE 1

Exemplary fermentation organisms and their optimal pH.

| End products | Fermentation Organisms | Optimal pH of the fermentation |
|---|---|---|
| Lysine and salts thereof | Corynebacterium glutamicum | 6.8-7.0 |
| | Bacillus lacterosprous | 7.0-7.2 |
| | Methylophilotrophus | 7 |
| Lactic Acid | Lactobacillus amylophilus | 6.0-6.5 |
| | Bacillus coagulans | 6.4-6.6 |
| | Bacillus thermoamylovorans | 5.0-6.5 |
| | Bacillus smithii | 5.0-6.5 |
| | Geobacillus stearothermophilus | 5.0-6.5 |
| Monosodium Glutamate (MSG) | Corynebacterium pekinense | 7 |
| | Corynebacterium crenatum | 7 |
| | Brevibacterium tianjinese | 7 |
| | Corynebacterium glutamicum HU7251 | 7.0-7.2 |
| | Arthrobacter sp | 7 |
| Succinic acid | Escherichia coli | 6.0-7.5 |
| 1,3-Propanediol | Escherichia coli | 6.5-7.5 |
| 2-Keto-gulonic acid | Escherichia coli | 5.0-6.0 |
| Isoprene | Escherichia coli | 6-8 |

EXAMPLES

Methods Used in the Examples

The following materials, assays, and methods were used in the examples provided below:

HPLC Method to Measure Saccharide Composition

The composition of the reaction products of oligosaccharides was measured by a HPLC system (Beckman System Gold 32 Karat Fullerton, Calif.). The system, maintained at 50° C., was equipped with a Rezex 8 u8% H Monosaccharides column and a refractive index (RI) detector (ERC-7515A, Anspec Company, Inc.). Diluted sulfuric acid (0.01 N) was applied as the mobile phase at a flow rate of 0.6 ml/min. 20 µl of 4.0% solution of the reaction mixture was injected onto the column. The column separates saccharides based on their molecular weights. The distribution of saccharides and the amount of each saccharide were determined from previously run standards.

Determination of Glucoamylase Activity Units (GAU)

Glucoamylase activity units (GAU) were determined based on the activity of a glucoamylase enzyme to catalyze the hydrolysis of p-nitrophenyl-alpha-D-glucopyranoside (PNPG) to glucose and p-nitrophenol. At an alkaline pH, p-nitrophenol forms a yellow color that is measured spectrophotometrically at 405 nm. The amount of p-nitrophenol released correlates with the glucoamylase activity.

Protein Concentration Determination

The protein concentration in a sample was determined using the Bradford QuickStart™ Dye Reagent (Bio-Rad, California, USA). For example, a 10 μL sample of the enzyme was combined with 200 μL Bradford QuickStart™ Dye Reagent. After thorough mixing, the reaction mixture was incubated for at least 10 minutes at room temperature. Air bubbles were removed and the optical density (OD) was measured at 595 nm. The protein concentration was then calculated using a standard curve generated from known amounts of bovine serum albumin.

Purification of HgGA for Characterization Studies

The material concentrated by ultrafiltration (UFC) was desalted/buffer-exchanged using a BioRad DP-10 desalting column and 25 mM Tris pH 8.0. 100 mg of total protein was applied to a Pharmacia Hi Prep 16/10 S Sepharose FF column, which was equilibrated with the above buffer at 5 ml/min. Glucoamylase was eluted with a 4-column volume (CV) gradient buffer containing 0-200 mM NaCl. Multiple runs were performed and the purest fractions, as determined via SDS-PAGE/coomassie blue staining analysis, were pooled and concentrated using VivaSpin 10K MWCO 25 ml spin tubes. The final material was passed over a Novagen H isBind 900 chromatography cartridge that had been washed with 250 mM EDTA and rinsed with above buffer. 2 ml of final material was obtained, having a protein concentration of 103.6 mg/ml, and a glucoamylase activity of 166.1 GAU/ml (determined by a PNPG based assay). Specific activities were determined using a standardized method using p-nitrophenyl-alpha-D-glucopyranoside (PNPG) as a substrate and reported in GAU units.

Determination of Glucose Concentration

Glucose concentration in a saccharification reaction mixture was determined with the ABTS assay. Samples or glucose standards in 5 μL were placed in wells of a 96-well microtiter plate (MTP). Reactions were initiated with the addition of 95 μL of the reactant containing 2.74 mg/ml 2,2'-Azino-bis(3-ethylbenzothiazoline-6-sulfonic acid) diammonium salt (ABTS) (Sigma P1888), 0.1 U/ml horseradish peroxidase type VI (Sigma P8375), and 1 U/ml glucose oxidase (Sigma G7141). $OD_{405\ nm}$ was immediately monitored at a 9-second interval for 300 seconds using a Spectramax plate reader. Because the rate of $OD_{405\ nm}$ increase is proportional to the glucose concentration, the sample's glucose concentration was determined by comparing with the glucose standard, and was reported as mg/ml.

Example 1

Comparison of the pH and Activity Profiles of Various Glucoamylases at 32° C.

The pH and activity profiles of glucoamylases (GAs) from *Humicola grisea* (HgGA), *Trichoderma reesei* (TrGA), *Aspergillus niger* (AnGA) and *Talaromyces emersonii* (TeGA) were determined at 32° C. As the substrate, 8% potato starch (Sigma Cat. No. 52630) was solubilized by heating. A series of citrate/phosphate buffers at 0.25 or 0.5 pH increments, ranging from pH 2.0 to 8.0, were prepared. Purified enzymes were diluted to 0.1 or 0.02 GAU/ml in water (TeGA was dosed at 0.2 GAU/ml). HgGA, TrGA, AnGA, and TeGA were dosed at 0.0125, 0.0076, 0.0109, and 0.0055 mg/ml, respectively. 10 μL buffer of various pH was placed in 0.2 ml PCR tube strips (AB Gene, Cat. No. AB-0451, 800-445-2812) with 15 μL of diluted enzyme. The reactions were initiated by the addition of 25 μL soluble potato starch. The reactions were incubated on a PCR type thermocycler heating block for exactly ten minutes, then terminated by the addition of 10 μL 0.5 M NaOH. The glucose released in the reaction was determined using the ABTS assay, and the glucoamylase activities were determined. The pH and activity profiles are presented in Table and FIG. 1 as the percentage of the maximum activity for each glucoamylase.

TABLE 2 pH profiles of HgGA, TrGA, AnGA, and TeGA at 32° C.
The values represent % of the maximum activity for each enzyme.

| pH | HgGA | TrGA | AnGA | TeGA |
|---|---|---|---|---|
| 2.00 | 45 | 56 | 91 | 93 |
| 2.50 | 54 | 67 | 91 | 97 |
| 2.75 | 60 | 72 |  | 100 |
| 3.00 | 63 | 81 | 98 | 98 |
| 3.25 | 71 | 91 | 100 | 95 |
| 3.50 | 77 | 99 | 99 | 88 |
| 3.75 | 84 | 100 | 96 | 79 |
| 4.00 | 93 |  | 84 | 64 |
| 4.25 | 100 | 95 | 78 | 51 |
| 4.50 | 84 |  | 55 | 34 |
| 4.75 | 44 |  | 46 | 30 |
| 5.00 | 40 |  | 45 | 29 |
| 5.25 | 42 | 66 | 43 | 27 |
| 5.50 | 46 |  | 41 | 23 |
| 5.75 | 48 | 58 | 39 | 21 |
| 6.00 | 53 | 51 | 35 | 17 |
| 6.50 | 62 | 38 | 27 | 11 |
| 7.00 | 67 | 22 | 17 | 5 |
| 7.50 | 58 | 10 | 7 | 2 |
| 8.00 | 39 | 4 | 3 | 1 |

As shown in Table 2 and FIG. 1, both TeGA and AnGA exhibited significantly reduced activity in the pH range of 6.0 to 8.0. At a pH 5.0 or above, TeGA retained no more than 29% activity relative to its maximum activity. At a pH 6.0 or above, TeGA retained no more than 17% activity relative to its maximum activity. Similarly, at a pH 6.0 of 6.0 or above, AnGA displayed no more than 35% activity relative to its maximum activity. In the pH range of 6.0 to 7.5, HgGA retained at least 53% activity relative to its maximum activity. At pH 6.0, TrGA also displayed at least 50% activity relative to its maximum activity. The above observation shows that both HgGA and TrGA are suitable for producing fermentable sugars at a neutral pH range (as described herein for neutral pH glucoamylases) under fermentation conditions.

Example 2

Comparison of Hydrolysis of Solubilized Starch at 32° C., pH 7.0

The ability of various glucoamylases to hydrolyze solubilized starch substrate (liquefact) at a neutral pH was compared. Corn starch was liquefied by following a conventional high-temperature jet cooking process using CLEAR- FLOW™ AA to a liquefact of DE 12-15. Saccharification of the liquefact (25% DS) was carried out using TrGA, HgGA, and AnGA at 1.0 GAU/g ds at 32° C., pH 7.0. Samples were withdrawn at different time intervals during the saccharification and subject to HPLC analysis. The composition of the oligosaccharides is presented in Table 3.

TABLE 3

Composition of oligosaccharides in saccharification.

| GA | Time (hr) | % Sugars, pH 7.0, 32° C. | | | |
|---|---|---|---|---|---|
| | | DP1 | DP2 | DP3 | Higher Sugars |
| HgGA | 0 | 0.36 | 3.59 | 7.75 | 88.30 |
| | 2 | 51.10 | 10.20 | 6.87 | 31.85 |
| | 5.25 | 64.90 | 11.80 | 0.13 | 23.13 |
| | 21.25 | 89.30 | 1.10 | 0.30 | 9.34 |
| | 25.25 | 91.20 | 0.98 | 0.23 | 7.61 |
| | 29.25 | 92.60 | 0.90 | 0.31 | 6.12 |
| | 45.25 | 96.50 | 1.15 | 0.12 | 2.26 |
| TrGA | 0 | 0.36 | 3.59 | 7.75 | 88.30 |
| | 2 | 38.06 | 7.49 | 9.10 | 45.35 |
| | 5.25 | 47.17 | 9.92 | 6.13 | 36.78 |
| | 21.25 | 69.43 | 8.33 | 0.17 | 22.07 |
| | 25.25 | 71.69 | 7.14 | 0.17 | 21.01 |
| | 29.25 | 73.57 | 6.16 | 0.18 | 20.09 |
| | 45.25 | 79.19 | 3.45 | 0.20 | 17.15 |
| AnGA | 0 | 0.36 | 3.59 | 7.75 | 88.30 |
| | 2 | 14.12 | 4.57 | 8.88 | 72.43 |
| | 5.25 | 28.38 | 8.01 | 10.30 | 53.31 |
| | 21.25 | 58.97 | 11.49 | 0.28 | 29.26 |
| | 25.25 | 60.94 | 10.53 | 0.28 | 28.25 |
| | 29.25 | 62.82 | 9.54 | 0.23 | 27.41 |
| | 45.25 | 74.14 | 4.08 | 0.24 | 21.54 |

Using HgGA, the DP1 content reached more than 90% after 24 hrs. After 45 hours, the DP1 content reached more than 96%, while the content of higher sugars decreased to less than 3%. Using TrGA, more than 70% DP1 was obtained after 24 hours. After 45 hours, the DP1 content reaches about 80%, while the content of higher sugars dropped to less than 20%. For AnGA, less than 75% of DP1 was obtained after 45 hours, while higher sugars remained more than 20%. The data in Table 3 indicate that both HgGA and TrGA are more effective than AnGA to hydrolyze solubilized starch to glucose, at a neutral pH.

Example 3

Comparison of Hydrolysis of Liquefied Starch at 58° C., pH 6.5

Corn starch liquefact (-9.1DE) obtained by SPEZYME® FRED (Danisco US Inc., Genencor Division) treatment was adjusted to pH 6.5 with NaOH and equilibrated at a 58° C. water bath. AnGA (OPTIDEX™ L-400, Danisco US Inc., Genencor Division), TrGA, and HgGA were added at 0.5 GAU/g ds to each flask containing corn starch liquefact. Saccharification was carried out up to 48 hours with periodical sampling for HPLC analysis. 0.5 mL enzyme-deactivated sample was diluted with 4.5 ml of RO water. The diluted sample was then filtered through 0.45 μm Whatman filters and subject to HPLC analysis. The HPLC analysis was conducted as described in Methods used in the Examples. The composition of the oligosaccharides is presented in Table 4.

TABLE 4

Composition of oligosaccharides in saccharification.

| | Hour | Percent Sugar Composition | | | |
|---|---|---|---|---|---|
| | | % DP1 | % DP2 | % DP3 | % HS |
| Liquefact | 0 | 0.49 | 3.02 | 5.52 | 90.98 |
| HgGA | 2 | 60.66 | 8.87 | 1.93 | 28.17 |
| | 4 | 69.92 | 7.43 | 0.69 | 21.75 |
| | 6 | 75.96 | 5.80 | 0.38 | 17.85 |
| | 7.7 | 77.56 | 5.15 | 0.47 | 16.35 |
| | 14 | 84.31 | 2.96 | 0.42 | 11.57 |
| | 23.5 | 88.70 | 2.20 | 0.43 | 8.67 |
| | 31.5 | 90.01 | 1.87 | 0.40 | 6.90 |
| | 48 | 93.67 | 1.49 | 0.33 | 4.51 |
| TrGA | 2 | 37.08 | 10.19 | 5.06 | 47.47 |
| | 4 | 49.25 | 12.12 | 2.12 | 36.42 |
| | 6 | 55.30 | 12.16 | 1.09 | 31.10 |
| | 7.7 | 58.06 | 11.74 | 0.76 | 29.12 |
| | 14 | 63.83 | 9.96 | 0.46 | 25.28 |
| | 23.5 | 68.52 | 8.18 | 0.53 | 22.77 |
| | 31.5 | 70.35 | 7.24 | 0.54 | 21.32 |
| | 48 | 75.25 | 5.48 | 0.50 | 18.37 |
| AnGA | 2 | 41.33 | 11.83 | 4.40 | 42.20 |
| | 4 | 50.08 | 12.95 | 1.60 | 35.04 |
| | 6 | 53.32 | 12.70 | 0.83 | 33.16 |
| | 7.7 | 54.80 | 12.41 | 0.62 | 31.91 |
| | 14 | 58.85 | 11.20 | 0.40 | 29.15 |
| | 23.5 | 61.70 | 10.44 | 0.46 | 27.41 |
| | 31.5 | 62.34 | 10.11 | 0.50 | 26.58 |
| | 48 | 64.23 | 9.83 | 0.59 | 25.01 |

Using HgGA, the DP1 content reached more than 90% after 24 hrs. After 48 hours, the DP1 content reached more than 93%, while the content of higher sugars decreased to less than 5%. Using TrGA, more than 70% DP1 was obtained after 24 hours. After 45 hours, the DP1 content reaches about 75%, while the content of higher sugars dropped to about 18%. For AnGA, less than 65% of DP1 was obtained after 45 hours, while higher sugars remained more than 25%. The data in Table 4 indicate that both HgGA and TrGA are more effective than AnGA, at a neutral pH and 58° C., to hydrolyze solubilized starch to glucose. This observation is consistent with data presented in Table 3, where saccharification was performed at 32° C.

Example 4

Comparison of High Sugars (DP4+) Reduction at 58° C., pH 6.5

Various concentrations of AnGA, TrGA, and HgGA were used to saccharify a starch substrate at 58° C., pH 6.5, and the reduction of high sugars (DP4+) was compared. The starch substrate was a 25% cornstarch liquefact, which was liquefied by SPEZYME® FRED (Danisco US Inc., Genencor Division). Glucoamylases were added as shown in Table 5, from 0.25 GAU/gds to 10.0 GAU/gds. The saccharification reaction was conducted at 58° C., pH 6.5. Samples were withdrawn at various time points and the sugar composition was determined by HPLC analysis. The composition of the oligosaccharides is presented in Table 5 and FIG. 2.

TABLE 5

Composition of oligosaccharides in saccharification.

| Glucoamylase | GAU/gds starch | Percent Sugar Composition at 48 hr | | | |
|---|---|---|---|---|---|
| | | DP1 | DP2 | DP3 | DP4+ |
| AnGA | 1 | 64.25 | 5.10 | 0.00 | 30.65 |
| | 2.5 | 73.36 | 1.74 | 0.41 | 24.49 |
| | 5 | 81.26 | 1.05 | 0.46 | 17.22 |
| | 7.5 | 85.53 | 1.48 | 0.44 | 12.13 |
| | 10 | 89.32 | 2.03 | 0.42 | 8.22 |
| TrGA | 1 | 81.10 | 2.28 | 0.49 | 16.13 |
| | 2 | 86.65 | 1.99 | 0.49 | 10.87 |
| | 3 | 90.36 | 2.86 | 0.49 | 8.30 |
| | 4 | 90.48 | 3.17 | 0.52 | 5.83 |
| | 5 | 90.95 | 3.96 | 0.61 | 4.48 |
| HgGA | 0.25 | 93.15 | 2.10 | 1.00 | 3.76 |
| | 0.5 | 95.33 | 2.58 | 0.64 | 1.45 |
| | 0.75 | 95.08 | 3.36 | 0.53 | 1.02 |
| | 1 | 94.57 | 3.94 | 0.56 | 0.94 |

Figure 2:
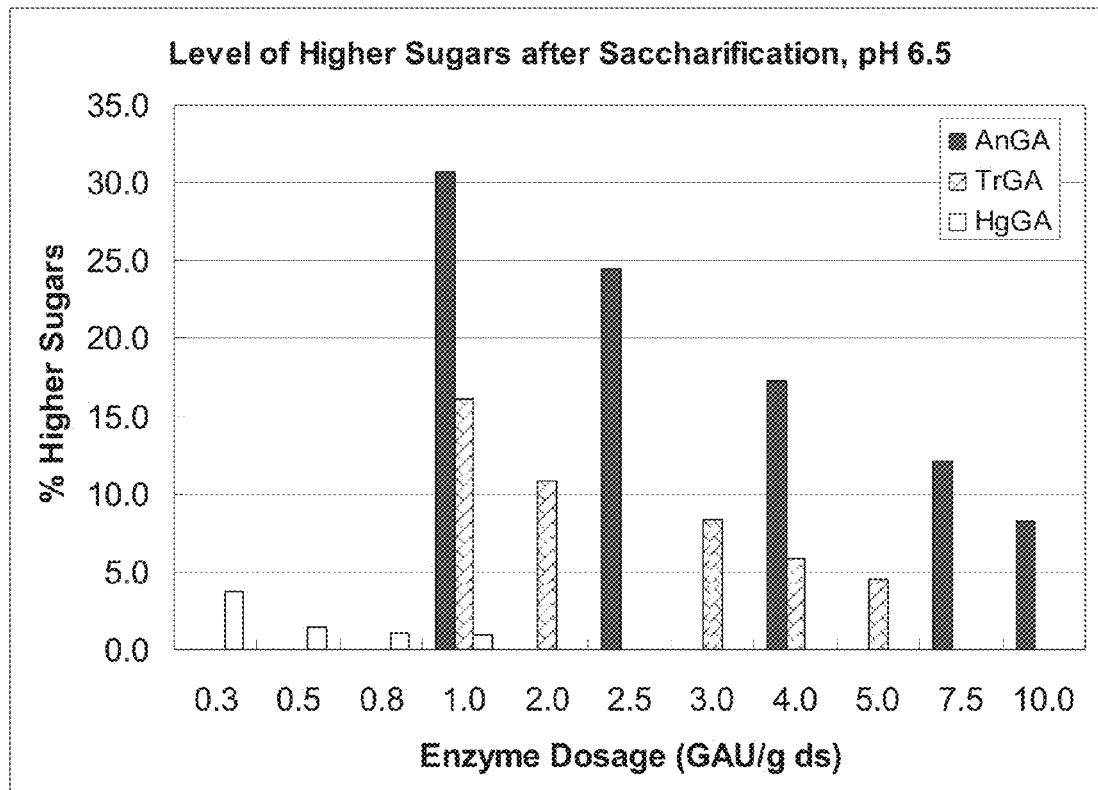
FIG. 2 depicts the presence of higher sugars after 48-hour saccharification reactions catalyzed by HgGA, TrGA, and AnGA. The saccharification reactions are described in Example 4.

The results presented in Table 5 and FIG. 2 indicated that AnGA resulted in more than 8% of higher sugars (DP4+), at 58° C., pH 6.5, even at a high dosage of glucoamylase, 10.0 GAU/gds. In contrast, lower than 5% of higher sugars (DP4+) was observed for 5 GAU/gds TrGA. HgGA resulted in the lowest levels of higher sugars (DP4+). For example, at 0.5 GAU/gds HgGA, the saccharification mixture contained less than 1.5% of higher sugars (DP4+), which is comparable to the resulted obtained under the current industrial high glucose processing conditions (pH 4.5, 60° C.) using AnGA.

Example 5

Continuous Production of Glucose from Granular Cassava Starch by HgGA at a Neutral pH The capability of HgGA to convert granular unmodified cassava starch to glucose and short chain glucose polymers at a neutral pH was further characterized. A 27% dry substance aqueous slurry of cassava starch was first adjusted to pH 6.4 with sodium carbonate. SPEZYME™ Alpha (Danisco US Inc., Genencor Division) was added at 2 AAU/g ds, and HgGA was added at 1 GAU/g ds. The reaction was carried out for 48 hours at 58° C. with continuous stirring. At selected time intervals, samples of the slurry were removed. The removed sample was added to a 2.5 ml micro-centrifuge tube and centrifuged for 4 minutes at 13,000 rpm. Refractive index (RI) of the supernatant was determined at 30° C. The remaining supernatant was filtered through a 13 mm syringe filter with a 0.45 μm GHP membrane into a 2.5 ml micro-centrifuge tube and boiled for 10 minutes to terminate the amylase activity. 0.5 mL enzyme-deactivated sample was diluted with 4.5 ml of RO water. The diluted sample was then filtered through 0.45 μm Whatman filters and subject to HPLC analysis. The HPLC analysis was conducted as described in Methods used in the Examples.

The total dry substance was determined by taking about 1 ml of the starch slurry into a 2.5 ml spin tube, adding 1 drop of SPEZYME® FRED (Danisco US Inc., Genencor Division) from a micro dispo-pipette, and boiling 10 minutes. Refractive index at 30° C. was determined. The dry substance of the supernatant and the whole sample (total) was determined using appropriate DE tables. The CRA 95 DE Table was used for the supernatant and corrected for consumption of water of hydrolysis. % soluble was calculated as: 100×(the dry substance of the supernatant)/(the total dry substance). The composition of the oligosaccharides is presented in Table 6.

TABLE 6

Saccharide distribution for HgGA-mediated saccharification of cassava granular starch.

| Hrs | Saccharide Distribution | | | | |
|---|---|---|---|---|---|
| | DP1 | DP2 | DP3 | DP4+ | Soluble % |
| 2.50 | 93.799 | 1.726 | 0.499 | 3.976 | 56.20 |
| 7.50 | 96.166 | 1.551 | 0.480 | 1.802 | 78.80 |
| 12.00 | 96.731 | 1.639 | 0.411 | 1.220 | 85.10 |
| 23.50 | 96.928 | 2.204 | 0.326 | 0.541 | 92.80 |
| 48.00 | 96.772 | 3.023 | 0.205 | 0.000 | 99.00 |

As shown in Table 6, the reaction achieved about 93% solubility and yielded about 96.9% glucose within 24 hours. Continuation of saccharification resulted in 99% solubility and about 96.8% glucose after 48 hours.

Example 6

Continuous Production of Glucose from Granular Cornstarch by HgGA at a Neutral pH Corn granular starch was used to characterize HgGA. The experiments were carried out using 32% ds corn granular starch. Water (64.44 g) and starch (35.56 g; at 90% ds) were mixed and the pH of the slurry was increased to 6.4. The starch slurry was placed in a water bath maintained at 58° C. and enzymes were added. The enzymes included SPEZYME™ Alpha (Danisco US Inc., Genencor Division) and HgGA. The starch slurry was maintained at 58° C. for 48 hrs and samples were drawn at 3, 6, 10, 24, 32, and 52 hrs to analyze the % soluble and saccharide profile. The results are presented in Table 7.

TABLE 7

Saccharide distribution for HgGA-mediated saccharification of corn granular starch

| HgGA (GAU/g ds) | Alpha-amylase (AAU/g ds) | hour | % Soluble | DP1 | DP2 | DP3+ |
|---|---|---|---|---|---|---|
| 1 | 2 | 3 | 56.82 | 94.74 | 1.57 | 3.69 |
| | | 6 | 69.45 | 95.52 | 1.76 | 2.61 |
| | | 10 | 75.96 | 96.50 | 1.79 | 1.43 |
| | | 24 | 91.50 | 95.72 | 2.79 | 0.93 |
| | | 32 | 92.71 | 95.50 | 3.08 | 0.86 |
| | | 52 | 99.66 | 93.94 | 4.42 | 0.67 |
| 0.75 | 2 | 3 | 53.35 | 92.74 | 2.00 | 5.25 |
| | | 6 | 65.87 | 94.69 | 1.77 | 3.43 |
| | | 10 | 73.11 | 95.80 | 1.73 | 2.12 |
| | | 24 | 89.09 | 95.70 | 2.53 | 1.59 |
| | | 32 | 91.01 | 95.75 | 2.64 | 1.01 |
| | | 52 | 98.65 | 95.44 | 3.44 | 1.12 |
| 0.5 | 2 | 3 | 49.06 | 88.36 | 3.36 | 8.29 |
| | | 6 | 61.98 | 92.48 | 2.18 | 5.35 |
| | | 10 | 68.18 | 94.08 | 1.90 | 3.67 |
| | | 24 | 84.14 | 95.56 | 2.03 | 2.23 |
| | | 32 | 87.90 | 95.49 | 2.25 | 2.11 |
| | | 52 | 95.17 | 95.30 | 2.81 | 1.12 |
| 0.25 | 2 | 3 | 44.01 | 75.08 | 9.16 | 15.76 |
| | | 6 | 53.92 | 84.31 | 5.25 | 10.45 |
| | | 10 | 60.97 | 88.25 | 3.72 | 7.81 |
| | | 24 | 76.63 | 93.11 | 2.25 | 4.48 |
| | | 32 | 80.00 | 93.66 | 2.17 | 4.05 |
| | | 52 | 88.37 | 94.55 | 2.31 | 2.89 |

As shown in Table 7, HgGA maintains a significant amount of glucoamylase activity for 52 hrs at pH 6.4, evidenced by the continued production of DP1 and DP2, as well as the continued increase of % soluble solids. The data also suggest that the rates of DP1 production and % solubilization of granular starch depend on the amount of HgGA. An increased amount of HgGA resulted in increased rates of % solubilization and DP1 production.

Example 7

Figure 3:
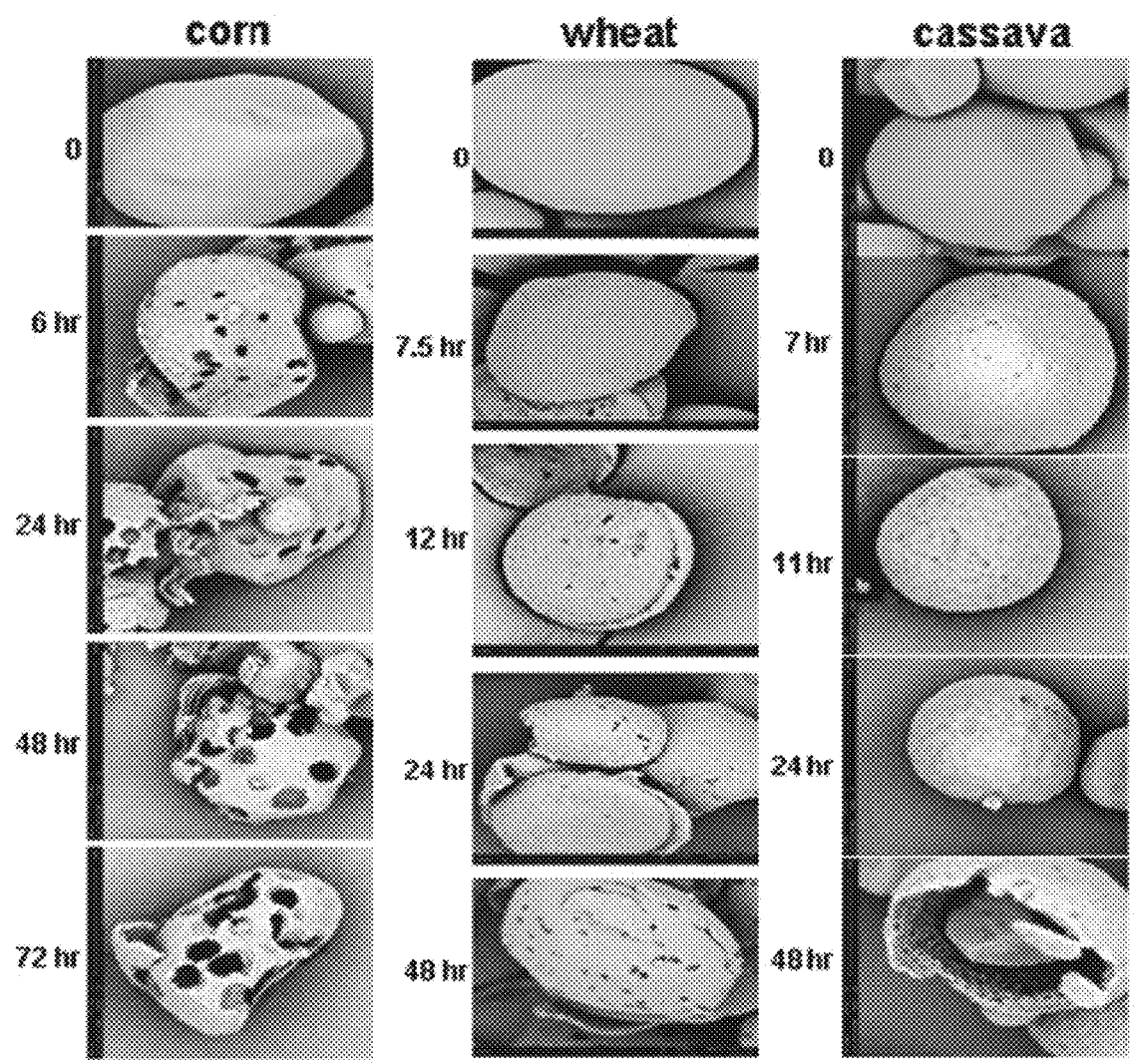
FIG. 3 depicts scanning electron micrographs of corn, wheat, and cassava starch treated with HgGA and an alpha-amylase at pH 6.4. Starch samples are hydrolyzed by HgGA and an alpha-amylase under the conditions as described in Example 7.

Characterization of Granular Starch Hydrolysis by HgGA and SPEZYME™ Alpha at a Neutral pH by Scanning Electron Microscopy Granular starch from corn, wheat, and cassava was treated with HgGA and SPEZYME™ Alpha. A 28% dry substance aqueous slurry of granular starch was first adjusted to pH 6.4 with sodium carbonate. SPEZYME™ Alpha (Danisco US Inc., Genencor Division) was added at 2 AAU/g ds, and HgGA was added at 1 GAU/g ds. Treatment was carried out at 58° C. with continuous stirring. Samples of the slurry were removed at various time points and subject to scanning electron microscopy (SEM). Slurry samples were laid on SEM sample stubs using double-sided carbon tape. Excess sample was removed by gently dusting the mounted sample with compressed air. Mounted samples were sputter coated with gold (15 nm) for 2 min at 25 mV, using an Emitech K550 Sputter Coater (Squorum Technologies). The scanning electron micrographs are presented in FIG. 3. Before treatment, starch surface was smooth and homogenous. Upon HgGA and SPEZYME™ Alpha treatment, the surface morphology of the granules changed over time. The enzyme blend first created small dimples (0.2-0.5 µm in diameter) on the surface of the starch granules. Quantity and size of the dimples increased over time. At a late stage of the treatment, for example, 48 hours for cassava granular starch, empty shells were spotted. Micrographs of empty shells indicated a complete digestion of the interior of the granule. The mechanism of enzymatic action appears to be starch granule surface peeling. Once the surface has been weakened by external peeling, the amylases penetrate and hydrolyze the interior of the granule (i.e., amylolysis) leaving hollowed out shells.

Example 8

Isoprene Production by Fermentation 8.1. Materials and Methods

Medium Recipe (per liter fermentation medium): $K_2HPO_4$ 7.5 g, $MgSO_4.7H_2O$ 2 g, citric acid monohydrate 2 g, ferric ammonium citrate 0.3 g, yeast extract 0.5 g, 1000×Modified Trace Metal Solution 1 ml. All of these components were dissolved in 60 mL DI $H_2O$ to form "Component A." The following various starch substrates (each contained about 270 g starch) were prepared:

1) Granular cornstarch (270 g) was added to 705 ml DI $H_2O$ and incubated at 34° C. for 30 minutes with agitation. The temperature was then increased to 60° C. and held for an additional 12 hours;
2) Granular endosperm 329 g (82% starch g/g) was added to 646 ml $H_2O$ and incubated at 34° C. for 30 minutes with agitation. The temperature was then increased to 60° C. and held for an additional 12 hours;
3) Granular ground corn 397 g (68% starch g/g) was added to 646 ml $H_2O$ and incubated at 34° C. for 30 minutes with agitation. The temperature was then increased to 60° C. and held for an additional 12 hours;
4) 758 g liquefact corn starch (35.6% dry solids);
5) 950 g liquefact endosperm (28.4% starch g/g and 41.3% dry solids); and
6) 950 g liquefact ground corn (28.4% starch g/g, and 39.7% dry solids).

For substrates 1), 2) and 3), a slurry was treated at 60° C. for 12 hours. Component A was heat sterilized (123° C. for 20 minutes) and allowed to cool to 25° C. Both medium solutions were then considered sterile and combined. For substrates 4), 5), and 6), a substrate was mixed with Component A, and the mixture was heat sterilized (123° C. for 20 minutes) and allowed to cool to 25° C.

Subsequently, the pH was adjusted to 7.0 with ammonium hydroxide (28%) and q.s. to volume. Mercury Vitamin Solution (8 mL) and antibiotics were added after solution had been cooled to 34° C.

1000× Modified Trace Metal Solution (per liter): Citric Acid•$H_2O$ 40 g, $MnSO_4.H_2O$ 30 g, NaCl 10 g, $FeSO_4.7H_2O$ 1 g, $CoCl_2.6H_2O$ 1 g, $ZnSO_4.7H_2O$ 1 g, $CuSO_4.5H_2O$ 100 mg, $H_3BO_3$ 100 mg, $NaMoO_4.2H_2O$ 100 mg. Each component was dissolved one at a time in DI $H_2O$, pH was adjusted to 3.0 with HCl or NaOH, and then the solution was q.s. to volume and filter sterilized with a 0.22 micron filter.

Mercury Vitamin Solution (per liter): Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in DI $H_2O$, pH was adjusted to 3.0 with HCl or NaOH, and then the solution was q.s. to volume and filter sterilized with 0.22 micron filter.

The fermentation was performed in a 1.7-L bioreactor with *E. coli* BL21 cell strain MD09-317: t pgl FRT-PL.2-mKKDyI, pCLUpper (pMCM82) (Spec50), pTrcAlba (MEA)mMVK (pDW34) (Carb50). Further information may be found in references cited herein. The experiment was carried out to monitor isoprene formation from the desired starch substrate at the desired fermentation pH 6.5 and temperature 34° C. A frozen vial of the *E. coli* strain was thawed and inoculated into tryptone-yeast extract medium. After the inoculum grew to optical density 1.0, measured at 550 nm ($OD_{550}$), 40 mL was used to inoculate a 1.7-L bioreactor and bring the initial tank volume to 0.7 L.

8.2. Isoprene Producing by Simultaneous Saccharification and Fermentation (SSF) from Various Starch Substrates with the Combination of the *Trichoderma reesei* Glucoamylase and an Alpha-amylase Starch hydrolysis was initiated at cell inoculation (time zero) by adding 8 GAU/L *Trichoderma reesei* glucoamylase (TrGA) and 404 AAU/L of SPEZYME™ Alpha (Danisco US Inc., Genencor Division). Additional enzymes were added in amounts shown in Table 8 in order to obtain a starch hydrolysis rate that roughly matched the glucose consumption rate of the cells.

TABLE 8

| Amount of enzymes added to the bioreactor over time | | | | |
| --- | --- | --- | --- | --- |
| | Amount added | | Cumulative amount added | |
| Time hr | TrGA GAU/L broth | Spezyme Alpha AAU/L broth | TrGA GAU/L broth | Spezyme Alpha AAU/L broth |
| 0.0 | 8 | 404 | 8 | 404 |
| 4.1 | 8 | 404 | 16 | 808 |
| 7.0 | 67 | 3381 | 83 | 4189 |

TABLE 8-continued

Amount of enzymes added to the bioreactor over time

| | Amount added | | Cumulative amount added | |
|---|---|---|---|---|
| Time hr | TrGA GAU/L broth | Spezyme Alpha AAU/L broth | TrGA GAU/L broth | Spezyme Alpha AAU/L broth |
| 11.3 | 132 | 6677 | 215 | 10866 |
| 12.5 | 213 | 10726 | 428 | 21593 |
| 16.7 | 210 | 10596 | 638 | 32188 |

At various time points of the SSF, samples were taken out and subjected to analysis. Similar results were obtained for the variety of starch substrates used. Representative data are presented in FIGS. 4-7.

Figure 4:
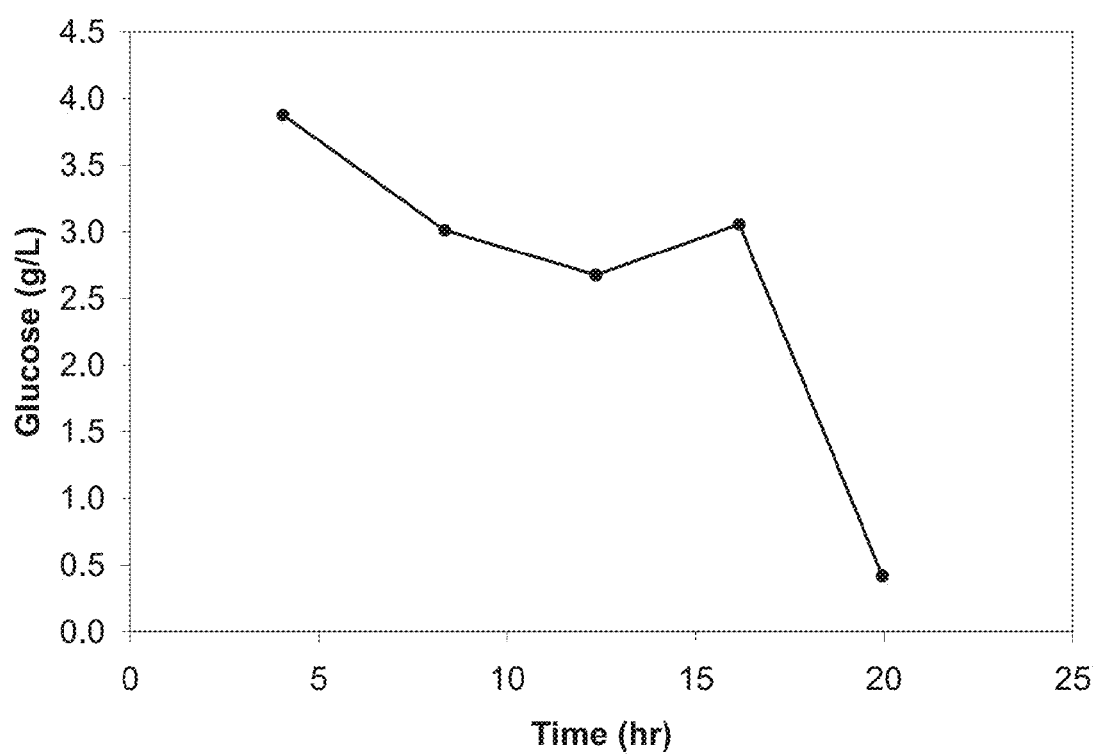
FIG. 4 depicts the time course of accumulated glucose levels during isoprene production. The simultaneous saccharification and fermentation process was carried with TrGA and an alpha-amylase as described in Example 8.2.
Figure 5:
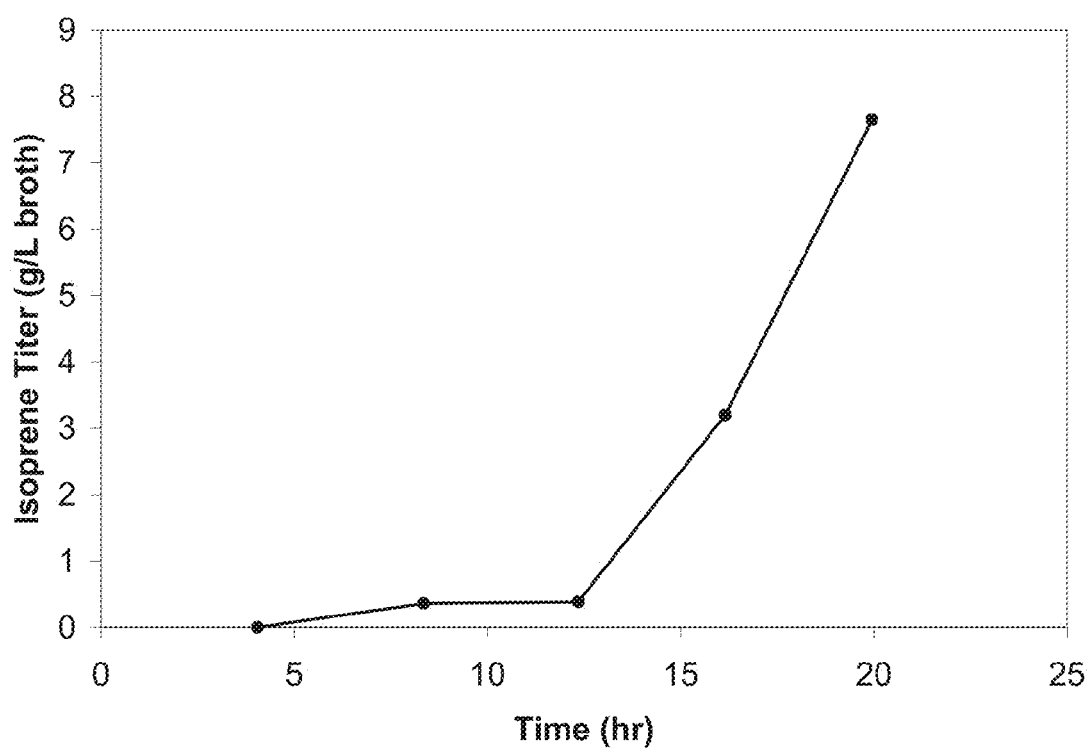
FIG. 5 depicts the time course of isoprene titer. Isoprene production was achieved by the simultaneous saccharification and fermentation process with TrGA and an alpha-amylase as described in Example 8.2. The titer is defined as the amount of isoprene produced per liter of fermentation broth. The equation for calculating isoprene titer.

Accumulated glucose levels in the fermentor broth over time are shown in FIG. 4. Induction was achieved by adding isopropyl-beta-D-1-thiogalactopyranoside (IPTG). The IPTG concentration was brought to 107 μM when the carbon dioxide evolution rate (CER) reached 25 mmol/L/hr. The IPTG concentration was raised to 202 μM when CER reached 175 mmol/L/hr. The isoprene level in the off gas from the bioreactor was determined using a PerkinElmer iScan mass spectrometer. The isoprene titer increased over the course of the fermentation to a maximum value of 7.6 g/L at 20 hrs (FIG. 5). The total amount of isoprene produced during the 20-hour fermentation was 6.0 g. The metabolic activity profile, as measured by the CER, is shown in FIG. 6. Carbon dioxide evolution rate (CER)=[24.851*(airflow slpm/offgas N2%)*supply N2%*offgas $CO_2$%]/(Fermentor kgs/Broth density)

24.851=(60 min/h*1000 mmol/mol)/(100%*24.14 liters/mol)

24.14 liters is how much volume an ideal gas occupies at 1 atm and 21.1 C.

8.3. Isoprene Producing by Simultaneous Saccharification and Fermentation (SSF) from Granular Starch with the *Humicola grisea* Glucoamylase (HgGA)

Granular cornstarch was prepared as described in Example 8.1. to be use for isoprene production by fermentation. Starch hydrolysis was initiated at cell inoculation (time zero) by adding 2 GAU/L broth of HgGA. Additional enzyme was added by continuous feeding in amounts shown in Table 9 in order to obtain a starch hydrolysis rate that roughly matched the glucose consumption rate of the cells. HgGA was diluted in either 36% glucose or water in order to feed.

TABLE 9

Amount of HgGA added to the bioreactor over time.

| Time hr | Amount added H-GA GAU/L broth | Cumulative amount added H-GA GAU/L broth |
|---|---|---|
| 0.0 | 2 | 2 |
| 4.4 | 0 | 2 |
| 8.0 | 0 | 2 |
| 12.0 | 587 | 589 |
| 16.0 | 1383 | 1972 |
| 20.0 | 1353 | 3325 |
| 24.0 | 1961 | 5286 |
| 28.0 | 9638 | 14924 |
| 32.8 | 21963 | 36887 |

At various time points of the SSF, samples were removed and subject to analysis. Accumulated glucose levels in the fermentor broth over time are shown in FIG. 8. Induction was achieved by adding isopropyl-beta-D-1-thiogalactopyranoside (IPTG). The IPTG concentration was brought to 117 μM when the carbon dioxide evolution rate (CER) reached 25 mmol/L/hr. The IPTG concentration was raised to 224 μM when CER reached 175 mmol/L/hr. The isoprene level in the off gas from the bioreactor was determined using a PerkinElmer iScan mass spectrometer. The isoprene titer increased over the course of the fermentation to a maximum value of 5.2 g/L at 35 hrs (FIG. 9). The total amount of isoprene produced during the 35-hour fermentation was 3.4 g. The metabolic activity profile, as measured by the CER, is shown in FIG. 10. The time course of the ratio of isoprene to carbon dioxide in the gas stream exiting the bioreactor, an indicator of product yield, is shown in FIG. 11. It was observed that both the TrGA+AA or H-GA fermentations reached the same peak instantaneous mol isoprene/mol carbon dioxide ratio (roughly 0.08; ratio correlates with instantaneous carbon yield) as a typical glucose fed-batch fermentation. The similarity of these values despite the different conditions indicates that cells produce isoprene in a comparable manner to the traditional process where glucose is fed to the fermentor. More experimentation was performed to elucidate any possible differences between the use of TrGA+AA or H-GA for the stated application, though it was shown that similar amounts of enzymatic activity units were added over the course of the fermentations. No significant differences between the use of TrGA+AA or H-GA were noted in the current data set.

Without being bound by theory, it appears that the TrGA+AA or H-GA activity is inactivated by some component in the fermentation broth, resulting in the need for continued addition of enzyme to the fermentation to produce glucose for cell utilization/isoprene formation. It was also noted that the fermentation broth dissolved oxygen level was lower than the glucose fed-batch fermentation as a result of the higher viscosity caused by the granular starch substrates. The low dissolved oxygen levels are not anticipated to be observed in fermentations utilizing the liquefact substrates.

Example 9

Isoprenoid Production under SSF Conditions Using MVA Pathway Polypeptides

Host cells (e.g., bacterial cells) are engineered to contain nucleic acids encoding for one or more MVA pathway polypeptide and one or more polyprenyl pyrophosphate synthase polypeptides (e.g., geranyl diphosphate (GPP) synthase, farnesyl pyrophosphate (FPP) synthase, and geranylgeranyl pyrophosphate (GGPP) synthase) and optionally IDI. The bacterial cells are cultured under SSF conditions where there is saccharification and fermentation of a starch substrate under simultaneous saccharification and fermentation (SSF) conditions in the presence of a glucoamylase, wherein the saccharification and fermentation are performed at pH 5.0 to 8.0, wherein the glucoamylase possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent *Rhizopus* sp. glucoamylase (RhGA) comprising SEQ ID NO: 9, and a variant thereof, and wherein the variant has at least 99% sequence identity to the parent glucoamylase.

Example 10

Isoprenoid Production under SSF Conditions Using DXP Pathway Polypeptides

Host cells (e.g., bacterial cells) are engineered to contain nucleic acids encoding for one or more DXP pathway polypeptide and one or more polyprenyl pyrophosphate synthase polypeptides (e.g., geranyl diphosphate (GPP) synthase, farnesyl pyrophosphate (FPP) synthase, and geranylgeranyl pyrophosphate (GGPP) synthase) and optionally IDI. The bacterial cells are cultured under SSF conditions where there is saccharification and fermentation of a starch substrate under simultaneous saccharification and fermentation (SSF) conditions in the presence of a glucoamylase, wherein the saccharification and fermentation are performed at pH 5.0 to 8.0, wherein the glucoamylase possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent *Rhizopus* sp. glucoamylase (RhGA) comprising SEQ ID NO: 9, and a variant thereof, and wherein the variant has at least 99% sequence identity to the parent glucoamylase.

Example 11

Isoprenoid Production under SSF Conditions Using MVA and DXP Pathway Polypeptides Host cells (e.g., bacterial cells) are engineered to contain nucleic acids encoding for one or more DXP pathway polypeptide, one or more MVA pathway polypeptides, and one or more polyprenyl pyrophosphate synthase polypeptides (e.g., geranyl diphosphate (GPP) synthase, farnesyl pyrophosphate (FPP) synthase, and geranylgeranyl pyrophosphate (GGPP) synthase) and optionally IDI. The bacterial cells are cultured under SSF conditions where there is saccharification and fermentation of a starch substrate under simultaneous saccharification and fermentation (SSF) conditions in the presence of a glucoamylase, wherein the saccharification and fermentation are performed at pH 5.0 to 8.0, wherein the glucoamylase possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent *Rhizopus* sp. glucoamylase (RhGA) comprising SEQ ID NO: 9, and a variant thereof, and wherein the variant has at least 99% sequence identity to the parent glucoamylase.

What is claimed is:

1. A method for producing an isoprenoid precursor or isoprenoid comprising culturing a host cell, which comprises a heterologous nucleic acid encoding an polyprenyl pyrophosphate synthase polypeptide, and saccharifying and fermenting a starch substrate under simultaneous saccharification and fermentation (SSF) conditions in the presence of a glucoamylase, wherein the saccharification and fermentation are performed at pH 6.5 to 8.0, wherein the glucoamylase possesses at least 50% activity at pH 6.0 or above relative to its maximum activity, wherein the glucoamylase is selected from the group consisting of a parent *Humicola grisea* glucoamylase (HgGA) comprising SEQ ID NO: 3, a parent *Trichoderma reesei* glucoamylase (TrGA) comprising SEQ ID NO: 6, a parent *Rhizopus* sp. glucoamylase (RhGA) comprising SEQ ID NO: 9, and a variant thereof, wherein the variant has at least 99% sequence identity to the parent glucoamylase, and wherein the host cell is selected from the group consisting of bacterial cells, fungal cells, and algal cells.

2. The method of claim 1, wherein the isoprenoid is selected from the group consisting of monoterpenes, diterpenes, triterpenes, tetraterpenes, sequiterpene, and polyterpene.

3. The method of claim 1, wherein the isoprenoid is a sesquiterpene.

4. The method of claim 1, wherein the isoprenoid is selected from the group consisting of abietadiene, amorphadiene, carene, α-farnesene,β-farnesene, farnesol, geraniol, geranylgeraniol, linalool, limonene, myrcene, nerolidol, ocimene, patchoulol,β-pinene, sabinene, γ-terpinene, terpindene and valencene.

5. The method of claim 1, wherein the variant has one amino acid modification compared to the parent glucoamylase.

6. The method of claim 1, wherein the HgGA is produced from a *Trichoderma reesei* host cell.

7. The method of claim 1, wherein the TrGA is SEQ ID No: 6.

8. The method of claim 1, the SSF is carried out at pH 6.5 to 7.5.

9. The method of claim 1, the SSF is carried out at pH 7.0 to 7.5.

10. The method of claim 1, the SSF is performed at a temperature in a range of about 30° C. to about 60° C.

11. The method of claim 1, the SSF is performed at a temperature in a range of about 40° C. to about 60° C.

12. The method of claim 1, the starch substrate is about 15% to 50% dry solid (DS).

13. The method of claim 1, the starch substrate is about 15% to 30% dry solid (DS).

14. The method of claim 1, the starch substrate is about 15% to 25% dry solid (DS).

15. The method of claim 1, the starch substrate is granular starch or liquefied starch.

16. The method of claim 1, the glucoamylase is dosed at a range of about 0.1 to about 2.0 GAU per gram of dry substance starch.

17. The method of claim 1, the glucoamylase is dosed at a range of about 0.2 to about 1.0 GAU per gram of dry substance starch.

18. The method of claim 1, the glucoamylase is dosed at a range of about 0.5 to 1.0 GAU per gram of dry substance starch.

19. The method of claim 1, wherein alpha-amylase is further added to any of the embodiments herein.

20. The method of claim 1, wherein the alpha-amylase is from a *Bacillus* species, or a variant thereof.

21. The method of claim 1, wherein the alpha-amylase is a *Bacillus subtilis* alpha-amylase (AmyE), a *Bacillus amyloliquefaciens* alpha-amylase, a *Bacillus licheniformis* alpha-amylase, a *Bacillus stearothermophilus* alpha-amylase, or a variant thereof.

22. The method of claim 1, wherein the starch substrate is from corn, wheat, rye, barley, sorghum, cassava, tapioca, and any combination thereof.

23. The method of claim 1, wherein the heterologous nucleic acid is operably linked to a promoter and wherein the production of isoprenoids by the cells is greater than about 5 g/L.

24. The method of claim 1, wherein the host cell further comprise one or more heterologous nucleic acid encoding a mevalonate (MVA) pathway polypeptide and/or a DXP pathway polypeptide.

25. The method of claim 1, wherein the bacterial cells are selected from the group consisting of gram-positive bacterial cells, gram-negative bacterial cells, *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

26. The method of claim 1, wherein the fungal cells are selected from the group consisting of *Aspergillus*, yeast, *Trichoderma*, or *Yarrowia* cells.

27. The method of claim 25, wherein the yeast is *Saccharomyces* sp., *Schizosaccharomyces* sp., *Pichia* sp., *Candida* sp. or *Y. lipolytica* cells.

28. The method of claim 1, wherein the fungal cells are selected from the group consisting of *A. oryzae, A. niger, S. cerevisiae, S. pombe, T. reesei, H. insolens, H. lanuginose, H. grisea, C. lucknowense, A. oryzae, A. niger, A sojae, A. japonicus, A. nidulans, A. aculeatus, A. awamori, F. roseum, F. graminum F. cerealis, F. oxysporuim, F. venenatum, N. crassa, M. miehei, T. viride, F. oxysporum,* and *F. solan* cells.

* * * * *

```
SEQUENCE LISTING

<160> NUMBER OF SEQ ID NOS: 10

<210> SEQ ID NO 1
<211> LENGTH: 2103
<212> TYPE: DNA
<213> ORGANISM: Humicola grisea

<400> SEQUENCE: 1
atgcatacct tctccaagct cctcgtcctg ggctctgccg tccagtctgc cctcgggcgg      60
cctcacggct cttcgcgtct ccaggaacgc gctgccgttg ataccttcat caacaccgag     120
aagcccatcg catggaacaa gctgctcgcc aacatcggcc ctaacggcaa agccgctccc     180
ggtgccgccg ccggcgttgt gattgccagc ccttccagga cggaccctcc ttgtacgtgg     240
tggcatggaa tggacccaag agactggttt tagatgaaag agagtttctg ctaaccgcca     300
cacccagact tcttcacctg gacccgcgat gccgccctgg tcctcaccgg catcatcgag     360
tcccttggcc acaactacaa caccaccctg cagaccgtca tccagaacta cgtcgcgtcg     420
caggccaagc tgcagcaggt ctcgaacccc tcgggaacct tcgccgacgg ctcgggtctc     480
ggtgaggcca agttcaatgt cgacctcact gccttcactg gcgaatgggg tcgccctcag     540
agggacggcc cgcccctgcg cgccatcgct ctcatccagt acgccaagtg gctgatcgcc     600
aacggctaca gagcacggc caagagcgtc gtctggcccg tcgtcaagaa cgatctcgcc     660
tacacggccc agtactggaa cgagaccggc ttcgatctct gggaggaggt ccccggcagc     720
tcgttcttta ccatcgccag ctctcacagg ggtgagtcat ttattgttca gtgttttctc     780
attgaataat taccggaatg ccactgacgc caaacagctc tgactgaggg tgcttacctc     840
gccgctcagc tcgacaccga gtgccgcgcc tgcacgaccg tcgcccctca ggttctgtgc     900
ttccagcagg ccttctggaa ctccaagggc aactatgtcg tctccaacag taagatccct     960
acaccaacaa aaaaaatcga aaaggaacgt tagctgaccc ttctagtcaa cggcggcgag    1020
tatcgctccg gcaaggacgc caactcgatc ctggcgtcca tccacaactt cgaccctgag    1080
```

```
gccggctgcg acaacctgac cttccagccc tgcagcgagc gcgccctggc caaccacaag    1140
gcctatgtcg actcgttccg caacctctac gccatcaaca agggcatcgc ccagggcaag    1200
gccgttgccg tcggccgcta ctcggaggat gtctactaca acggcaaccc gtggtacctg    1260
gccaactttg ccgccgccga gcagctctac gacgccatct acgtgtggaa caagcagggc    1320
tccatcaccg tgacctcggt ctccctgccc ttcttccgcg accttgtctc gtcggtcagc    1380
accggcacct actccaagag cagctcgacc ttcaccaaca tcgtcaacgc cgtcaaggcc    1440
tacgccgacg gcttcatcga ggtggcggcc aagtacaccc cgtccaacgg cgcgctcgcc    1500
gagcagtacg accgcaacac gggcaagccc gactcggccg ccgacctgac gtggtcgtac    1560
tcggccttcc tctcggccat cgaccgccgc gcgggtctcg tcccccgag ctggcgggcc     1620
agcgtggcca agagccagct gccgtccacc tgctcgcgca tcgaggtcgc cggcacctac    1680
gtcgccgcca cgagcacctc gttcccgtcc aagcagaccc cgaaccctc gcggcgcccc     1740
tccccgtccc cctacccgac cgcctgcgcg gacgctagcg aggtgtacgt caccttcaac    1800
gagcgcgtgt cgaccgcgtg gggcgagacc atcaaggtgg tgggcaacgt gccggcgctg    1860
gggaactggg acacgtccaa ggcggtgacc ctgtcggcca gcgggtacaa gtcgaatgat    1920
cccctctgga gcatcacggt gcccatcaag gcgacgggct cggccgtgca gtacaagtat    1980
atcaaggtcg gcaccaacgg gaagattact tgggagtcgg accccaacag gagcattacc    2040
ctgcagacgg cgtcgtctgc gggcaagtgc gccgcgcaga cggtgaatga ttcgtggcgt    2100
taa                                                                  2103

<210> SEQ ID NO 2
<211> LENGTH: 634
<212> TYPE: PRT
<213> ORGANISM: Humicola grisea

<400> SEQUENCE: 2

Met His Thr Phe Ser Lys Leu Leu Val Leu Gly Ser Ala Val Gln Ser
 1               5                  10                  15

Ala Leu Gly Arg Pro His Gly Ser Ser Arg Leu Gln Glu Arg Ala Ala
            20                  25                  30

Val Asp Thr Phe Ile Asn Thr Glu Lys Pro Ile Ala Trp Asn Lys Leu
        35                  40                  45

Leu Ala Asn Ile Gly Pro Asn Gly Lys Ala Ala Pro Gly Ala Ala Ala
    50                  55                  60

Gly Val Val Ile Ala Ser Pro Ser Arg Thr Asp Pro Pro Tyr Phe Phe
65                  70                  75                  80

Thr Trp Thr Arg Asp Ala Ala Leu Val Leu Thr Gly Ile Ile Glu Ser
                85                  90                  95

Leu Gly His Asn Tyr Asn Thr Thr Leu Gln Thr Val Ile Gln Asn Tyr
            100                 105                 110

Val Ala Ser Gln Ala Lys Leu Gln Gln Val Ser Asn Pro Ser Gly Thr
        115                 120                 125

Phe Ala Asp Gly Ser Gly Leu Gly Glu Ala Lys Phe Asn Val Asp Leu
    130                 135                 140

Thr Ala Phe Thr Gly Glu Trp Gly Arg Pro Gln Arg Asp Gly Pro Pro
145                 150                 155                 160

Leu Arg Ala Ile Ala Leu Ile Gln Tyr Ala Lys Trp Leu Ile Ala Asn
                165                 170                 175

Gly Tyr Lys Ser Thr Ala Lys Ser Val Val Trp Pro Val Val Lys Asn
            180                 185                 190
```

```
Asp Leu Ala Tyr Thr Ala Gln Tyr Trp Asn Glu Thr Gly Phe Asp Leu
            195                 200                 205

Trp Glu Glu Val Pro Gly Ser Ser Phe Phe Thr Ile Ala Ser Ser His
210                 215                 220

Arg Ala Leu Thr Glu Gly Ala Tyr Leu Ala Ala Gln Leu Asp Thr Glu
225                 230                 235                 240

Cys Arg Ala Cys Thr Thr Val Ala Pro Gln Val Leu Cys Phe Gln Gln
                245                 250                 255

Ala Phe Trp Asn Ser Lys Gly Asn Tyr Val Val Ser Asn Ile Asn Gly
                260                 265                 270

Gly Glu Tyr Arg Ser Gly Lys Asp Ala Asn Ser Ile Leu Ala Ser Ile
            275                 280                 285

His Asn Phe Asp Pro Glu Ala Gly Cys Asp Asn Leu Thr Phe Gln Pro
290                 295                 300

Cys Ser Glu Arg Ala Leu Ala Asn His Lys Ala Tyr Val Asp Ser Phe
305                 310                 315                 320

Arg Asn Leu Tyr Ala Ile Asn Lys Gly Ile Ala Gln Gly Lys Ala Val
                325                 330                 335

Ala Val Gly Arg Tyr Ser Glu Asp Val Tyr Tyr Asn Gly Asn Pro Trp
                340                 345                 350

Tyr Leu Ala Asn Phe Ala Ala Ala Glu Gln Leu Tyr Asp Ala Ile Tyr
            355                 360                 365

Val Trp Asn Lys Gln Gly Ser Ile Thr Val Thr Ser Val Ser Leu Pro
370                 375                 380

Phe Phe Arg Asp Leu Val Ser Ser Val Ser Thr Gly Thr Tyr Ser Lys
385                 390                 395                 400

Ser Ser Ser Thr Phe Thr Asn Ile Val Asn Ala Val Lys Ala Tyr Ala
                405                 410                 415

Asp Gly Phe Ile Glu Val Ala Ala Lys Tyr Thr Pro Ser Asn Gly Ala
                420                 425                 430

Leu Ala Glu Gln Tyr Asp Arg Asn Thr Gly Lys Pro Asp Ser Ala Ala
            435                 440                 445

Asp Leu Thr Trp Ser Tyr Ser Ala Phe Leu Ser Ala Ile Asp Arg Arg
450                 455                 460

Ala Gly Leu Val Pro Pro Ser Trp Arg Ala Ser Val Ala Lys Ser Gln
465                 470                 475                 480

Leu Pro Ser Thr Cys Ser Arg Ile Glu Val Ala Gly Thr Tyr Val Ala
                485                 490                 495

Ala Thr Ser Thr Ser Phe Pro Ser Lys Gln Thr Pro Asn Pro Ser Ala
                500                 505                 510

Ala Pro Ser Pro Ser Pro Tyr Pro Thr Ala Cys Ala Asp Ala Ser Glu
            515                 520                 525

Val Tyr Val Thr Phe Asn Glu Arg Val Ser Thr Ala Trp Gly Glu Thr
530                 535                 540

Ile Lys Val Val Gly Asn Val Pro Ala Leu Gly Asn Trp Asp Thr Ser
545                 550                 555                 560

Lys Ala Val Thr Leu Ser Ala Ser Gly Tyr Lys Ser Asn Asp Pro Leu
                565                 570                 575

Trp Ser Ile Thr Val Pro Ile Lys Ala Thr Gly Ser Ala Val Gln Tyr
            580                 585                 590

Lys Tyr Ile Lys Val Gly Thr Asn Gly Lys Ile Thr Trp Glu Ser Asp
            595                 600                 605
```

```
Pro Asn Arg Ser Ile Thr Leu Gln Thr Ala Ser Ser Ala Gly Lys Cys
        610                 615                 620

Ala Ala Gln Thr Val Asn Asp Ser Trp Arg
625                 630

<210> SEQ ID NO 3
<211> LENGTH: 604
<212> TYPE: PRT
<213> ORGANISM: Humicola grisea

<400> SEQUENCE: 3

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65                  70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110

Asp Leu Thr Ala Phe Thr Gly Glu Trp Gly Arg Pro Gln Arg Asp Gly
        115                 120                 125

Pro Pro Leu Arg Ala Ile Ala Leu Ile Gln Tyr Ala Lys Trp Leu Ile
130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205

Thr Glu Cys Arg Ala Cys Thr Thr Val Ala Pro Gln Val Leu Cys Phe
210                 215                 220

Gln Gln Ala Phe Trp Asn Ser Lys Gly Asn Tyr Val Val Ser Asn Ile
225                 230                 235                 240

Asn Gly Gly Glu Tyr Arg Ser Gly Lys Asp Ala Asn Ser Ile Leu Ala
                245                 250                 255

Ser Ile His Asn Phe Asp Pro Glu Ala Gly Cys Asp Asn Leu Thr Phe
            260                 265                 270

Gln Pro Cys Ser Glu Arg Ala Leu Ala Asn His Lys Ala Tyr Val Asp
        275                 280                 285

Ser Phe Arg Asn Leu Tyr Ala Ile Asn Lys Gly Ile Ala Gln Gly Lys
    290                 295                 300

Ala Val Ala Val Gly Arg Tyr Ser Glu Asp Val Tyr Tyr Asn Gly Asn
305                 310                 315                 320

Pro Trp Tyr Leu Ala Asn Phe Ala Ala Ala Glu Gln Leu Tyr Asp Ala
                325                 330                 335

Ile Tyr Val Trp Asn Lys Gln Gly Ser Ile Thr Val Thr Ser Val Ser
            340                 345                 350
```

Leu Pro Phe Phe Arg Asp Leu Val Ser Ser Val Ser Thr Gly Thr Tyr
        355                 360                 365

Ser Lys Ser Ser Ser Thr Phe Thr Asn Ile Val Asn Ala Val Lys Ala
    370                 375                 380

Tyr Ala Asp Gly Phe Ile Glu Val Ala Ala Lys Tyr Thr Pro Ser Asn
385                 390                 395                 400

Gly Ala Leu Ala Glu Gln Tyr Asp Arg Asn Thr Gly Lys Pro Asp Ser
                405                 410                 415

Ala Ala Asp Leu Thr Trp Ser Tyr Ser Ala Phe Leu Ser Ala Ile Asp
                420                 425                 430

Arg Arg Ala Gly Leu Val Pro Pro Ser Trp Arg Ala Ser Val Ala Lys
                435                 440                 445

Ser Gln Leu Pro Ser Thr Cys Ser Arg Ile Glu Val Ala Gly Thr Tyr
    450                 455                 460

Val Ala Ala Thr Ser Thr Ser Phe Pro Ser Lys Gln Thr Pro Asn Pro
465                 470                 475                 480

Ser Ala Ala Pro Ser Pro Ser Pro Tyr Pro Thr Ala Cys Ala Asp Ala
                485                 490                 495

Ser Glu Val Tyr Val Thr Phe Asn Glu Arg Val Ser Thr Ala Trp Gly
                500                 505                 510

Glu Thr Ile Lys Val Val Gly Asn Val Pro Ala Leu Gly Asn Trp Asp
            515                 520                 525

Thr Ser Lys Ala Val Thr Leu Ser Ala Ser Gly Tyr Lys Ser Asn Asp
            530                 535                 540

Pro Leu Trp Ser Ile Thr Val Pro Ile Lys Ala Thr Gly Ser Ala Val
545                 550                 555                 560

Gln Tyr Lys Tyr Ile Lys Val Gly Thr Asn Gly Lys Ile Thr Trp Glu
                565                 570                 575

Ser Asp Pro Asn Arg Ser Ile Thr Leu Gln Thr Ala Ser Ser Ala Gly
                580                 585                 590

Lys Cys Ala Ala Gln Thr Val Asn Asp Ser Trp Arg
            595                 600

<210> SEQ ID NO 4
<211> LENGTH: 1899
<212> TYPE: DNA
<213> ORGANISM: Trichoderma reesei

<400> SEQUENCE: 4
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc     120
accgagacgc ctattgcact gaacaatctt ctttgcaatg ttggtcctga tggatgccgt     180
gcattcggca catcagctgg tgcggtgatt gcatctccca gcacaattga cccggactac     240
tattacatgt ggacgcgaga tagcgctctt gtcttcaaga acctcatcga ccgcttcacc     300
gaaacgtacg atgcgggcct gcagcgccgc atcgagcagt acattactgc ccaggtcact     360
ctccagggcc tctctaaccc ctcgggctcc ctcgcggacg gctctggtct cggcgagccc     420
aagtttgagt tgaccctgaa gcctttcacc ggcaactggg gtcgaccgca gcggatggc     480 ccagctctgc gagccattgc cttgattgga tactcaaagt ggctcatcaa caacaactat     540
cagtcgactg tgtccaacgt catctggcct attgtgcgca acgacctcaa ctatgttgcc     600
cagtactgga accaaaccgg ctttgacctc tgggaagaag tcaatgggag ctcattcttt     660

```
actgttgcca accagcaccg agcacttgtc gagggcgcca ctcttgctgc cactcttggc    720
cagtcgggaa gcgcttattc atctgttgct ccccaggttt tgtgctttct ccaacgattc    780
tgggtgtcgt ctggtggata cgtcgactcc aacatcaaca ccaacgaggg caggactggc    840
aaggatgtca actccgtcct gacttccatc cacaccttcg atcccaacct tggctgtgac    900
gcaggcacct tccagccatg cagtgacaaa gcgctctcca acctcaaggt tgttgtcgac    960
tccttccgct ccatctacgg cgtgaacaag ggcattcctg ccggtgctgc cgtcgccatt   1020
ggccggtatg cagaggatgt gtactacaac ggcaacccct tggtatcttg ctacatttgct   1080
gctgccgagc agctgtacga tgccatctac gtctggaaga agacgggctc catcacggtg   1140
accgccacct ccctggcctt cttccaggag cttgttcctg gcgtgacggc cgggacctac   1200
tccagcagct cttcgacctt taccaacatc atcaacgccg tctcgacata cgccgatggc   1260
ttcctcagcg aggctgccaa gtacgtcccc gccgacggtt cgctggccga gcagtttgac   1320
cgcaacagcg gcactccgct gtctgcgctt cacctgacgt ggtcgtacgc ctcgttcttg   1380
acagccacgg cccgtcgggc tggcatcgtg ccccccctcgt gggccaacag cagcgctagc   1440
acgatcccct cgacgtgctc cggcgcgtcc gtggtcggat cctactcgcg tcccaccgcc   1500
acgtcattcc ctccgtcgca gacgcccaag cctggcgtgc cttccggtac tccctacacg   1560
cccctgccct gcgcgacccc aacctccgtg gccgtcacct ccacgagct cgtgtcgaca   1620
cagtttggcc agacggtcaa ggtggcgggc aacgccgcgg ccctgggcaa ctggagcacg   1680
agcgccgccg tggctctgga cgccgtcaac tatgccgata accaccccct gtggattggg   1740
acggtcaacc tcgaggctgg agacgtcgtg gagtacaagt acatcaatgt gggccaagat   1800
ggctccgtga cctgggagag tgatcccaac cacacttaca cggttcctgc ggtggcttgt   1860
gtgacgcagg ttgtcaagga ggacacctgg cagtcgtaa                          1899
```

<210> SEQ ID NO 5
<211> LENGTH: 632
<212> TYPE: PRT
<213> ORGANISM: Trichoderma reesei

<400> SEQUENCE: 5

```
Met His Val Leu Ser Thr Ala Val Leu Leu Gly Ser Val Ala Val Gln
  1               5                  10                  15

Lys Val Leu Gly Arg Pro Gly Ser Ser Gly Leu Ser Asp Val Thr Lys
             20                  25                  30

Arg Ser Val Asp Asp Phe Ile Ser Thr Glu Thr Pro Ile Ala Leu Asn
         35                  40                  45

Asn Leu Leu Cys Asn Val Gly Pro Asp Gly Cys Arg Ala Phe Gly Thr
     50                  55                  60

Ser Ala Gly Ala Val Ile Ala Ser Pro Ser Thr Ile Asp Pro Asp Tyr
 65                  70                  75                  80

Tyr Tyr Met Trp Thr Arg Asp Ser Ala Leu Val Phe Lys Asn Leu Ile
                 85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160
```

```
Pro Ala Leu Arg Ala Ile Ala Leu Ile Gly Tyr Ser Lys Trp Leu Ile
            165                 170                 175

Asn Asn Asn Tyr Gln Ser Thr Val Ser Asn Val Ile Trp Pro Ile Val
        180                 185                 190

Arg Asn Asp Leu Asn Tyr Val Ala Gln Tyr Trp Asn Gln Thr Gly Phe
    195                 200                 205

Asp Leu Trp Glu Glu Val Asn Gly Ser Ser Phe Phe Thr Val Ala Asn
210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
            245                 250                 255

Leu Gln Arg Phe Trp Val Ser Ser Gly Gly Tyr Val Asp Ser Asn Ile
        260                 265                 270

Asn Thr Asn Glu Gly Arg Thr Gly Lys Asp Val Asn Ser Val Leu Thr
    275                 280                 285

Ser Ile His Thr Phe Asp Pro Asn Leu Gly Cys Asp Ala Gly Thr Phe
290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
            325                 330                 335

Ala Val Ala Ile Gly Arg Tyr Ala Glu Asp Val Tyr Tyr Asn Gly Asn
        340                 345                 350

Pro Trp Tyr Leu Ala Thr Phe Ala Ala Glu Gln Leu Tyr Asp Ala
    355                 360                 365

Ile Tyr Val Trp Lys Lys Thr Gly Ser Ile Thr Val Thr Ala Thr Ser
370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
            405                 410                 415

Tyr Ala Asp Gly Phe Leu Ser Glu Ala Ala Lys Tyr Val Pro Ala Asp
        420                 425                 430

Gly Ser Leu Ala Glu Gln Phe Asp Arg Asn Ser Gly Thr Pro Leu Ser
    435                 440                 445

Ala Leu His Leu Thr Trp Ser Tyr Ala Ser Phe Leu Thr Ala Thr Ala
450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
            485                 490                 495

Arg Pro Thr Ala Thr Ser Phe Pro Pro Ser Gln Thr Pro Lys Pro Gly
        500                 505                 510

Val Pro Ser Gly Thr Pro Tyr Thr Pro Leu Pro Cys Ala Thr Pro Thr
    515                 520                 525

Ser Val Ala Val Thr Phe His Glu Leu Val Ser Thr Gln Phe Gly Gln
530                 535                 540

Thr Val Lys Val Ala Gly Asn Ala Ala Leu Gly Asn Trp Ser Thr
545                 550                 555                 560

Ser Ala Ala Val Ala Leu Asp Ala Val Asn Tyr Ala Asp Asn His Pro
            565                 570                 575
```

```
Leu Trp Ile Gly Thr Val Asn Leu Glu Ala Gly Asp Val Val Glu Tyr
            580                 585                 590

Lys Tyr Ile Asn Val Gly Gln Asp Gly Ser Val Thr Trp Glu Ser Asp
        595                 600                 605

Pro Asn His Thr Tyr Thr Val Pro Ala Val Ala Cys Val Thr Gln Val
    610                 615                 620

Val Lys Glu Asp Thr Trp Gln Ser
625                 630

<210> SEQ ID NO 6
<211> LENGTH: 599
<212> TYPE: PRT
<213> ORGANISM: Trichoderma reesei

<400> SEQUENCE: 6

Ser Val Asp Asp Phe Ile Ser Thr Glu Thr Pro Ile Ala Leu Asn Asn
  1               5                  10                  15

Leu Leu Cys Asn Val Gly Pro Asp Gly Cys Arg Ala Phe Gly Thr Ser
             20                  25                  30

Ala Gly Ala Val Ile Ala Ser Pro Ser Thr Ile Asp Pro Asp Tyr Tyr
         35                  40                  45

Tyr Met Trp Thr Arg Asp Ser Ala Leu Val Phe Lys Asn Leu Ile Asp
     50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                 85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320
```

```
Trp Tyr Leu Ala Thr Phe Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
        435                 440                 445

Ile Pro Ser Thr Cys Ser Gly Ala Ser Val Val Gly Ser Tyr Ser Arg
    450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
                485                 490                 495

Val Ala Val Thr Phe His Glu Leu Val Ser Thr Gln Phe Gly Gln Thr
            500                 505                 510

Val Lys Val Ala Gly Asn Ala Ala Leu Gly Asn Trp Ser Thr Ser
        515                 520                 525

Ala Ala Val Ala Leu Asp Ala Val Asn Tyr Ala Asp Asn His Pro Leu
    530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
            580                 585                 590

Lys Glu Asp Thr Trp Gln Ser
        595

<210> SEQ ID NO 7
<211> LENGTH: 453
<212> TYPE: PRT
<213> ORGANISM: Trichoderma reesei

<400> SEQUENCE: 7

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
```

Ser Leu Ala Asp Gly Ser Gly Leu Gly Glu Pro Lys Phe Glu Leu Thr
    85                  90                  95              100

Leu Lys Pro Phe Thr Gly Asn Trp Gly Arg Pro Gln Arg Asp Gly Pro
            115                 120                 125

Ala Leu Arg Ala Ile Ala Leu Ile Gly Tyr Ser Lys Trp Leu Ile Asn
            130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
            195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
    275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
            435                 440                 445

Ile Pro Ser Thr Cys
    450

<210> SEQ ID NO 8
<211> LENGTH: 604
<212> TYPE: PRT
<213> ORGANISM: Rhizopus oryzae

<400> SEQUENCE: 8

```
Met Gln Leu Phe Asn Leu Pro Leu Lys Val Ser Phe Phe Leu Val Leu
 1               5                  10                  15

Ser Tyr Phe Ser Leu Leu Val Ser Ala Ala Ser Ile Pro Ser Ser Ala
            20                  25                  30

Ser Val Gln Leu Asp Ser Tyr Asn Tyr Asp Gly Ser Thr Phe Ser Gly
            35                  40                  45

Lys Ile Tyr Val Lys Asn Ile Ala Tyr Ser Lys Lys Val Thr Val Ile
 50                  55                  60

Tyr Ala Asp Gly Ser Asp Asn Trp Asn Asn Gly Asn Thr Ile Ala
 65                  70                  75                  80

Ala Ser Tyr Ser Ala Pro Ile Ser Gly Ser Asn Tyr Glu Tyr Trp Thr
                85                  90                  95

Phe Ser Ala Ser Ile Asn Gly Ile Lys Glu Phe Tyr Ile Lys Tyr Glu
                100                 105                 110

Val Ser Gly Lys Thr Tyr Tyr Asp Asn Asn Ser Ala Asn Tyr Gln
            115                 120                 125

Val Ser Thr Ser Lys Pro Thr Thr Thr Ala Thr Ala Thr Thr
 130                 135                 140

Thr Ala Pro Ser Thr Ser Thr Thr Thr Pro Pro Ser Arg Ser Glu Pro
145                 150                 155                 160

Ala Thr Phe Pro Thr Gly Asn Ser Thr Ile Ser Ser Trp Ile Lys Lys
                165                 170                 175

Gln Glu Gly Ile Ser Arg Phe Ala Met Leu Arg Asn Ile Asn Pro Pro
                180                 185                 190

Gly Ser Ala Thr Gly Phe Ile Ala Ala Ser Leu Ser Thr Ala Gly Pro
                195                 200                 205

Asp Tyr Tyr Tyr Ala Trp Thr Arg Asp Ala Ala Leu Thr Ser Asn Val
            210                 215                 220

Ile Val Tyr Glu Tyr Asn Thr Thr Leu Ser Gly Asn Lys Thr Ile Leu
225                 230                 235                 240

Asn Val Leu Lys Asp Tyr Val Thr Phe Ser Val Lys Thr Gln Ser Thr
                245                 250                 255

Ser Thr Val Cys Asn Cys Leu Gly Glu Pro Lys Phe Asn Pro Asp Ala
                260                 265                 270

Ser Gly Tyr Thr Gly Ala Trp Gly Arg Pro Gln Asn Asp Gly Pro Ala
            275                 280                 285

Glu Arg Ala Thr Thr Phe Ile Leu Phe Ala Asp Ser Tyr Leu Thr Gln
            290                 295                 300

Thr Lys Asp Ala Ser Tyr Val Thr Gly Thr Leu Lys Pro Ala Ile Phe
305                 310                 315                 320

Lys Asp Leu Asp Tyr Val Val Asn Val Trp Ser Asn Gly Cys Phe Asp
                325                 330                 335

Leu Trp Glu Glu Val Asn Gly Val His Phe Tyr Thr Leu Met Val Met
                340                 345                 350

Arg Lys Gly Leu Leu Gly Ala Asp Phe Ala Lys Arg Asn Gly Asp
            355                 360                 365

Ser Thr Arg Ala Ser Thr Tyr Ser Ser Thr Ala Ser Thr Ile Ala Asn
            370                 375                 380

Lys Ile Ser Ser Phe Trp Val Ser Asn Asn Trp Ile Gln Val Ser
385                 390                 395                 400

Gln Ser Val Thr Gly Gly Val Ser Lys Lys Gly Leu Asp Val Ser Thr
                405                 410                 415

Leu Leu Ala Ala Asn Leu Gly Ser Val Asp Asp Gly Phe Phe Thr Pro
```

```
                420             425             430
Gly Ser Glu Lys Ile Leu Ala Thr Ala Val Ala Val Glu Asp Ser Phe
            435                 440                 445

Ala Ser Leu Tyr Pro Ile Asn Lys Asn Leu Pro Ser Tyr Leu Gly Asn
450                 455                 460

Ser Ile Gly Arg Tyr Pro Glu Asp Thr Tyr Asn Gly Asn Gly Asn Ser
465                 470                 475                 480

Gln Gly Asn Ser Trp Phe Leu Ala Val Thr Gly Tyr Ala Glu Leu Tyr
            485                 490                 495

Tyr Arg Ala Ile Lys Glu Trp Ile Gly Asn Gly Gly Val Thr Val Ser
        500                 505                 510

Ser Ile Ser Leu Pro Phe Phe Lys Lys Phe Asp Ser Ser Ala Thr Ser
        515                 520                 525

Gly Lys Lys Tyr Thr Val Gly Thr Ser Asp Phe Asn Asn Leu Ala Gln
        530                 535                 540

Asn Ile Ala Leu Ala Ala Asp Arg Phe Leu Ser Thr Val Gln Leu His
545                 550                 555                 560

Ala His Asn Asn Gly Ser Leu Ala Glu Glu Phe Asp Arg Thr Thr Gly
            565                 570                 575

Leu Ser Thr Gly Ala Arg Asp Leu Thr Trp Ser His Ala Ser Leu Ile
        580                 585                 590

Thr Ala Ser Tyr Ala Lys Ala Gly Pro Ala Ala
        595                 600

<210> SEQ ID NO 9
<211> LENGTH: 579
<212> TYPE: PRT
<213> ORGANISM: Rhizopus oryzae

<400> SEQUENCE: 9

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Ile Tyr Ala Asp Gly Ser Asp Asn Trp Asn
        35                  40                  45

Asn Asn Gly Asn Thr Ile Ala Ala Ser Tyr Ser Ala Pro Ile Ser Gly
50                  55                  60

Ser Asn Tyr Glu Tyr Trp Thr Phe Ser Ala Ser Ile Asn Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr Ser Lys Pro Thr Thr Thr
            100                 105                 110

Thr Ala Thr Ala Thr Thr Thr Ala Pro Ser Thr Ser Thr Thr Thr
        115                 120                 125

Pro Pro Ser Arg Ser Glu Pro Ala Thr Phe Pro Thr Gly Asn Ser Thr
130                 135                 140

Ile Ser Ser Trp Ile Lys Lys Gln Glu Gly Ile Ser Arg Phe Ala Met
145                 150                 155                 160

Leu Arg Asn Ile Asn Pro Pro Gly Ser Ala Thr Gly Phe Ile Ala Ala
                165                 170                 175

Ser Leu Ser Thr Ala Gly Pro Asp Tyr Tyr Tyr Ala Trp Thr Arg Asp
            180                 185                 190
```

```
Ala Ala Leu Thr Ser Asn Val Ile Val Tyr Glu Tyr Asn Thr Thr Leu
            195                 200                 205

Ser Gly Asn Lys Thr Ile Leu Asn Val Leu Lys Asp Tyr Val Thr Phe
210                 215                 220

Ser Val Lys Thr Gln Ser Thr Ser Thr Val Cys Asn Cys Leu Gly Glu
225                 230                 235                 240

Pro Lys Phe Asn Pro Asp Ala Ser Gly Tyr Thr Gly Ala Trp Gly Arg
                245                 250                 255

Pro Gln Asn Asp Gly Pro Ala Glu Arg Ala Thr Thr Phe Ile Leu Phe
                260                 265                 270

Ala Asp Ser Tyr Leu Thr Gln Thr Lys Asp Ala Ser Tyr Val Thr Gly
            275                 280                 285

Thr Leu Lys Pro Ala Ile Phe Lys Asp Leu Asp Tyr Val Val Asn Val
        290                 295                 300

Trp Ser Asn Gly Cys Phe Asp Leu Trp Glu Glu Val Asn Gly Val His
305                 310                 315                 320

Phe Tyr Thr Leu Met Val Met Arg Lys Gly Leu Leu Leu Gly Ala Asp
                325                 330                 335

Phe Ala Lys Arg Asn Gly Asp Ser Thr Arg Ala Ser Thr Tyr Ser Ser
                340                 345                 350

Thr Ala Ser Thr Ile Ala Asn Lys Ile Ser Ser Phe Trp Val Ser Ser
            355                 360                 365

Asn Asn Trp Ile Gln Val Ser Gln Ser Val Thr Gly Gly Val Ser Lys
        370                 375                 380

Lys Gly Leu Asp Val Ser Thr Leu Leu Ala Ala Asn Leu Gly Ser Val
385                 390                 395                 400

Asp Asp Gly Phe Phe Thr Pro Gly Ser Glu Lys Ile Leu Ala Thr Ala
                405                 410                 415

Val Ala Val Glu Asp Ser Phe Ala Ser Leu Tyr Pro Ile Asn Lys Asn
            420                 425                 430

Leu Pro Ser Tyr Leu Gly Asn Ser Ile Gly Arg Tyr Pro Glu Asp Thr
        435                 440                 445

Tyr Asn Gly Asn Gly Asn Ser Gln Gly Asn Ser Trp Phe Leu Ala Val
450                 455                 460

Thr Gly Tyr Ala Glu Leu Tyr Tyr Arg Ala Ile Lys Glu Trp Ile Gly
465                 470                 475                 480

Asn Gly Gly Val Thr Val Ser Ser Ile Ser Leu Pro Phe Phe Lys Lys
                485                 490                 495

Phe Asp Ser Ser Ala Thr Ser Gly Lys Lys Tyr Thr Val Gly Thr Ser
                500                 505                 510

Asp Phe Asn Asn Leu Ala Gln Asn Ile Ala Leu Ala Ala Asp Arg Phe
            515                 520                 525

Leu Ser Thr Val Gln Leu His Ala His Asn Asn Gly Ser Leu Ala Glu
        530                 535                 540

Glu Phe Asp Arg Thr Thr Gly Leu Ser Thr Gly Ala Arg Asp Leu Thr
545                 550                 555                 560

Trp Ser His Ala Ser Leu Ile Thr Ala Ser Tyr Ala Lys Ala Gly Ala
                565                 570                 575

Pro Ala Ala

<210> SEQ ID NO 10
<211> LENGTH: 125
<212> TYPE: DNA
<213> ORGANISM: Enterobacteria phage lambda
```

```
<400> SEQUENCE: 10
aattcatata aaaaacatac agataaccat ctgcggtgat aaattatctc tggcggtgtt        60
gacataaata ccactggcgg tgatactgag cacatcagca ggacgcactg accaccatga       120
aggtg                                                                   125
```